US009993409B2

(12) United States Patent
Lagrange et al.

(10) Patent No.: US 9,993,409 B2
(45) Date of Patent: Jun. 12, 2018

(54) COMPOSITION FOR DYEING KERATIN FIBRES, COMPRISING AN OXIDATION BASE AND A PARTICULAR HETEROARYL COUPLER

(71) Applicant: L'OREAL, Paris (FR)

(72) Inventors: Alain Lagrange, Coupvray (FR); Boris Lalleman, Paris (FR)

(73) Assignee: L'OREAL, Paris (FR)

( * ) Notice: Subject to any disclaimer, the term of this patent is extended or adjusted under 35 U.S.C. 154(b) by 0 days. days.

(21) Appl. No.: 15/311,263

(22) PCT Filed: May 13, 2015

(86) PCT No.: PCT/EP2015/060642
§ 371 (c)(1),
(2) Date: Nov. 15, 2016

(87) PCT Pub. No.: WO2015/173324
PCT Pub. Date: Nov. 19, 2015

(65) Prior Publication Data
US 2017/0087075 A1  Mar. 30, 2017

(30) Foreign Application Priority Data

May 16, 2014  (FR) ...................................... 14 54407

(51) Int. Cl.
*A61Q 5/10* (2006.01)
*A61K 8/49* (2006.01)
*A61K 8/41* (2006.01)

(52) U.S. Cl.
CPC ................ *A61K 8/49* (2013.01); *A61K 8/411* (2013.01); *A61K 8/494* (2013.01); *A61Q 5/10* (2013.01); *A61K 2800/4324* (2013.01); *A61K 2800/882* (2013.01)

(58) Field of Classification Search
CPC ............. A61K 8/49; A61K 8/411; A61Q 5/10
See application file for complete search history.

(56) References Cited

U.S. PATENT DOCUMENTS

| 4,003,699 A | 1/1977 | Rose et al. |
| RE30,199 E | 1/1980 | Rose et al. |
| 4,823,985 A | 4/1989 | Grollier et al. |
| 4,933,355 A | 6/1990 | Yoshioka et al. |
| 5,061,289 A | 10/1991 | Clausen et al. |
| 5,132,412 A | 7/1992 | Hansen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Löwe et al. |
| 5,892,046 A | 4/1999 | Grund et al. |
| 6,099,592 A | 8/2000 | Vidal et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,730,789 B1 | 5/2004 | Birault et al. |
| 2002/0050013 A1 | 5/2002 | Vidal et al. |
| 2003/0013041 A1 | 1/2003 | Berneth et al. |
| 2003/0019051 A9 | 1/2003 | Vidal et al. |
| 2003/0093867 A1 | 5/2003 | Chassot et al. |
| 2004/0107512 A1 | 6/2004 | Samain et al. |
| 2004/0231064 A1 | 11/2004 | Umbricht et al. |
| 2008/0189878 A1 | 8/2008 | Plos |
| 2009/0265865 A1 | 10/2009 | Lockridge et al. |
| 2010/0162492 A1* | 7/2010 | Hercouet ................. A61K 8/37 8/416 |
| 2014/0053346 A1 | 2/2014 | Lagrange et al. |

FOREIGN PATENT DOCUMENTS

| DE | 2359399 A1 | 6/1975 |
| DE | 3843892 A1 | 6/1990 |
| DE | 4133957 A1 | 4/1993 |
| DE | 19543988 A1 | 5/1997 |
| EP | 0327221 A1 | 8/1989 |

(Continued)

OTHER PUBLICATIONS

STIC Search Report dated May 8, 2017.*
International Search Report for Application No. PCT/EP2015/060642, dated Sep. 18, 2015.
International Search Report for related Application No. PCT/EP2015/060637, dated Jul. 22, 2015.
Todd, Charles, et al., "Volatile Silicone Fluids for Cosmetic Formulations," Cosmetics and Toiletries, vol. 91, Jan. 1976, pp. 29-32.
English language Abstract for EP 0770375 (May 2, 1997).
English language Abstract for EP 1498109 (Jan. 19, 2005).
English language Abstract for JP 02-019576 (Jan. 23, 1990).
English language Abstract for JP 05-163124 (Jun. 29, 1993).

*Primary Examiner* — Eisa B Elhilo
(74) *Attorney, Agent, or Firm* — The Marbury Law Group, PLLC

(57) ABSTRACT

The invention relates to a composition comprising: i) at least one oxidation base, preferably of heterocyclic and/or para-phenylenediamine type; and ii) at least one heteroaryl coupler of formula (I), with $R^1$, $R^2$, $R^3$, A and X as defined in the description. The invention also relates to a process for dyeing keratin fibres using ingredients i) and ii); to a kit comprising ingredients i) and ii); and to the use of ingredient i) combined with ii) for dyeing keratin fibres. The composition of the invention leads to particularly powerful, chromatic and sparingly selective colourings.

(I)

23 Claims, No Drawings

(56) References Cited

FOREIGN PATENT DOCUMENTS

| | | |
|---|---|---|
| EP | 0770375 A1 | 5/1997 |
| EP | 1498109 A1 | 1/2005 |
| FR | 2586913 A1 | 3/1987 |
| FR | 2733749 A1 | 11/1996 |
| FR | 2801308 A1 | 5/2001 |
| FR | 2974509 A1 | 11/2012 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 96/15765 A1 | 5/1996 |
| WO | 02/080160 A1 | 10/2002 |
| WO | 03/063809 A2 | 8/2003 |
| WO | 2005/014591 A1 | 2/2005 |
| WO | 2008/149005 A2 | 12/2008 |
| WO | 2010/133640 A2 | 11/2010 |
| WO | 2015/173322 A1 | 11/2015 |

\* cited by examiner

COMPOSITION FOR DYEING KERATIN FIBRES, COMPRISING AN OXIDATION BASE AND A PARTICULAR HETEROARYL COUPLER

CROSS REFERENCE TO RELATED APPLICATIONS

This is a national stage application of PCT/EP2015/060642, filed internationally on May 13, 2015, which claims priority to French Application No. 1454407, filed on May 16, 2014, both of which are incorporated by reference herein in their entireties.

The invention relates to a composition comprising i) at least one oxidation base, preferably of heterocyclic and/or para-phenylenediamine type, ii) at least one particular heteroaryl coupler, preferably aminothiazole; to a process for dyeing keratin fibres using ingredients i) and ii); to a kit comprising ingredients i) and ii) and to the use of ingredient i) combined with ii) for dyeing keratin fibres.

Many people have sought for a long time to modify the colour of their hair and in particular to mask their grey hair.

It is known practice to dye keratin fibres, in particular human keratin fibres such as the hair, to obtain "permanent" colourings with dye compositions containing oxidation dye precursors, which are generally known as oxidation bases, such as ortho- or para-phenylenediamines, ortho- or para-aminophenols, or heterocyclic compounds such as pyrazoles, pyrazolinones or pyrazolo-pyridines. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colouring modifiers, the latter being chosen especially from aromatic meta-diamines, meta-aminophenols, meta-diphenols and certain heterocyclic compounds such as indole or pyridine compounds. The variety of molecules used as oxidation bases and couplers allows a wide range of colours to be obtained.

The oxidation dyeing process thus consists in applying to keratin fibres a dye composition comprising oxidation bases or a mixture of oxidation bases and couplers with hydrogen peroxide as oxidizing agent, in leaving it to diffuse, and then in rinsing the fibres.

However, the use of these dye compositions may have a certain number of drawbacks. Specifically, after application to keratin fibres, the dyeing power obtained may not be entirely satisfactory, or may even be weak, and lead to a restricted range of colours. The colourings may also not be sufficiently persistent with respect to external agents such as light, shampoo or perspiration, and may also be too selective, i.e. the difference in colouring is too great along the same keratin fibre that is differently sensitized between its end and its root.

Thiazole compounds have been used in the synthesis of (azo)methine dyes that are heat-transferable onto synthetic materials (see, for example, U.S. Pat. No. 5,892,046) or laser frequency-doubling dyes (see, for example, WO 02080160).

Certain thiophene derivatives are known to give the hair body (WO 2003/063 809). 2-Aminofuran derivatives have also been used for oxidation dyeing (EP 1 498 109). The latter derivatives do not always give satisfactory colourings on keratin fibres, especially in terms of the colour build-up on the fibre or in terms of selectivity.

One of the objects of the present invention is especially to propose compositions for dyeing keratin fibres, in particular human keratin fibres such as the hair, which are especially capable of leading to a wide range of colours with powerful, sparingly selective colourings that are resistant to external agents (such as shampoo, light, perspiration or bad weather).

This aim is achieved by the present invention, one subject of which is especially a composition for dyeing keratin fibres, in particular human keratin fibres such as the hair, comprising:

i) at least one oxidation base;
ii) at least one heteroaryl coupler of formula (I):

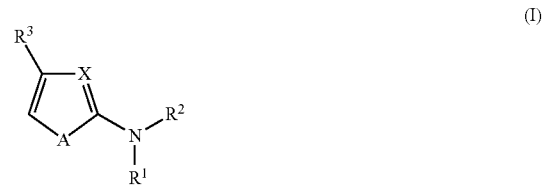

and also addition salts thereof with an organic or mineral acid or base, optical or geometrical isomers thereof, tautomers thereof or solvates thereof such as hydrates, in which compound of formula (I):

A represents oxygen or sulfur atoms, preferably sulfur;
X represents a nitrogen atom or a group C—$R^4$;
$R^1$ and $R^2$, which may be identical or different, represent i) a linear or branched ($C_1$-$C_4$) alkyl group, optionally interrupted with one or more heteroatoms, and optionally hydrogenated or ($C_1$-$C_4$)alkylated, and/or optionally substituted, ii) optionally substituted aryl; iii) optionally substituted heteroaryl; iv) optionally substituted (hetero)cycloalkyl; or alternatively $R^1$ and $R^2$ form, together with the nitrogen atom that bears them, an optionally substituted heterocycloalkyl, the ring also possibly comprising one or more heteroatoms chosen from oxygen, sulfur and nitrogen, said heterocycle preferentially being 5- or 6-membered such as morpholino, piperazino or piperidino;
$R^3$ and $R^4$, which may be identical or different, represent i) a linear or branched ($C_1$-$C_4$) alkyl group, optionally interrupted with one or more heteroatoms, and optionally hydrogenated or ($C_1$-$C_4$)alkylated, and/or optionally substituted with one or more groups; ii) optionally substituted aryl; iii) optionally substituted heteroaryl or iv) optionally substituted (hetero)cycloalkyl.

A subject of the invention is also a dyeing process using this composition.

Another subject of the invention is the use of the compounds of formula (I) for the oxidation dyeing of keratin fibres, in particular human keratin fibres such as the hair.

The composition of the invention leads to particularly powerful, chromatic and sparingly selective colourings. Furthermore, the colour build-up on keratin fibres treated with the composition of the invention is very satisfactory. The composition also makes it possible to obtain dye compositions leading to colourings that are very resistant to the various attacking factors to which the hair may be subjected, such as light, bad weather, washing and perspiration. The oxidation dye compositions in accordance with the invention also make it possible to achieve shades in a very broad range of colours.

For the purposes of the present invention, the term "build-up" of the colour of the keratin fibres means the variation in colouring between locks of non-dyed grey hair and locks of dyed hair.

Other subjects, characteristics, aspects and advantages of the present invention will emerge even more clearly on reading the description and the examples that follow.

In the text hereinbelow, and unless otherwise indicated, the limits of a range of values are included within that range.

The expression "at least one" is equivalent to the expression "one or more".

the term "optionally substituted" after the expressions "aryl" or "heteroaryl", "cycloalkyl", "heterocyclic" or "heterocycloalkyl" implies that said ring may be substituted with at least one atom or group chosen from:

halogen such as chlorine, fluorine or bromine;

$C_1$-$C_8$ and preferably $C_1$-$C_6$ alkyl optionally substituted with one or more radicals chosen from hydroxyl, $C_1$-$C_2$ alkoxy, $C_2$-$C_4$ (poly)hydroxyalkoxy, acylamino, carboxyl, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;

hydroxyl, $C_1$-$C_2$ alkoxy;

$C_2$-$C_4$ (poly)hydroxyalkoxy;

amino;

nitro, nitroso or cyano;

5- or 6-membered heterocycloalkyl;

aryl such as phenyl;

5- or 6-membered heteroaryl;

amino substituted with one or two identical or different $C_1$-$C_6$ alkyl radicals optionally bearing at least:
  i) one hydroxyl group,
  ii) one amino group optionally substituted with one or two optionally substituted $C_1$-$C_3$ alkyl radicals, said alkyl radicals possibly forming, with the nitrogen atom to which they are attached, a saturated or unsaturated, optionally substituted 5- to 7-membered heterocycle, optionally comprising at least one other nitrogen or non-nitrogen heteroatom;

acylamino (—N(R)—C(X)R') in which the radical R is a hydrogen atom or a $C_1$-$C_4$ alkyl radical optionally bearing at least one hydroxyl group and the radical R' is a $C_1$-$C_2$ alkyl radical, with X representing oxygen, sulfur or NR with R as defined previously, preferably X=O;

carbamoyl ((R)$_2$N—C(X)—) in which the radicals R, which may be identical or different, represent a hydrogen atom or a $C_1$-$C_4$ alkyl radical optionally bearing at least one hydroxyl group, with X representing oxygen, sulfur or NR with R as defined previously, preferably X=O;

carboxyl or ester, (—O—C(O)R") or (—C(O)OR"), in which the radical R" is a hydrogen atom or a $C_1$-$C_4$ alkyl radical optionally bearing at least one hydroxyl group, and the radical R" is a $C_1$-$C_2$ alkyl radical; the carboxyl radical possibly being in acid or salified form (preferably with an alkali metal or a substituted or unsubstituted ammonium);

alkylsulfonylamino (R'S(O)$_2$—N(R)—) in which the radical R represents a hydrogen atom or a $C_1$-$C_4$ alkyl radical optionally bearing at least one hydroxyl group and the radical R' represents a $C_1$-$C_4$ alkyl radical, or a phenyl radical;

aminosulfonyl ((R)$_2$N—S(O)$_2$—), or heteroarylsulfonyl (R'''—S(O)$_2$—) in which the radicals R, which may be identical or different, represent a hydrogen atom or a $C_1$-$C_4$ alkyl radical optionally bearing at least one hydroxyl group and R''' represents an unsubstituted 5- or 6-membered heteroaryl such as thiophenyl or furyl;

—SO$_3$H;

(poly)haloalkyl, preferentially trifluoromethyl (CF$_3$);

a (hetero)cyclic or (hetero)cycloalkyl radical or a non-aromatic part of an (hetero)aryl radical may also be substituted with one or more oxo groups;

an "aryl" radical represents a monocyclic or fused or non-fused polycyclic hydrocarbon-based group comprising from 6 to 22 carbon atoms, at least one ring of which is aromatic; the aryl radical is in particular a phenyl, biphenyl, naphthyl, indenyl, anthracenyl or tetrahydronaphthyl and more preferentially phenyl;

a "heteroaryl" radical represents a 5- to 22-membered, monocyclic or fused or non-fused polycyclic group, comprising from 1 to 6 heteroatoms chosen from nitrogen, oxygen, sulfur and selenium atoms, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthyl and the ammonium salt thereof;

a "cycloalkyl" radical is a non-aromatic, monocyclic or fused or non-fused polycyclic hydrocarbon-based radical containing from 5 to 22 carbon atoms, which may comprise one or more unsaturations, such as cyclohexyl or cyclopentyl;

a "heterocycloalkyl" radical is a non-aromatic, saturated, monocyclic or fused or non-fused polycyclic 5- to 22-membered radical, comprising from 1 to 6 heteroatoms chosen from nitrogen, oxygen, sulfur and selenium atoms, morpholinyl, thiomorpholinyl, piperidyl, piperazinyl, pyrrolidinyl, tetrahydrofuryl, tetrahydrothiophenyl, azepanyl, thioazepanyl; preferentially morpholino;

an "alkyl" radical is a linear or branched $C_1$-$C_8$, preferably $C_1$-$C_6$ and particularly $C_1$-$C_4$ hydrocarbon-based radical, such as methyl or ethyl;

the term "optionally substituted" attributed to the alkyl radical means that said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming, with the nitrogen atom that bears them, a 5- to 7-membered heterocycle, optionally comprising another nitrogen or non-nitrogen heteroatom, v) phenyl, vi) ($C_1$-$C_6$)alkoxycarbonyl, vii) ($C_1$-$C_6$)alkylcarbonyloxy, viii) H—C(O)—O—;

an "alkoxy" radical is an alkyl-oxy or alkyl-O— radical for which the alkyl radical is a linear or branched $C_1$-$C_{16}$ and preferentially $C_1$-$C_8$ hydrocarbon-based radical; particularly $C_1$-$C_4$ such as methoxy or ethoxy, and when the alkoxy group is optionally substituted, this means that the alkyl group is optionally substituted as defined above;

a "(poly)haloalkyl" radical is an "alkyl" radical as defined previously, in which one or more hydrogen atoms are substituted or replaced with one or more halogen atoms such as the fluorine, chlorine or bromine atom; a polyhaloalkyl that may be mentioned is the trifluoromethyl group;

an "alkylthio" radical is an alkyl-S— radical for which the alkyl radical is a linear or branched $C_1$-$C_8$ and preferentially $C_1$-$C_6$ hydrocarbon-based radical; particularly $C_1$-$C_4$ such as methylthio or ethylthio, and when the alkylthio group is optionally substituted, this means that the alkyl group is optionally substituted as defined above;

an anionic counterion is organic or mineral, preferentially chosen from halide anions such as $Cl^-$, $Br^-$ or $I^-$, and organic anions such as mesylates.

Furthermore, unless otherwise indicated, the limits delimiting the extent of a range of values are included in this range of values.

In general, the term "addition salts" of compounds means the addition salts of these compounds either with an acid, such as hydrochlorides, hydrobromides, sulfates, citrates, succinates, tartrates, lactates, tosylates, benzenesulfonates, dodecylbenzenesulfonates, phosphates and acetates, and preferably the hydrochlorides, citrates, succinates, tartrates, phosphates and lactates, or the addition salts of these compounds with an alkaline agent, such as an alkali metal or alkaline-earth metal hydroxide or (bi)carbonate, ammonia, or organic amines and in particular alkanolamines.

The solvates of compounds more particularly represent the hydrates of such compounds and/or the combination of such compounds with a linear or branched $C_1$-$C_4$ alcohol such as methanol, ethanol, isopropanol or n-propanol. Preferably, the solvates are hydrates.

The composition of the present invention is particularly useful for the oxidation dyeing of keratin fibres, in particular of human keratin fibres.

i) The Oxidation Base(s):

The composition of the invention comprises one or more oxidation bases i).

In particular, the oxidation bases are chosen from para-phenylenediamines, bis(phenyl)alkylenediamines, para-aminophenols, ortho-aminophenols and heterocyclic bases, and the addition salts thereof. Preferentially, the oxidation base(s) of the invention are chosen from para-phenylenediamines and heterocyclic bases.

Among the para-phenylenediamines, examples that may be mentioned include para-phenylenediamine, para-tolylenediamine, 2-chloro-para-phenylenediamine, 2,3-dimethyl-para-phenylenediamine, *2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine,N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol, 5-acetamido-2-aminophenol and the addition salts thereof.

Among the heterocyclic bases, mention may be made in particular of pyridine derivatives, pyrimidine derivatives and pyrazole derivatives.

Among the pyridine derivatives, examples that may be mentioned include the compounds described in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof, described, for example, in patent application FR 2 801 308.

Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and the addition salts thereof.

More particularly, the oxidation bases according to the invention are chosen from 3-aminopyrazolo[1,5-a]pyridines preferably substituted in position 2 with:
a) a (di)($C_1$-$C_6$)(alkyl)amino group, the alkyl groups possibly being substituted with one or more hydroxyl, amino or imidazolium groups;
b) a cationic or non-cationic 5- to 7-membered heterocycloalkyl group comprising from 1 to 3 heteroatoms, optionally substituted with one or more ($C_1$-$C_6$)alkyl groups such as di($C_1$-$C_4$)alkylpiperazinium;
c) a ($C_1$-$C_6$)alkoxy group optionally substituted with one or more hydroxyl groups, such as β-hydroxyalkoxy, and also the addition salts thereof.

Among the pyrimidine derivatives, mention may be made of the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives, mention may be made of the compounds described in patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triamino-pyrazole, 1-methyl-3,4,5-triaminopyrazole, 3,5-diamino-1-methyl-4-methylaminopyrazole, 3,5-diamino-4-(βhydroxyethyl)amino-1-methylpyrazole, and the addition salts thereof. Preferably, the heterocyclic oxidation bases of the invention are chosen from 4,5-diaminopyrazoles such as 4,5-diamino-1-(β-hydroxyethyl)pyrazole. Use may also be made of 4,5-diamino-1-(β-methoxyethyl)pyrazole.

The oxidation base(s) present in the composition of the invention are generally present in an amount ranging from 0.001% to 20% by weight, and preferably ranging from 0.005% to 6%, relative to the total weight of the dye composition.

In one variant of the invention, the composition of the invention comprises at least one heterocyclic oxidation base.
ii) The Coupler(s) of Formula (I):

The composition of the invention comprises one or more heteroaryl couplers of formula (I) as defined previously.

Preferentially, the heteroaryl coupler(s) of formula (I) are chosen from the thiazolyl couplers (I'), i.e. they are such that A represents a sulfur atom and X represents a nitrogen atom:

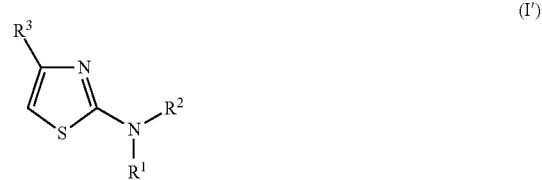

(I')

and also addition salts thereof with an organic or mineral acid or base, optical or geometrical isomers thereof, tautomers thereof or solvates thereof such as hydrates, with $R^1$, $R^2$ and $R^3$ as defined previously.

According to a particular embodiment of the invention, the coupler(s) are such that, in formula (I) or (I'): $R^1$ and $R^2$ represent i) a ($C_1$-$C_6$)alkyl group optionally interrupted with one or more heteroatoms chosen from oxygen, sulfur and nitrogen, preferably with at least one oxygen atom.

According to another advantageous variant of the invention, the coupler(s) are such that, in formula (I) or (I'): $R^1$ and $R^2$ form, together with the nitrogen atom that bears them, an optionally substituted 5- or 6-membered, preferably 6-membered, heterocycloalkyl group, such as morpholino, piperazino or piperidino, particularly morpholino.

According to a particular embodiment of the invention, the coupler(s) are such that, in formula (I) or (I'): $R^3$ represents i) a ($C_1$-$C_6$)alkyl group which is optionally substituted, preferably with at least one hydroxyl group; ii) an optionally substituted aryl group such as phenyl; or iii) an optionally substituted 5- or 6-membered, preferably 6-membered, heterocycloalkyl, such as morpholino, piperazino or piperidino, particularly morpholino.

Among the compounds of formula (I) or (I'), examples that may be mentioned include the following compounds:

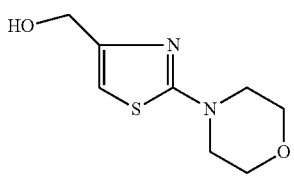

1
126533-98-8
(2-Morpholin-4-yl-
thiazol-4-yl)methanol

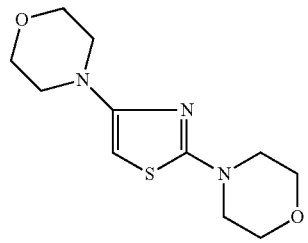

2
169195-54-4
4,4'-(2,4-
thiazolediyl)bis

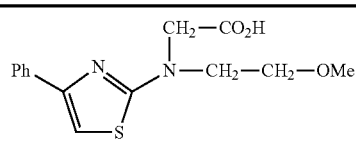

1303757-32-5
Glycine, N-(2-methoxyethyl)-
N-(4-phenyl-2-thiazolyl)

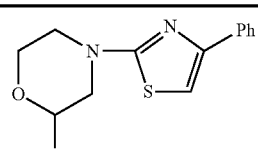

1291897-04-5
2-Morpholinecarboxylic
acid, 4-(4-phenyl-2-
thiazolyl)-

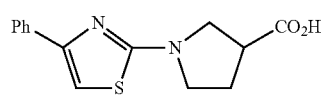

1282558-49-9
3-Pyrrolidinecarboxylic acid,
1-(4-phenyl-2-thiazolyl)-

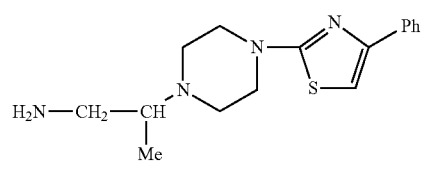

1282507-44-1
1-Piperazineethanamine, 1-
methyl-4-(4-phenyl-2-
thiazolyl)-

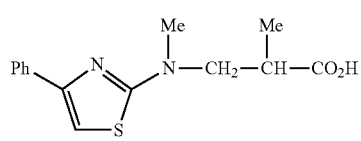

1270783-46-4
Propanoic acid, 2-methyl-3-
[methyl(4-phenyl-2-thiazolyl)
amino]-

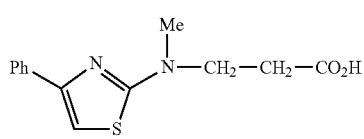

1184823-99-1
β-Alanine, N-methyl-N-(4-
phenyl-2-thiazolyl)-

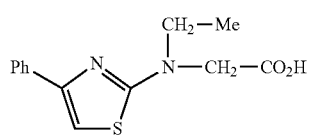

1179899-35-4
Glycine, N-ethyl-N-(4-phenyl-
2-thiazolyl)-

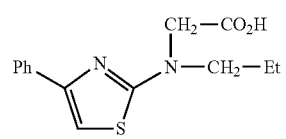

1179266-55-7
Glycine, N-(4-phenyl-2-
thiazolyl)-N-propyl

-continued

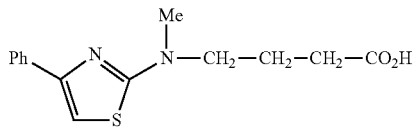

1156152-39-4
Butanoic acid, 4-[methyl(4-phenyl-2-thiazolyl)amino]-

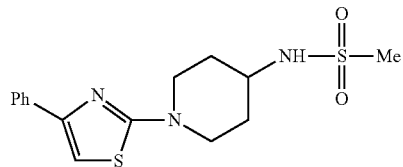

943337-52-8
Methanesulfonamide, N-[1-(4-phenyl-2-thiazolyl)-4-piperidinyl]-

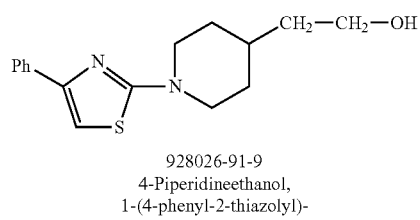 [SMILES: OCCC1CCN(c2nc(-c3ccccc3)cs2)CC1]

928026-91-9
4-Piperidineethanol, 1-(4-phenyl-2-thiazolyl)-

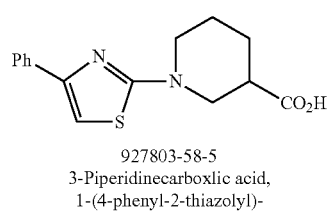 [SMILES: O=C(O)C1CCCN(c2nc(-c3ccccc3)cs2)C1]

927803-58-5
3-Piperidinecarboxlic acid, 1-(4-phenyl-2-thiazolyl)-

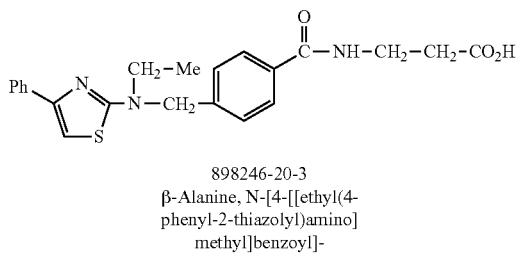 [SMILES: CCN(Cc1ccc(C(=O)NCCC(=O)O)cc1)c1nc(-c2ccccc2)cs1]

898246-20-3
β-Alanine, N-[4-[[ethyl(4-phenyl-2-thiazolyl)amino]methyl]benzoyl]-

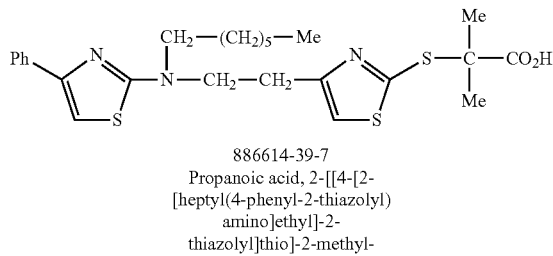

886614-39-7
Propanoic acid, 2-[[4-[2-[heptyl(4-phenyl-2-thiazolyl)amino]ethyl]-2-thiazolyl]thio]-2-methyl-

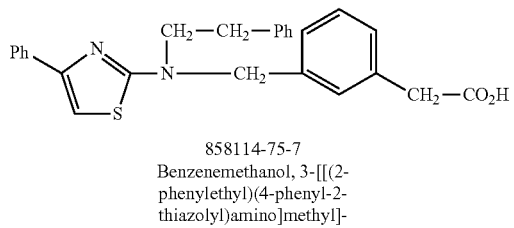 [SMILES: O=C(O)Cc1cccc(CN(CCc2ccccc2)c2nc(-c3ccccc3)cs2)c1]

858114-75-7
Benzenemethanol, 3-[[(2-phenylethyl)(4-phenyl-2-thiazolyl)amino]methyl]-

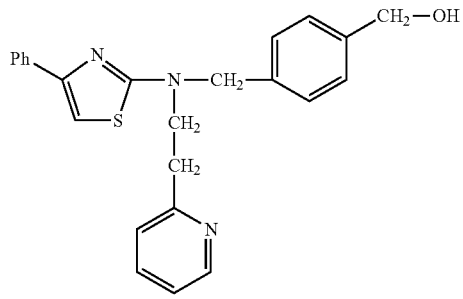

858114-71-3
Benzenemethanol, 4-[[(4-phenyl-2-thiazolyl)[2-(2-pyridinyl)ethyl]amino]methyl]-

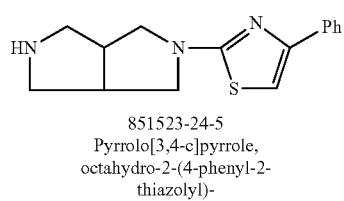 [SMILES: c1ccc(-c2csc(N3CC4CNCC4C3)n2)cc1]

851523-24-5
Pyrrolo[3,4-c]pyrrole, octahydro-2-(4-phenyl-2-thiazolyl)-

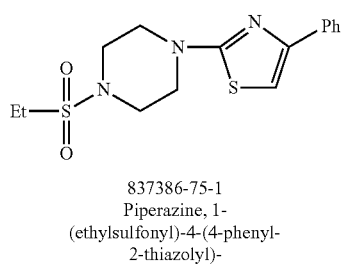 [SMILES: CCS(=O)(=O)N1CCN(c2nc(-c3ccccc3)cs2)CC1]

837386-75-1
Piperazine, 1-(ethylsulfonyl)-4-(4-phenyl-2-thiazolyl)-

-continued

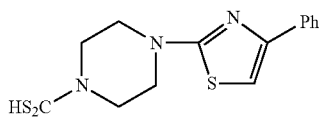

743372-21-6
1-Piperazinecarbodithioic
acid, 4-(4-phenyl-2-thiazolyl)-

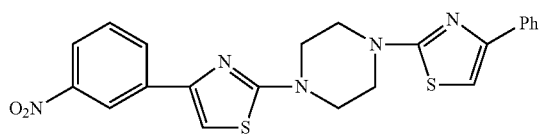

696633-56-4
Piperazine, 1-[4-(3-
nitrophenyl)-2-thiazolyl]-4-
(4-phenyl-2-thiazolyl)-

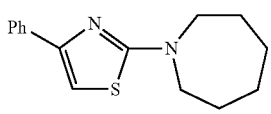

695160-01-1
1H-Azepine, hexahydro-1-(4-
phenyl-2-thiazolyl)-

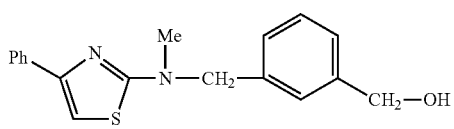

691904-94-6
Benzenemethanol, 3-
[[methyl(4-phenyl-2-
thiazolyl)amino]methyl]-

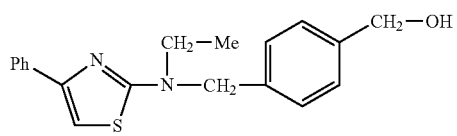

691904-86-6
Benzenemethanol, 4-[[ethyl(4-
phenyl-2-
thiazolyl)amino]methyl]-

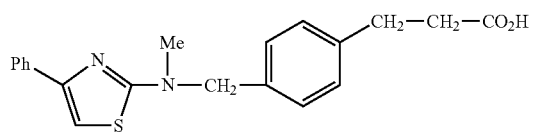

691903-92-1
Benzenepropanoic acid, 4-
[[methyl(4-phenyl-2-
thiazolyl)amino]methyl]-

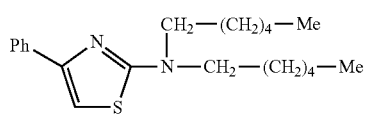

480999-15-3
2-Thiazolamine, N,N-dihexyl-
4-phenyl-

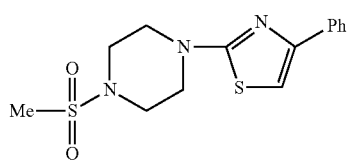

447428-28-6
Piperazine, 1-
(methylsulfonyl)-4-(4-
phenyl-2-thiazolyl)-

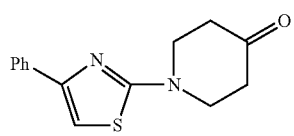

392643-02-6
1-(4-Phenyl-1,3-thiazol-2-yl)-
4-piperidinone

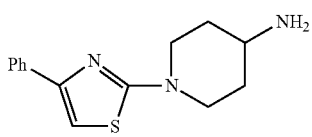

380828-82-0
1-[1-(4-Phenyl-2-thiazolyl)-
4-piperidinyl]amine

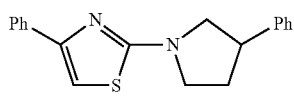

345990-58-1
Thiazole, 4-phenyl-2-(3-
phenyl-1-pyrrolidinyl)-

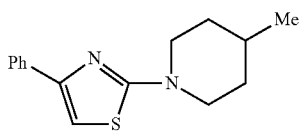

345990-52-5
Piperidine, 4-methyl-1-(4-
phenyl-2-thiazolyl)-

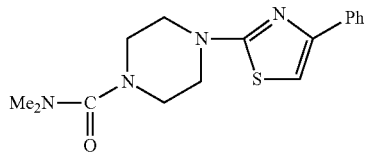

309734-77-8
1-Piperazinecarboxamide,
N,N-dimethyl-4-(4-phenyl-2-
thiazolyl)-

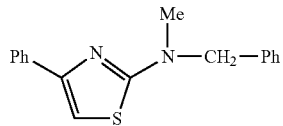

309732-99-8
2-Thiazolamine, N-methyl-
4-phenyl-N-(phenylmethyl)-

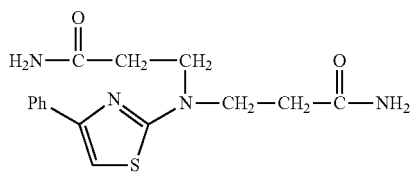

300686-24-2
Propanamide, 3,3'-[(4-phenyl-
2-thiazolyl)imino]bis-

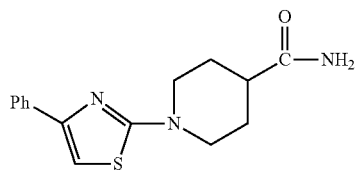

299922-31-9
4-Piperidinecarboxamide,
1-(4-phenyl-2-thiazolyl)-

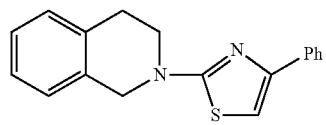

299922-22-8
Isoquinoline, 1,2,3,4-
tetrahydro-2-(4-phenyl-2-
thiazolyl)-

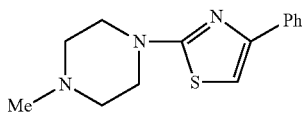

231963-95-4
Piperazine, 1-methyl-4-(4-
phenyl-2-thiazolyl)-

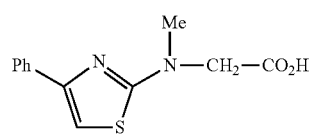

141115-10-8
Glycine, N-methyl-N-(4-
phenyl-2-thiazolyl)-

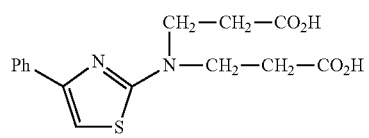

138537-78-7
β-Alanine, N-(2-
carboxyethyl)-N-(4-phenyl-
2-thiazolyl)-

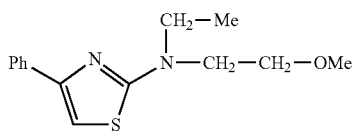

133694-26-5
2-Thiazolamine, N-ethyl-N-(2-
methoxyethyl)-4-phenyl-

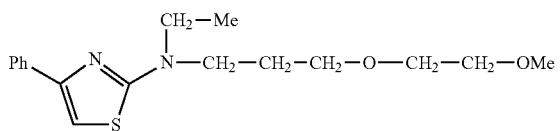

133694-24-3
2-Thiazolamine, N-ethyl-N-
[3-(2-
methoxyethoxy)propyl]-4-phenyl

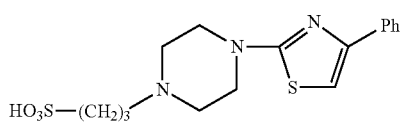

132292-90-1
1-Piperazinepropanesulfonic
acid, 4-(4-phenyl-2-thiazolyl)-

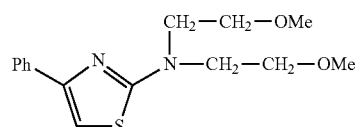

130531-64-5
2-Thiazolamine, N,N-bis(2-
methoxyethyl)-4-phenyl-

-continued

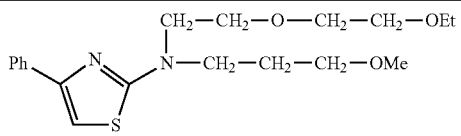

129719-95-5
2-Thiazolamine, N-[2-(2-ethoxyethoxy)ethyl]-N-(3-methoxypropyl)-4-phenyl-

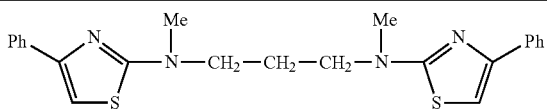

128699-97-8
1,3-Propanediamine, N,N'-dimethyl-N,N'-bis(4-phenyl-2-thiazolyl)-

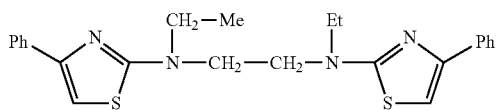

128699-95-6
1,2-Ethanediamine, N,N'-diethyl-N,N'-bis(4-phenyl-2-thiazolyl)-

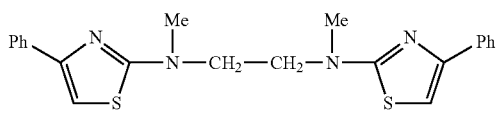

128699-84-3
1,2-Ethanediamine, N,N'-dimethyl-N,N'-bis(4-phenyl-2-thiazolyl-

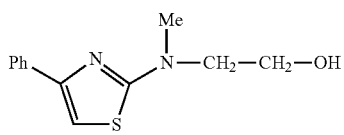

122320-82-5
Ethanol, 2-[methyl(4-phenyl-2-thiazolyl)amino]-

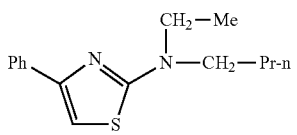

89314-44-3
2-Thiazolamine, N-butyl-N-ethyl-4-phenyl-

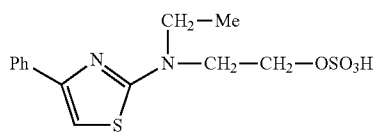

84551-96-2
Ethanol, 2-[ethyl(4-phenyl-2-thiazolyl)amino], 1-(hydrogen sulfate)

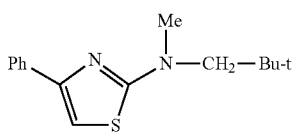

82721-96-8
2-Thiazolamine, N-(2,2-dimethylpropyl)-N-methyl-4-phenyl-

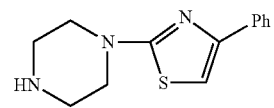

69389-14-6
1-(4-Phenyl-2-thiazolyl)piperazine

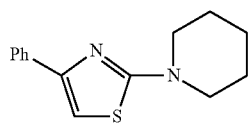

34587-25-2
2-Piperidino-4-phenylthiazole

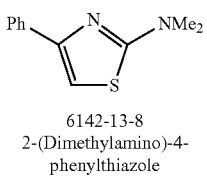 [SMILES: CN(C)c1nc(-c2ccccc2)cs1]

6142-13-8
2-(Dimethylamino)-4-phenylthiazole

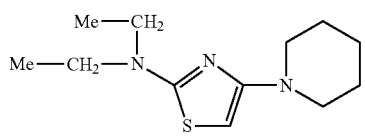 [SMILES: CCN(CC)c1nc(N2CCCCC2)cs1]

2-Thiazolamine, N,N-diethyl-4-(1-piperidinyl)-
192332-28-8

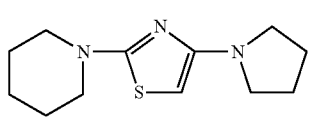 [SMILES: c1sc(N2CCCCC2)nc1N1CCCC1]

192332-24-4 Piperidine, 1-[4-(1-pyrrolidinyl)-2-thiazolyl]-

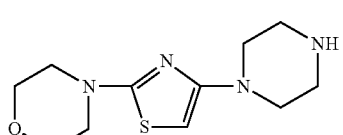

Morpholine, 4-[4-(1-piperazinyl)-2-thiazolyl]-
192332-20-0

-continued

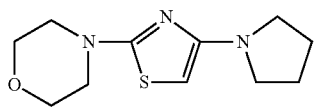

Morpholine, 4-[4-(1-pyrrolidinyl)-2-thiazolyl]-
170492-35-0

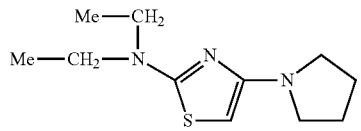

2-Thiazolamine, N,N-diethyl-4-(1-pyrrolidinyl)-
170492-33-8

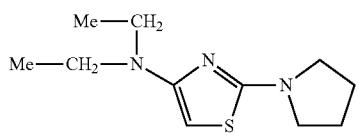 [SMILES: CCN(CC)c1csc(N2CCCC2)n1]

4-Thiazolamine, N,N-diethyl-2-(1-pyrrolidinyl)-170492-26-9

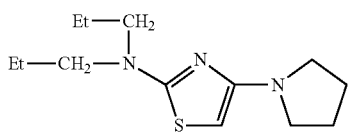 [SMILES: CCCN(CCC)c1nc(N2CCCC2)cs1]

2-Thiazolamine, N,N-dipropyl-4-(1-pyrrolidinyl)-
169195-69-1

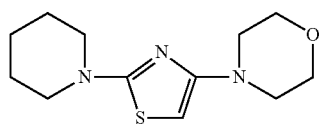 [SMILES: c1sc(N2CCCCC2)nc1N1CCOCC1]

Morpholine, 4-[2-(1-piperidinyl)-4-thiazolyl]-
169195-65-7

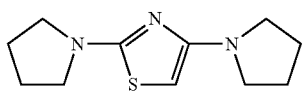 [SMILES: c1sc(N2CCCC2)nc1N1CCCC1]

Thiazole, 2,4-di-1-pyrrolidinyl-169195-63-5

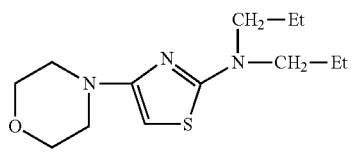

2-Thiazolamine, 4-(4-morpholinyl)-N,N-dipropyl-
169195-57-7

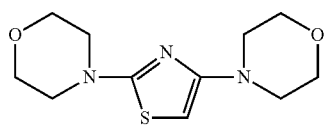 [SMILES: c1sc(N2CCOCC2)nc1N1CCOCC1]

Morpholine, 4,4'-(2,4-thiazolediyl)bis- 169195-54-4

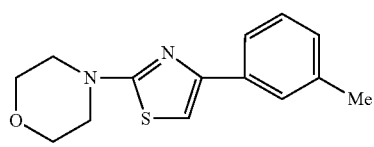 [SMILES: Cc1cccc(-c2csc(N3CCOCC3)n2)c1]

1427988-09-7
Morpholine, 4-[4-(3-methylphenyl)-2-thiazolyl]-

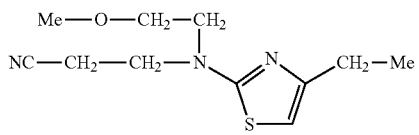

1409712-48-6
Propanenitrile, 3-[(4-ethyl-2-thiazolyl)(2-methoxyethyl)amino]-

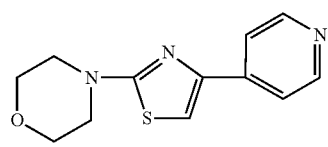 [SMILES: c1cc(-c2csc(N3CCOCC3)n2)ccn1]

1400302-74-0
Morpholine, 4-[4-(4-pyridinyl)-2-thiazolyl]-

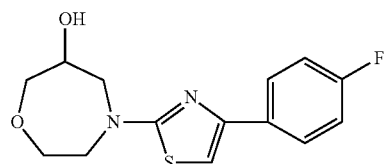

1394469-80-7
1,4-Oxazepin-6-ol, 4-[4-(4-fluorophenyl)-2-thiazolyl]hexahydro-

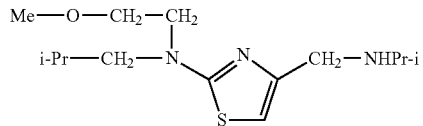

1379280-95-1
4-Thiazolemethanamine, 2-[(2-methoxyethyl)(2-methylpropyl)amino]-N-(1-methylethyl)-

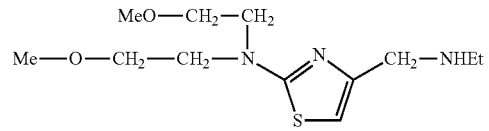

1379276-38-6
4-Thiazolemethanamine, 2-[bis(2-methoxyethyl)amino]-N-ethyl-

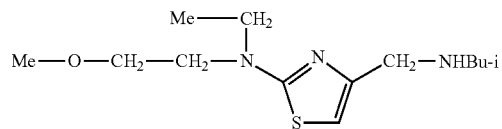

1378904-98-3
4-Thiazolemethanamine, 2-[ethyl(2-methoxyethyl)amino]-N-(2-methylpropyl)-

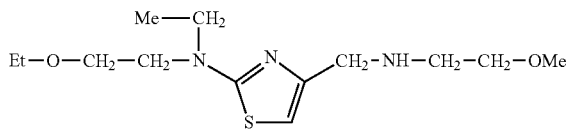

1378757-36-8
4-Thiazolemethanamine, 2-[(2-ethoxyethyl)ethylamino]-N-(2-methoxyethyl)-

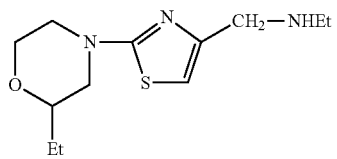

1378597-70-6
4-Thiazolemethanamine, N-ethyl-2-(2-ethyl-4-morpholinyl)-

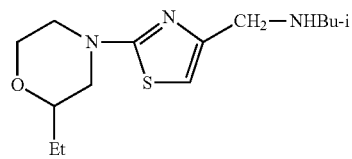

1378435-11-0
4-Thiazolemethanamine, 2-(2-ethyl-4-morpholinyl)-N-(2-methylpropyl)-

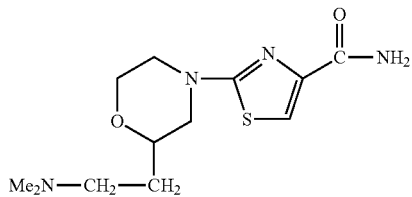

1351040-73-7
4-Thiazolecarboxamide, 2-[2-[2-(dimethylamino)ethyl]-4-morpholinyl]-

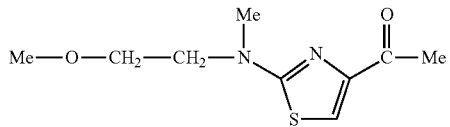 [SMILES: COCCN(C)c1nc(C(C)=O)cs1]

1343822-98-9
Ethanone, 1-[2-[(2-methoxyethyl)methylamino]-4-thiazolyl]-

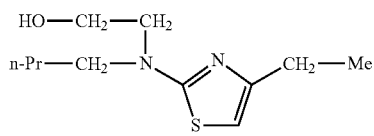

1343133-67-4
Ethanol, 2-[butyl(4-ethyl-2-thiazolyl)amino]-

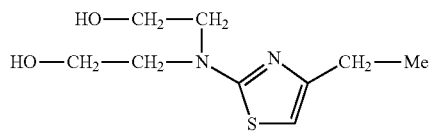

1342615-02-4
Ethanol, 2,2'-[(4-ethyl-2-thiazolyl)imino]bis-

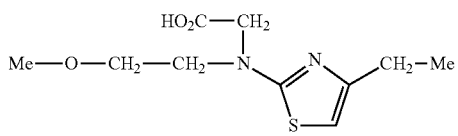

1341439-60-8
Glycine, N-(4-ethyl-2-thiazolyl)-N-(2-methoxyethyl)-

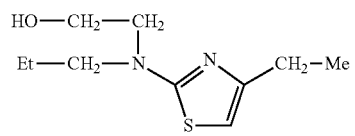 [SMILES: CCCN(CCO)c1nc(CC)cs1]

1339541-62-6
Ethanol, 2-[(4-ethyl-2-thiazolyl)propylamino]-

-continued

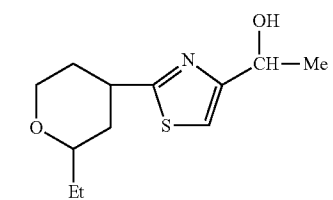

1339205-39-8
4-Thiazolemethanol, 2-(2-ethyl-4-morpholinyl)-α-methyl-

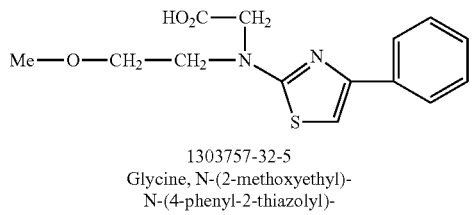

1303757-32-5
Glycine, N-(2-methoxyethyl)-N-(4-phenyl-2-thiazolyl)-

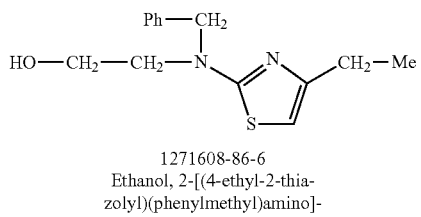

1271608-86-6
Ethanol, 2-[(4-ethyl-2-thiazolyl)(phenylmethyl)amino]-

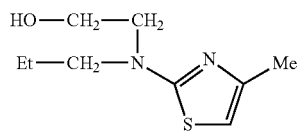

1250660-05-9
Ethanol, 2-[(4-methyl-2-thiazolyl)propylamino]-

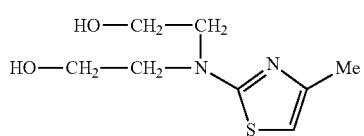

1247143-32-3
Ethanol, 2,2'-[(4-methyl-2-thiazolyl)imino]bis-

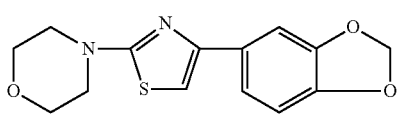 [SMILES: c1cc2c(cc1-c1csc(N3CCOCC3)n1)OCO2]

1013299-22-3
Morpholine, 4-[4-(1,3-benzodioxol-5-yl)-2-thiazolyl]-

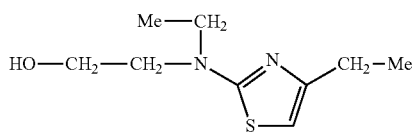

1339133-79-7
Ethanol, 2-[ethyl(4-ethyl-2-thiazolyl)amino]-

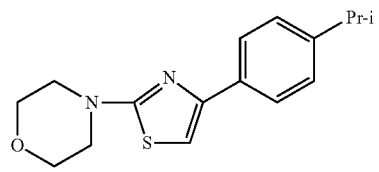

1286070-28-7
Morpholine, 4-[4-[4-(1-methylethyl)phenyl]-2-thiazolyl]-

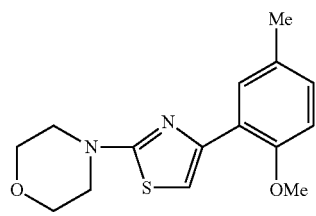

1252154-09-8
Morpholine, 4-[4-(2-methoxy-5-methylphenyl)-2-thiazolyl]-

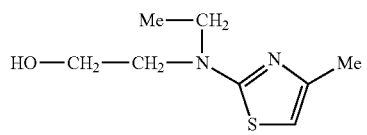

1249721-04-7
Ethanol, 2-[ethyl(4-methyl-2-thiazolyl)amino]-

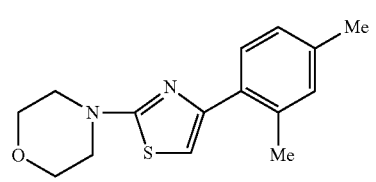

1136631-38-3
Morpholine, 4-[4-(2,4-dimethylphenyl)-2-thiazolyl]-

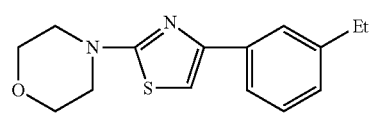

1004719-00-9
Morpholine, 4-[4-(4-ethylphenyl)-2-thiazolyl]-

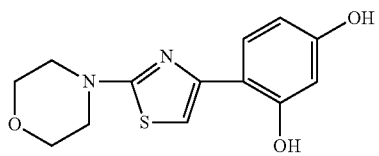 [SMILES: Oc1ccc(-c2csc(N3CCOCC3)n2)c(O)c1]

923850-84-4
1,3-Benzenediol, 4-[2-(4-morpholinyl)-4-thiazolyl]-

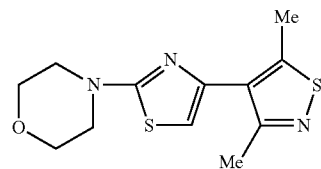

783252-70-0
Morpholine, 4-[4-(3,5-dimethyl-4-isothiazolyl)-2-thiazolyl]-

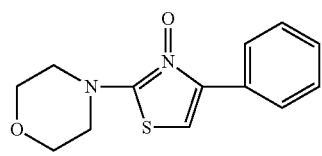 [SMILES: [O-][n+]1c(-c2ccccc2)csc1N1CCOCC1]

746552-23-8
Morpholine, 4-(3-oxido-4-phenyl-2-thiazolyl)-

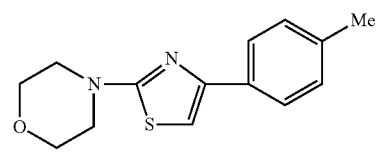 [SMILES: Cc1ccc(-c2csc(N3CCOCC3)n2)cc1]

732975-41-6
Morpholine, 4-[4-(4-methylphenyl)-2-thiazolyl]-

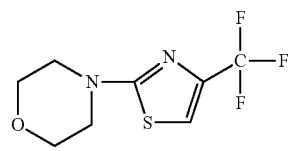 [SMILES: FC(F)(F)c1csc(N2CCOCC2)n1]

265107-02-6
Morpholine, 4-[4-(trifluoromethyl)-2-thiazolyl]-

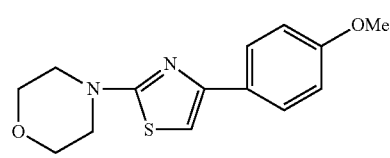 [SMILES: COc1ccc(-c2csc(N3CCOCC3)n2)cc1]

256661-25-3
Morpholine, 4-[4-(4-methoxyphenyl)-2-thiazolyl]-

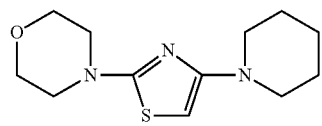 [SMILES: c1sc(N2CCOCC2)nc1N1CCCCC1]

192332-18-6
Morpholine, 4-[4-(1-piperidinyl)-2-thiazolyl]-

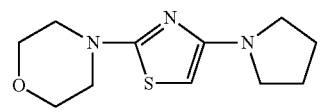 [SMILES: c1sc(N2CCOCC2)nc1N1CCCC1]

170492-35-0
Morpholine, 4-[4-(1-pyrrolidinyl)-2-thiazolyl]-

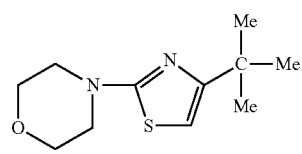 [SMILES: CC(C)(C)c1csc(N2CCOCC2)n1]

164397-09-5
Morpholine, 4-[4-(1,1-dimethylethyl)-2-thiazolyl]-

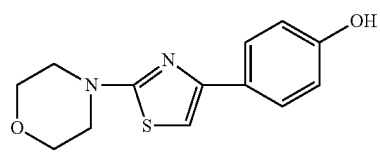 [SMILES: Oc1ccc(-c2csc(N3CCOCC3)n2)cc1]

145889-64-1
Phenol, 4-[2-(4-morpholinyl)-4-thiazolyl]-

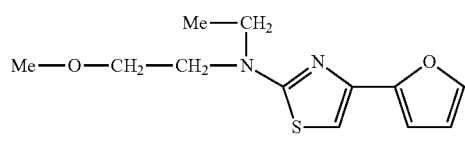

130531-78-1
2-Thiazolamine, N-ethyl-4-(2-furanyl)-N-(2-methoxyethyl)-

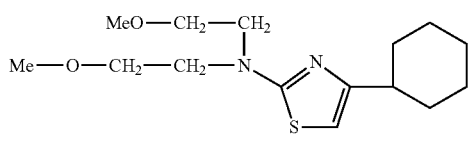

130531-76-9
2-Thiazolamine, 4-cyclohexyl-N,N-bis(2-methoxyethyl)-

-continued

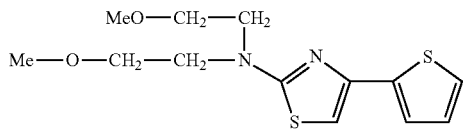 [SMILES: COCCN(CCOC)c1nc(-c2cccs2)cs1]

130531-63-4
2-Thiazolamine, N,N-bis(2-methoxyethyl)-4-(2-thienyl)-

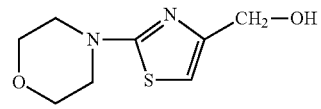

C8H12N2O2S
2-(4-Morpholinyl)-4-(hydroxymethyl)thiazole

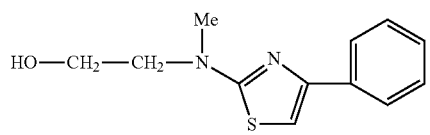 [SMILES: CN(CCO)c1nc(-c2ccccc2)cs1]

122320-82-5
Ethanol, 2-[methyl(4-phenyl-2-thiazolyl)amino]-

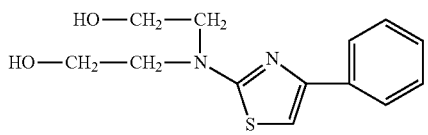

84552-01-2
Ethanol, 2,2'-[(4-phenyl-2-thiazolyl)imino]bis-

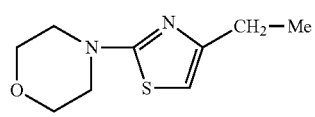 [SMILES: CCc1csc(N2CCOCC2)n1]

41817-60-1
Morpholine, 4-(4-ethyl-2-thiazolyl)-

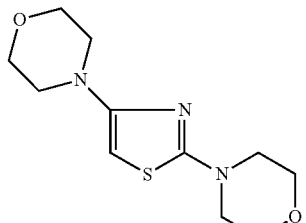

2
169195-54-4
4,4'-(2,4-thiazolediyl)bis

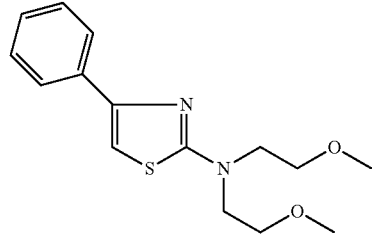 [SMILES: COCCN(CCOC)c1nc(-c2ccccc2)cs1]

3
Bis(2-methoxyethyl)(4-phenylthiazol-2-yl)amine

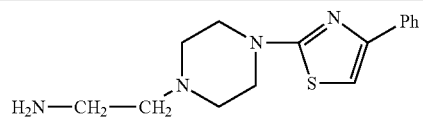

1284733-75-0
1-Piperazineethanamine, 4-(4-phenyl-2-thiazolyl)-

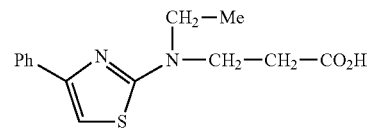

1282370-84-6
1-Piperazinepropanamine, 4-(4-phenyl-2-thiazolyl)-

1183145-57-4
β-Alanine, N-ethyl-N-(4-phenyl-2-thiazolyl)-

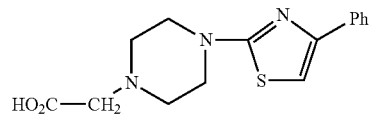
1156376-29-2
1-Piperazineacetic acid, 4-(4-phenyl-2-thiazolyl)-
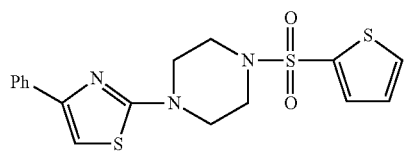 [SMILES: O=S(=O)(c1cccs1)N1CCN(c2nc(-c3ccccc3)cs2)CC1]
933827-86-2
Piperazine, 1-(4-phenyl-2-thiazolyl)-4-(2-thienylsulfonyl)-
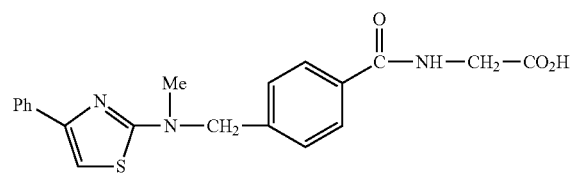
898246-34-9
Glycine, N-[4-[[methyl(4-phenyl-2-thiazolyl)amino]methyl]benzoyl]-
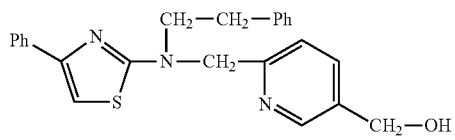
858114-97-3
3-Pyridinemethanol, 6-[[(2-phenylethyl)(4-phenyl-2-thiazolyl)amino]methyl]-
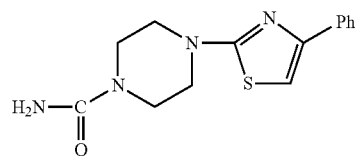 [SMILES: NC(=O)N1CCN(c2nc(-c3ccccc3)cs2)CC1]
857496-78-7
1-Piperazinecarboxamide, 4-(4-phenyl-2-thiazolyl)-
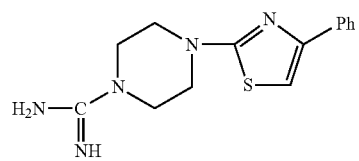 [SMILES: N=C(N)N1CCN(c2nc(-c3ccccc3)cs2)CC1]
775270-75-2
1-Piperazinecarboxamide, 4-(4-phenyl-2-thiazolyl)-

-continued
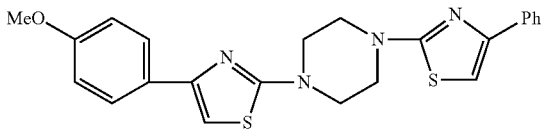
695198-50-6
Piperazine, 1-[4-(4-methoxyphenyl)-2-thiazolyl]-4-(4-phenyl-2-thiazolyl)-
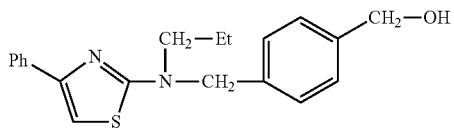
691904-88-8
Benzenemethanol, 4-[[(4-phenyl-2-thiazolyl)propylamino]methyl]-
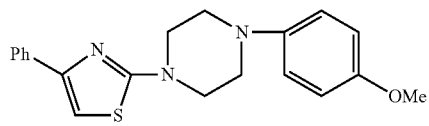
685107-19-1
Piperazine, 1-(4-methoxyphenyl)-4-(4-phenyl-2-thiazolyl)-
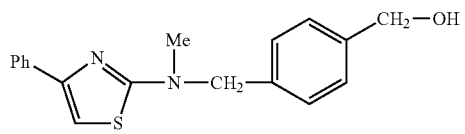 [SMILES: CN(Cc1ccc(CO)cc1)c1nc(-c2ccccc2)cs1]
441357-38-6
4-[Methyl(4-phenyl-2-thiazolyl)aminomethyl] benzyl alcohol
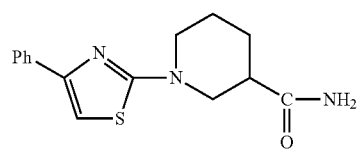 [SMILES: NC(=O)C1CCCN(c2nc(-c3ccccc3)cs2)C1]
346662-46-2
3-Piperidinecarboxamide, 1-(4-phenyl-2-thiazolyl)-
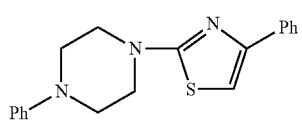
312504-57-7
Piperazine, 1-phenyl-4-(4-phenyl-2-thiazolyl)-
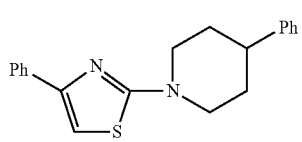 [SMILES: CC1CCN(c2nc(-c3ccccc3)cs2)CC1]
309282-11-9
Piperidine, 4-phenyl-1-(4-phenyl)-2-thiazolyl)-

-continued
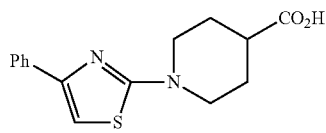 [SMILES: O=C(O)C1CCN(c2nc(-c3ccccc3)cs2)CC1]
299922-24-0
4-Piperidinecarboxylic acid, 1-(4-phenyl-2-thiazolyl)-
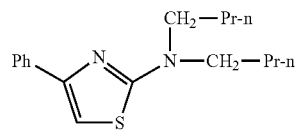
169037-17-6
2-(Dibutylamino)-4-phenylthiazole
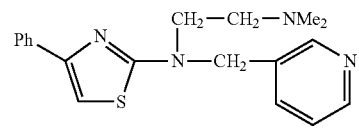 [SMILES: CN(C)CCN(Cc1cccnc1)c1nc(-c2ccccc2)cs1]
136468-43-4
1,2-Ethanediamine, N1,N1-dimethyl-N2-(4-phenyl-2-thiazolyl)-N2-(3-pyridinylmethyl)
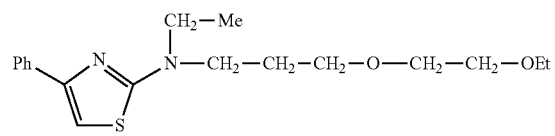
132865-54-4
2-Thiazolamine, N-[3-(2-ethoxyethoxy)propyl]-N-ethyl-4-phenyl
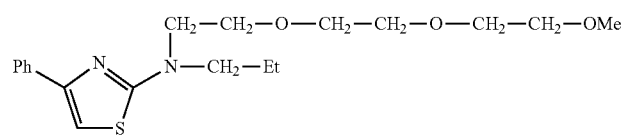
129719-98-8
2-Thiazolamine, N-[2-[2-(2-methoxyethoxy)ethoxy]ethyl]-4-phenyl-N-propyl
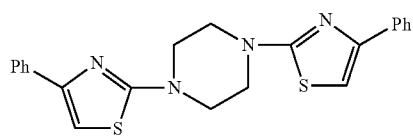
128699-96-7
1,4-Bis(4-phenylthiazol-2-yl)piperazine
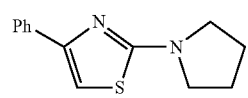
125488-15-5
4-Phenyl-2-pyrrolidinothiazole -continued
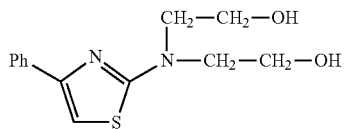
84552-01-2
Ethanol, 2,2'-[(4-phenyl-2-thiazolyl)imino]bis-
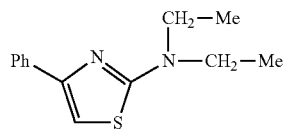
75654-98-7
2-(Diethylamino)-4-phenylthiazole
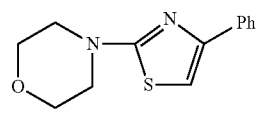
19983-28-9
2-Morpholino-4-phenylthiazole
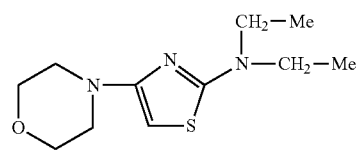
2-Thiazolamine, N,N-diethyl-4-(4-morpholinyl)- 192332-26-6
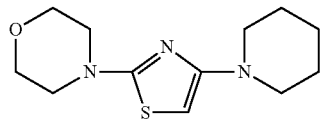
Morpholine, 4-[4-(1-piperidinyl)-2-thiazolyl]- 192332-18-6
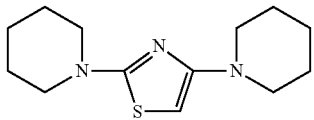
Piperidine, 1,1'-(2,4-thiazolediyl)bis- 170492-28-1
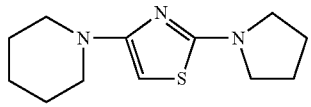
Piperidine, 1-[2-(1-pyrrolidinyl)-4-thiazolyl]- 169195-67-9
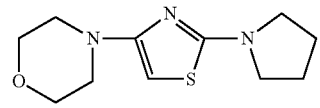
Morpholine, 4-[2-(1-pyrrolidinyl)-4-thiazolyl]- 169195-61-3

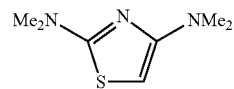
,4-Thiazolediamine,
N2,N2,N4,N4-tetramethyl-
70310-46-2
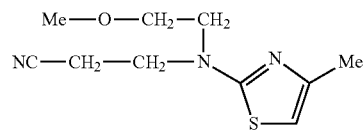
1408747-45-4
Propanenitrile, 3-[(2-
methoxyethyl)(4-methyl-2-
thiazolyl)amino]-
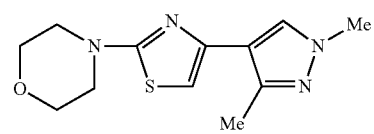
1389038-03-2
Morpholine, 4-[4-(1,3-dimethyl-
1H-pyrazol-4-yl)-2-thiazolyl]-
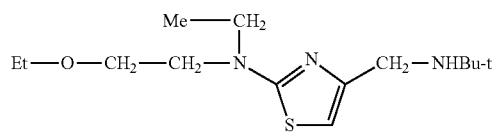
1378907-60-8
4-Thiazolemethanamine, N-
(1,1-dimethylethyl)-2-[(2-
ethoxyethyl)ethylamino]-
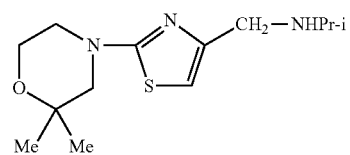
1378756-38-7
4-Thiazolemethanamine, 2-(2,2-
dimethyl-4-morpholinyl)-N-(1-
methylethyl)-
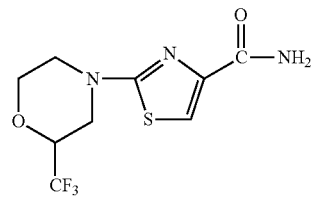
1351081-58-7
4-Thiazolecarboxamide, 2-[2-
(trifluoromethyl)-4-morpholinyl]-

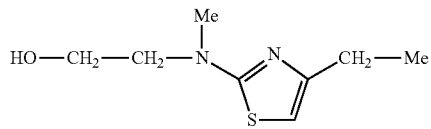
1343670-12-1
Ethanol, 2-[(4-ethyl-2-thiazolyl)methylamino]-
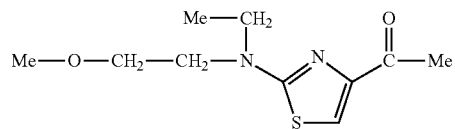
1342054-56-1
Ethanone, 1-[2-[ethyl(2-methoxyethyl)amino]-4-thiazolyl]-
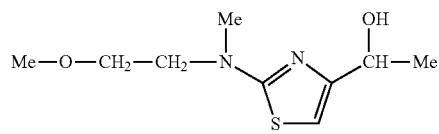
1339319-53-7
4-Thiazolemethanol, 2-[(2-methoxyethyl)methylamino]-α-methyl-
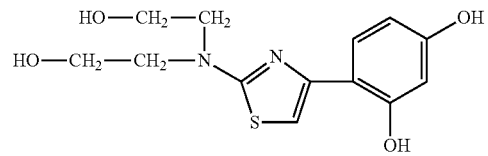
1335232-10-4
1,3-Benzenediol, 4-[2-[bis(2-hydroxyethyl)amino]-4-thiazolyl]-
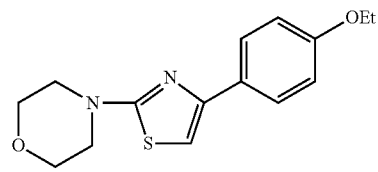
1286014-36-5
Morpholine, 4-[4-(4-ethoxyphenyl)-2-thiazolyl]-
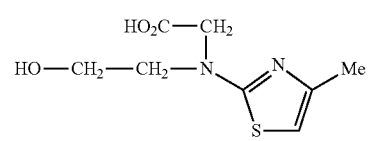
1251030-88-2
Glycine, N-(2-methoxyethyl)-N-(4-methyl-2-thiazolyl)-

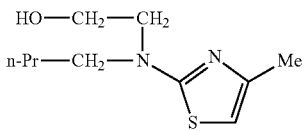
1249678-75-8
Ethanol, 2-[butyl(4-methyl-2-thiazolyl)amino]-
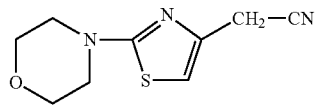
1023811-14-4
4-Thiazoleacetonitrile, 2-(4-morpholinyl)-
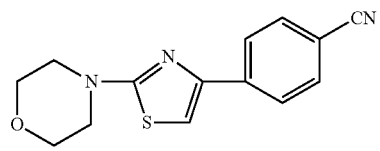
930082-29-4
Benzonitrile, 4-[2-(4-morpholinyl)-4-thiazolyl]-
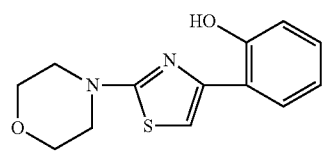
771436-47-6
Phenol, 2-[2-(4-morpholinyl)-4-thiazolyl]-
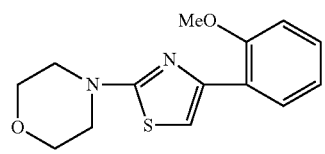
521318-88-7
Morpholine, 4-[4-(2-methoxyphenyl)-2-thiazolyl]-
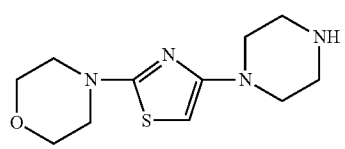
192332-20-0
Morpholine, 4-[4-(1-piperazinyl)-2-thiazolyl]-
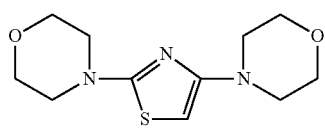
169195-54-4
Morpholine, 4,4'-(2,4-thiazolediyl)bis-

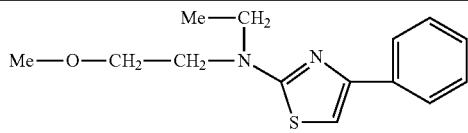

133694-26-5
2-Thiazolamine, N-ethyl-N-(2-methoxyethyl)-4-phenyl-

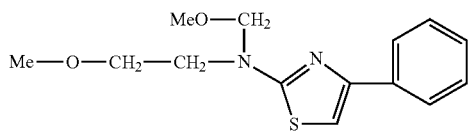

130531-64-5
2-Thiazolamine, N,N-bis(2-methoxyethyl)-4-phenyl-

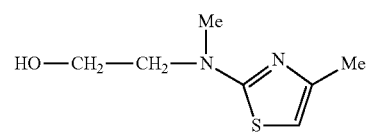

122320-85-8
Ethanol, 2-[methyl(4-methyl-2-thiazolyl)amino]-

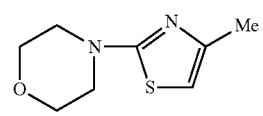

58350-40-6
Morpholine, 4-(4-methyl-2-thiazolyl)-

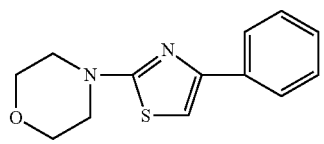

19983-28-9
2-Morpholino-4-phenylthiazole and also the optical isomers thereof, tautomers thereof, and the addition salts thereof with an acid or a base; the preferred couplers of the invention are those of formulae 1 to 3.

In the composition of the present invention, the coupler(s) of formula (I) are generally present in an amount ranging from 0.001% to 20% by weight approximately and preferably ranging from 0.005% to 6% by weight relative to the total weight of the dye composition.

Additional Couplers:

The composition according to the invention may also contain one or more additional couplers conventionally used for the dyeing of keratin fibres, other than those of formula (I) as defined previously. Among these couplers, mention may be made especially of meta-phenylenediamines, meta-aminophenols, meta-diphenols, naphthalene-based couplers and heterocyclic couplers, and also the addition salts thereof.

Examples that may be mentioned include 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, 2-methyl-5-aminophenol, 5-N-(β-hydroxyethyl)amino-2-methylphenol, 3-aminophenol and 3-amino-2-chloro-6-methylphenol, the addition salts thereof with an acid, and mixtures thereof.

In general, the addition salts of the oxidation bases and couplers that may be used in the context of the invention are especially chosen from the addition salts with an acid such as the hydrochlorides, hydrobromides, sulfates, citrates, succinates, tartrates, lactates, tosylates, benzenesulfonates, phosphates and acetates.

In the composition of the present invention, the coupler(s) are generally present in a total amount including the coupler(s) of formula (I) ranging from 0.001% to 30% by weight approximately and preferably ranging from 0.005% to 6% by weight relative to the total weight of the dye composition.

Additional Dyes:

According to a particular embodiment of the invention, the composition also contains one or more synthetic or natural direct dyes, chosen from ionic or nonionic species, preferably cationic or nonionic species.

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanine dyes, and natural direct dyes, alone or as mixtures.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin and orceins. Use may also be made of extracts or decoctions comprising these natural dyes and in particular henna-based extracts or poultices.

The direct dye(s) more particularly represent from 0.001% to 10% by weight relative to the total weight of the composition, and preferably from 0.005% to 6% by weight relative to the total weight of the composition.

iii) The Fatty Substance(s):

According to a preferred embodiment of the invention, the composition of the invention also comprises one or more fatty substances.

The term "fatty substance" means an organic compound that is insoluble in water at ordinary room temperature (25° C.) and at atmospheric pressure (760 mmHg) (solubility of less than 5%, preferably less than 1% and even more preferentially less than 0.1%). They bear in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

These fatty substances are neither polyoxyethylenated nor polyglycerolated. They are different from fatty acids since salified fatty acids constitute soaps which are generally soluble in aqueous media.

The fatty substances are especially chosen from $C_6$-$C_{16}$ hydrocarbons or hydrocarbons comprising more than 16 carbon atoms and in particular alkanes, oils of animal origin, oils of plant origin, synthetic glycerides, natural triglycerides, fluoro oils of synthetic origin, fatty alcohols, fatty acid and/or fatty alcohol esters other than natural or synthetic glycerides, non-silicone waxes, and silicones.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, which are optionally substituted, in particular, with one or more (in particular 1 to 4) hydroxyl groups. If they are unsaturated, these compounds may comprise one to three conjugated or unconjugated carbon-carbon double bonds.

As regards the $C_6$-$C_{16}$ alkanes, they are linear or branched, and possibly cyclic. Examples that may be mentioned include hexane, dodecane, undecane, tridecane, and isoparaffins, for instance isohexadecane and isodecane. The linear or branched hydrocarbons containing more than 16 carbon atoms may be chosen from liquid paraffins, petroleum jelly, liquid petroleum jelly, polydecenes, and hydrogenated polyisobutene such as Parleam®.

Among the animal oils, mention may be made of perhydrosqualene.

Among the triglycerides of plant or synthetic origin, mention may be made of liquid fatty acid triglycerides comprising from 6 to 30 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, castor oil, avocado oil, jojoba oil, shea butter oil, caprylic/capric acid triglycerides, for instance those sold by the company Stéarineries Dubois or those sold under the names Miglyol® 810, 812 and 818 by the company Dynamit Nobel.

Among the fluoro oils, mention may be made of perfluoromethylcyclopentane and perfluoro-1,3-dimethylcyclohexane, sold under the names Flutec® PC1 and Flutec® PC3 by the company BNFL Fluorochemicals; perfluoro-1, 2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the cosmetic compositions of the invention are saturated or unsaturated, and linear or branched, and comprise from 6 to 30 carbon atoms and more particularly from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

The wax(es) that may be used in the cosmetic composition are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the esters of fatty acids and/or of fatty alcohols, other than the triglycerides mentioned above, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisostearyl citrate; glyceryl trilactate; glyceryl trioctanoate; trioctyldodecyl citrate; trioleyl citrate, propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" is intended to mean oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar and fatty acid esters may be chosen in particular from the group comprising the esters or mixtures of sugar esters described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates or arachidonates, or mixtures thereof such as, in particular, oleate/palmitate, oleate/stearate or palmitate/stearate mixed esters.

More particularly, use is made of monoesters and diesters and in particular mono- or di-oleate, -stearate, -behenate, -oleate/palmitate, -linoleate, -linolenate or -oleate/stearate of sucrose, glucose or methylglucose.

An example that may be mentioned is the product sold under the name Glucate® DO by the company Amerchol, which is a methylglucose dioleate.

Examples of esters or mixtures of esters of sugar of fatty acid that may also be mentioned include:
 the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
 the products sold under the name Ryoto Sugar Esters, for example referenced B370 and corresponding to sucrose behenate formed from 20% monoester and 80% di-triester-polyester;
 the sucrose mono-di-palmitostearate sold by the company Goldschmidt under the name Tegosoft® PSE.

The silicones that may be used in the cosmetic composition (A) according to the present invention are volatile or non-volatile, cyclic, linear or branched silicones, which are unmodified or modified with organic groups, having a viscosity from $5\times10^{-6}$ to $2.5$ m$^2$/s at 25° C., and preferably $1\times10^{-5}$ to 1 m$^2$/s.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from poly(oxyalkylene) groups, amino groups and alkoxy groups.

Organopolysiloxanes are defined in greater detail in Walter Noll's *Chemistry and Technology of Silicones* (1968), Academic Press. They may be volatile or non-volatile.

When they are volatile, the silicones are more particularly chosen from those with a boiling point of between 60° C. and 260° C., and even more particularly from:
 cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxanes/methylalkylsiloxane type, such as Volatile Silicone® FZ 3109 sold by the company Union Carbide, of formula:

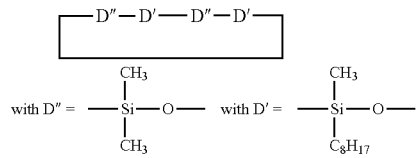

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January. 76, pp. 27-32, Todd & Byers, Volatile Silicone Fluids for Cosmetics.

Use is preferably made of non-volatile polydialkylsiloxanes, polydialkylsiloxane gums and resins, polyorganosiloxanes modified with the organofunctional groups above, and mixtures thereof.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:
- the Silbione® oils of the 47 and 70 047 series or the Mirasil® oils sold by Rhodia, for instance the oil 70 047 V 500 000;
- the oils of the Mirasil® series sold by the company Rhodia;
- the oils of the 200 series from the company Dow Corning, such as DC200 with a viscosity of 60 000 mm$^2$/s;
- the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C$_1$-C$_{20}$)dialkylsiloxanes.

The silicone gums that may be used in accordance with the invention are especially polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:
- the mixtures formed from a hydroxy-terminated polydimethylsiloxane or dimethiconol (CTFA) chain, and from a cyclic polydimethylsiloxane, also known as cyclomethicone (CTFA), such as the product Q2 1401 sold by the company Dow Corning;
- mixtures of a polydimethylsiloxane gum and a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
- mixtures of two PDMSs with different viscosities, and more particularly of a PDMS gum and of a PDMS oil, such as the product SF 1236 from the company General Electric. The product SF 1236 is a mixture of a gum SE 30 defined above with a viscosity of 20 m$^2$/s and of an oil SF 96 with a viscosity of $5 \times 10^{-6}$ m$^2$/s. This product preferably comprises 15% of gum SE 30 and 85% of an oil SF 96.

The organopolysiloxane resins that may be used in accordance with the invention are crosslinked siloxane systems containing the following units:

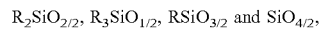

in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethylsiloxane structure.

Mention may also be made of the trimethylsiloxysilicate type resins sold in particular under the names X22-4914, X21-5034 and X21-5037 by the company Shin-Etsu.

The organomodified silicones that may be used in accordance with the invention are silicones as defined previously and comprising in their structure one or more organofunctional groups attached via a hydrocarbon-based group.

Besides the silicones described above, the organomodified silicones may be polydiarylsiloxanes, in particular polydiphenylsiloxanes, and polyalkylarylsiloxanes functionalized by the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:

the Silbione® oils of the 70 641 series from Rhodia;
the oils of the Rhodorsil® 70 633 and 763 series from Rhodia;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may be made of polyorganosiloxanes comprising:
polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;
substituted or unsubstituted amino groups, such as the products sold under the names GP 4 Silicone Fluid and GP 7100 by the company Genesee or the products sold under the names Q2 8220 and Dow Corning 929 or 939 by the company Dow Corning. The substituted amine groups are, in particular, $C_1$-$C_4$ aminoalkyl groups;
alkoxy groups such as the product sold under the name Silicone Copolymer F-755 by SWS Silicones, and Abil Wax® 2428, 2434 and 2440 by the company Goldschmidt.

The fatty substances are advantageously chosen from $C_6$-$C_{16}$ hydrocarbons or hydrocarbons comprising more than 16 carbon atoms, and in particular alkanes, oils of plant origin, fatty alcohols, fatty acid and/or fatty alcohol esters other than triglycerides, and silicones, or mixtures thereof.

Preferably, the fatty substance is an oil (a compound that is liquid at a temperature of 25° C. and at atmospheric pressure).

Preferably, the fatty substance is chosen from liquid petroleum jelly, $C_6$-$C_{16}$ alkanes, polydecenes, liquid esters of a fatty acid and/or of a fatty alcohol, and liquid fatty alcohols, or mixtures thereof. Better still, the fatty substance is chosen from liquid petroleum jelly, $C_6$-$C_{16}$ alkanes and polydecenes.

The fatty substances are preferably present in a content of greater than 10% by weight, relative to the total weight of the composition.

The dye composition which comprises the coupler(s) (I) has a fatty substance content preferably ranging from 10% to 80% by weight, and even more particularly ranging from 20% to 80% by weight, better still from 25% to 75% by weight and most particularly from 40% to 70% by weight relative to the total weight of the dye composition, more preferentially between 50% and 60% by weight relative to the total weight of the dye composition.

iv) The Metal Catalyst(s)

According to a particular embodiment of the invention, the composition which comprises one or more coupler(s) of formula (I) as defined previously also comprises one or more metal catalysts.

"Metal catalysts" are compounds that comprise one or more metals in their structure.

The metals are chosen from transition metals and rare-earth metals, and alloys thereof. In particular, the metals are chosen from transition metals and rare-earth metals.

Among the transition metals, mention may be made especially of manganese, iron, cobalt, copper, zinc, platinum, nickel, titanium, silver, zirconium, chromium, molybdenum, tungsten, platinum, gold and vanadium, and among these most particularly manganese.

Among the rare-earth metals, mention may particularly be made of cerium.

Thus, the metal catalysts are especially catalysts based on transition metals or on rare-earth metals, and more particularly manganese-based, vanadium-based or cerium-based catalysts.

The metal catalysts used may be in the form of metal salts, metal oxides or metal complexes, and mixtures thereof.

For the purposes of the present invention, the term "metal complexes" means systems in which the metal ion, i.e. the central atom, is bonded to one or more electron donors, called ligands, via chemical bonds. Examples that may be mentioned include porphyrins and phthalocyanines, which are especially cationic.

Preferably, the metal catalysts used in the dyeing process are chosen from metal salts.

For the purposes of the present invention, the term "metal salts" means salts derived from the action of an acid on a metal.

Preferentially, the metal catalysts used in the dyeing process are chosen from transition metal salts, such as manganese salts, and rare-earth metal salts, such as cerium salts, and also mixtures thereof.

The metal salts may be mineral or organic salts.

According to one variant, the metal salts are mineral and may be chosen from halides, carbonates, sulfates and phosphates, in particular optionally hydrated halides.

According to another preferred variant, the metal salts are in oxidation state II and bear two ligands derived from a $C_2$-$C_{10}$ carboxylic acid or (poly)hydroxy acid.

The term "carboxylic acid" means a carboxylic acid comprising a hydrocarbon-based chain which is linear or branched, and saturated or unsaturated, preferably saturated and/or linear, comprising from 1 to 10 carbon atoms, and comprising from 1 to 4 carboxylic groups —C(O)—OH, at least one of said —C(O)—OH functions of which is in the carboxylate form —C(O)—O⁻ complexed with the metal atom, preferably Mn(II).

The term "(poly)hydroxy acid" means any carboxylic acid which comprises a hydrocarbon-based chain which is linear or branched, and saturated or unsaturated, preferably saturated and/or linear, comprising from 1 to 10 carbon atoms and from 1 to 9 hydroxyl groups, and comprising from 1 to 4 carboxylic groups —C(O)—OH, at least one of said —C(O)—OH functions of which is in the carboxylate form —C(O)—O⁻ complexed with the metal atom, preferably Mn(II).

More particularly, the metal salt is complexed with two carboxylate groups such as that of formula (II):

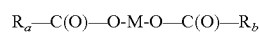

$$R_a\text{—C(O)—O-M-O—C(O)—}R_b \qquad (II)$$

and also the solvates thereof, such as hydrates, and enantiomers thereof, in which formula (II):

M represents a metal (II) or metal$^{2+}$ in oxidation state 2, $R_a$ and $R_b$, which may be identical or different, represent a (poly)(hydroxy)($C_1$-$C_6$)alkyl group. The metal catalysts are particularly chosen from organic acid salts of transition metals, especially of manganese, and mineral salts of rare-earth metals, especially of cerium.

According to one particular embodiment of the invention, the manganese is not a manganese oxide, but a manganese salt.

The organic metal salts may be more particularly chosen from organic acid salts such as citrates, lactates, glycolates, gluconates, acetates, propionates, fumarates, oxalates and tartrates, especially gluconates.

More preferentially, the metal catalysts are chosen from manganese gluconate and cerium chloride heptahydrate, in particular manganese gluconate. Preferably, the metal catalyst(s) are chosen from the compounds of formula (II) and more particularly represent manganese gluconate.

The metal catalysts may be present in a content ranging from 0.001% to 10% by weight, preferably in a content ranging from 0.001% to 1% by weight, better still ranging from 0.01% to 0.5% by weight relative to the total weight of the composition.

The Medium of the Compositions

Preferably, all the compositions used in the dyeing process of the invention are aqueous compositions.

The term "aqueous composition" means a composition comprising more than 5% by weight of water, preferably more than 10% by weight of water and even more advantageously more than 20% by weight of water.

Even more preferentially, the water concentration of the compositions of the invention may range from 10% to 90% and better still from 20% to 80% of the total weight of the composition. The compositions of the invention may optionally comprise one or more organic solvents.

Examples of organic solvents that may be mentioned include linear or branched $C_2$-$C_4$ alkanols, such as ethanol and isopropanol; polyols and polyol ethers, for instance 2-butoxyethanol, glycerol, propylene glycol, dipropylene glycol, propylene glycol monomethyl ether, diethylene glycol monomethyl ether and monoethyl ether, and also aromatic alcohols, for instance benzyl alcohol or phenoxyethanol, and mixtures thereof.

The organic solvent(s), if they are present, represent a content usually ranging from 1% to 40% by weight and preferably ranging from 5% to 30% by weight relative to the total weight of the composition containing them.

The Adjuvants:

The dye composition of the invention comprising the coupler(s) of formula (I) of the invention may also contain additional ingredients.

The dye composition in accordance with the invention may thus contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, film-forming agents, ceramides, preserving agents and opacifiers.

The above adjuvants are generally present in an amount, for each of them, of between 0.01% and 20% by weight, relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The dye composition according to the invention may be in various forms, such as in the form of liquids, creams or gels, or in any other form that is suitable for dyeing keratin fibres, and especially human hair.

The pH

The pH of the dye composition in accordance with the invention is generally between 2 and 12 approximately and preferably between 5 and 11 approximately. In the composition of the invention which comprises the coupler(s) of formula (I) and the oxidation base(s) the pH preferably ranges from 6.5 to 12 and better still from 7 to 12.

It may be adjusted to the desired value by means of additional acidifying or basifying agents, such as those mentioned below usually used in the dyeing of keratin fibres, or alternatively using standard buffer systems.

Among the acidifying agents, examples that may be mentioned include mineral or organic acids, for instance hydrochloric acid, orthophosphoric acid, sulfuric acid, carboxylic acids, for instance acetic acid, tartaric acid, citric acid and lactic acid, and sulfonic acids.

v) The Alkaline Agents:

Preferably, the dye composition comprises one or more organic or mineral, preferably organic, alkaline agents.

The alkaline agent(s) may be mineral or organic.

The mineral alkaline agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a $pK_b$ at 25° C. of less than 12, preferably less than 10 and even more advantageously less than 6. It should be noted that it concerns the $pK_b$ corresponding to the functional group having the highest basicity. In addition, the organic amines do not comprise any alkyl or alkenyl fatty chain comprising more than ten carbon atoms.

The organic alkaline agent(s) are chosen, for example, from alkanolamines, oxyethylenated and/or oxypropylenated ethylenediamines, amino acids and the compounds of formula (III) below:

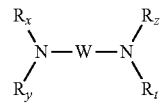

(III)

in which formula (III) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (III) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that can be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (IV) below, and also the salts thereof

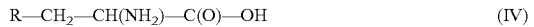

R—$CH_2$—CH($NH_2$)—C(O)—OH  (IV)

in which R represents a group chosen from imidazolyl, preferably imidazolyl-4-yl; aminopropyl; aminoethyl; —$(CH_2)_2$N(H)—C(O)—$NH_2$; and —$(CH_2)_2$—N(H)—C(NH)—$NH_2$.

The compounds corresponding to formula (IV) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) present in the composition of the invention are chosen from aqueous ammonia, alkanolamines, amino acids in neutral or ionic form, in particular basic amino acids, and preferably corresponding to those of formula (III).

Even more preferentially, the alkaline agent(s) are chosen from aqueous ammonia and alkanolamines, most particularly monoethanolamine (MEA).

Better still, the alkaline agent(s) are chosen from alkanolamines, most particularly monoethanolamine (MEA).

vi) The Chemical Oxidizing Agents:

According to a particular embodiment of the invention, the dye composition comprises at least one chemical oxidizing agent. The term "chemical oxidizing agent" means an oxidizing agent other than atmospheric oxygen.

The composition of the invention preferentially contains one or more chemical oxidizing agents.

The oxidizing agents conventionally used for the oxidation dyeing of keratin fibres are, for example, hydrogen peroxide, urea peroxide, alkali metal bromates, persalts such as perborates and persulfates, and peracids. Hydrogen peroxide is particularly preferred.

More particularly, the chemical oxidizing agent(s) are chosen from hydrogen peroxide, urea peroxide, alkali metal bromates, peroxygenated salts, for instance persulfates or perborates, peracids and precursors thereof and alkali metal or alkaline-earth metal percarbonates. The chemical oxidizing agent is advantageously hydrogen peroxide.

The concentration of chemical oxidizing agents may range more particularly from 0.1% to 50% by weight, even more preferentially from 0.5% to 20% by weight and better still from 1% to 15% by weight relative to the weight of the composition.

The Dyeing Process:

Another subject of the invention concerns a process for dyeing keratin fibres, in particular human keratin fibres such as the hair, which consists in applying to said fibres the dye composition of the invention comprising ingredients i), ii) and optionally iii) to vi) as defined previously.

The process of the present invention is a process in which the dye composition according to the present invention as defined previously is applied to the fibres, in the presence of at least one chemical oxidizing agent vi) as defined previously, for a time that is sufficient to develop the desired colouring. The colour may be revealed at acidic, neutral or alkaline pH, and the chemical oxidizing agent(s) may be added to the dye composition of the invention just at the time of use, or they may be used starting with an oxidizing composition containing them, which is applied simultaneously with or sequentially to the composition of the invention.

The oxidizing composition may further comprise various adjuvants which are used conventionally in compositions for dyeing hair, and are as defined above.

The oxidizing composition of the process of the invention particularly comprises at least one fatty substance. More particularly, the oxidizing composition has a fatty substance content preferably ranging from 10% to 90% by weight, even more particularly ranging from 20% to 80% by weight and better still from 20% to 50% by weight relative to the oxidizing composition.

According to a particular embodiment of the invention, the composition which comprises the ingredients i), ii) and optionally iii) to vi) as described previously is obtained by mixing at least two compositions, preferably two or three compositions.

According to a particular variant of the invention, the process uses the composition which is derived from mixing two compositions:

a dye composition (A) comprising:
  at least i) one oxidation base as defined previously;
  at least ii) one heteroaryl coupler of formula (I) or (I') as defined previously;
  optionally at least one alkaline agent v) as defined previously; and a composition (B) comprising:
  at least one chemical oxidizing agent vi) as defined previously;
  at least one of the compositions (A) and (B) comprising:
    at least iii) one fatty substance as defined previously; and
    optionally at least iv) one metal catalyst as defined previously;

it being understood that the content of fatty substance of the composition according to the invention resulting from the mixing of compositions (A)+(B) comprises at least 10%, in particular at least 15%, more particularly at least 20% and preferably at least 25% by weight relative to the total weight of the composition.

According to one variant, the preceding process uses a composition which is derived from the mixing of three compositions, the three compositions being aqueous or at least one of them being anhydrous.

In a particular process of the invention, two aqueous compositions (B') and (C') and one anhydrous composition (A') are used, the anhydrous composition (A') comprising at least iii) one fatty substance as defined previously, composition (B') comprising:
  at least i) one oxidation base as defined previously;
  at least ii) one heteroaryl coupler of formula (I) or (I') as defined previously; and composition (C') comprising:
  at least vi) one chemical oxidizing agent as defined previously;
it being understood that:
  optionally at least v) one alkaline agent as defined previously; which is included in compositions (A') and/or (B') and preferably solely in composition (B');
  optionally at least iv) one metal catalyst as defined previously being present in at least one of the three compositions (A'), (B') or (C');
  these three compositions being such that the content of fatty substance of the composition resulting from the mixing of the three compositions (A')+(B')+(C') comprises at least 10%, in particular at least 15%, more particularly at least 20% and preferably at least 25% by weight relative to the total weight of the composition derived from the mixing of (A')+(B')+(C').

In one variant of the invention, the keratin fibres are pretreated with a metal salt iv) as defined previously, preferably Mn or Ce salts, such as Mn or Ce gluconates.

The mixture obtained according to the preceding processes is then applied to the keratin fibres. After a leave-in time of approximately 3 to 50 minutes, preferably approximately 5 to 30 minutes, the keratin fibres are rinsed, washed with shampoo, rinsed again and then dried.

The ready-to-use composition that is finally applied to the keratin fibres may be in various forms, such as in the form of liquids, creams or gels or in any other form that is suitable for dyeing keratin fibres, and especially human hair.

Kit:

A subject of the invention is also a multi-compartment dyeing device or "kit" comprising a first compartment containing composition (A) as defined previously in the dyeing process, and at least a second compartment containing composition (B) as defined previously in the process, the compositions of the compartments being intended to be mixed before application, the composition after mixing of (A)+(B) is such that the amount of fatty substance preferably represents at least 10%, in particular at least 15%, more particularly at least 20% and preferably at least 25% by weight relative to the total weight of the composition resulting from the mixing of (A)+(B). According to one variant, the multi-compartment device of the invention is such that a first compartment contains a dye composition comprising ingredients i) and ii) and optionally iii) to v) as defined previously and a second compartment contains at least vi) one chemical oxidizing agent as defined previously.

These devices or kits may be equipped with a means for dispensing the desired mixture on the hair, such as the devices described in patent FR-2 586 913 in the name of the Applicant.

Using these devices, it is possible to dye the keratin fibres by means of a process that involves mixing a dye composition comprising at least i) one oxidation base and at least ii) one coupler of formula (I) as defined previously and with at least vi) one chemical oxidizing agent, and applying the mixture obtained to the keratin fibres for a time that is sufficient to develop the desired colouring.

The compounds of formulae (I) and (I') are known to those skilled in the art and are commercial products or may be obtained according to the synthetic methods known in the field of heterocycle synthesis: see, for example, U.S. Pat. No. 5,892,046 and WO 02/080 160, or WO 2003/063 809.

The examples which follow serve to illustrate the invention without, however, exhibiting a limiting nature.

EXAMPLES

Dye Composition

The dye composition is prepared at the time of use by mixing the three compositions below: 6.7 g of composition A+2.7 g of composition B+10 g of composition C. Each of the compositions is specified in the following tables:

Composition A

| Ingredients | A (g %) |
|---|---|
| Liquid petroleum jelly | 64.5 |
| 2-Octyldodecanol | 11.5 |
| Distearyldimethylammonium-modified hectorite | 3 |
| Propylene carbonate | 1 |
| Oxyethylenated (4 OE) sorbitan monolaurate | 11 |
| Glycol distearate | 8 |
| Oxyethylenated (2 OE) lauryl alcohol | 1 |

Composition B

| Ingredients | B (g %) |
|---|---|
| Base 1, 2 or 3* | $20 \times 10^{-3}$ mol % |
| Coupler of the invention** 1, 2, 3 or 4 | $20 \times 10^{-3}$ mol % |
| Free monoethanolamine | 0.14 g |
| Sodium metabisulfite | 0.7 g |
| L-Ascorbic acid | 0.25 g |
| Propylene glycol | 6.2 g |
| Ethanol | 15.1 g |
| Hexylene glycol | 3 g |
| Dipropylene glycol | 3 g |
| Benzyl alcohol | 6 g |
| pH agent | qs pH = 7 |
| Deionized water | qs 100 g |

Base*

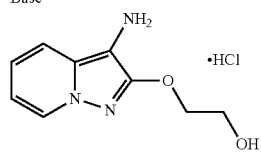

Base 1
Heterocyclic 2-hydroxyethoxy-3-aminopyrazolopyridine HCl

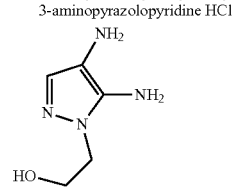

Base 2
1-Hydroxyethyl-4,5-diaminopyrazole sulfate

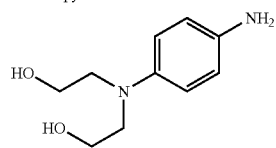

Base 3
N,N-Bis(2-hydroxyethyl)-p-phenylenediamine sulfate

| Ingredients | B (g %) |
|---|---|
| **Couplers: |  |

Coupler 1
126533-98-8

Coupler 2
169195-54-4

Coupler 3
130531-64-5

Coupler 4
19983-28-9

Composition C (Oxidizing Agent)

| Ingredients | C (g %) |
|---|---|
| 50% hydrogen peroxide solution | 12 |
| Liquid petroleum jelly | 20 |
| Cetylstearyl alcohol (30/70: $C_{16}/C_{18}$) | 8 |
| Oxyethylenated cetylstearyl alcohol (33 OE) | 3 |
| Tetrasodium pyrophosphate decahydrate | 0.03 |
| Crystalline sodium hexahydroxystannate | 0.04 |
| Diethylenetriaminepentaacetic acid, pentasodium salt as a 40% aqueous solution | 0.15 |
| Polydimethyldiallylammonium chloride at 40% in water, non-stabilized | 0.5 |
| Poly[(dimethyliminio)-1,3-propanediyl(dimethyliminio)-1,6-hexanediyl dichloride] as an aqueous 60% solution | 0.25 |
| Phosphoric acid | qs pH |
| Protected oxyethylenated (4 OE) rapeseed acid amides | 1.3 |
| Vitamin E | 0.1 |
| Glycerol | 0.5 |
| Deionized water | qs 100 |

Dyeing Process

Pairs of locks of natural Caucasian hair containing 90% of grey hairs (NG) are treated with 19.4 g of dye composition mixture A+B+C, which is then left on for 35 minutes at room temperature, in comparison with a series of locks that is not treated with the composition.

After this leave-on time, the locks are washed with iNOA POST shampoo, rinsed and then dried under a hood.

The colouring obtained is measured using a Minolta CM-3600D spectrocolorimeter.

Results Obtained

Example 1

Dyeing Tests

Couplers 1 to 4 of the invention are applied in combination with bases 1 to 3.

Intense and varied colours are obtained.

The results in terms of the build-up are collated in Table 1 below.

TABLE 1

| Description | L* (D65) | a* (D65) | b* (D65) | ΔE*ab(D65) - build-up | Colour |
|---|---|---|---|---|---|
| Non-dyed control NG lock | 66.68 | 0.4 | 15.05 | — | |
| Dyed with Base 1 + coupler 1 | 45.19 | 6.04 | 19.81 | 22.72 | Golden |
| Dyed with Base 1 + coupler 2 | 43.85 | 16.98 | 29.16 | 31.38 | Coppery |
| Dyed with Base 2 + coupler 2 | 49.1 | 29.69 | 28.84 | 36.58 | Coppery red |
| Dyed with Base 3 + coupler 2 | 39.88 | 9.02 | 3.97 | 29.24 | Violet beige |
| Dyed with Base 1 + coupler 3 | 48.58 | 3.74 | 3.32 | 20.74 | Beige |
| Dyed with Base 2 + coupler 3 | 45.71 | 21.51 | 17.04 | 29.16 | Coppery red |
| Dyed with Base 3 + coupler 3 | 46.5 | 0.97 | 8.39 | 20.43 | Grey |
| Dyed with Base 1 + coupler 4 | 51.22 | 5.84 | 6.87 | 17.24 | Beige |
| Dyed with Base 2 + coupler 4 | 47.51 | 26.67 | 22.95 | 33.01 | Coppery red |
| Dyed with Base 3 + coupler 4 | 47.82 | 0.76 | 8.74 | 19.06 | Grey |

Example 2

Tests of Dyeing with Catalysis

Tests are performed this time in the presence of manganese gluconate catalyst (pretreatment composition 1) and replacing at the same molar concentration the base 2-hydroxy-3-aminopyrazolopyridine HCl of composition B with 2,5-dimethoxyaniline and this time using as coupler the heteroaryl coupler 4.

Composition 1

| SM | Composition 1 |
|---|---|
| Laureth-2 | 2 g |
| Decyl glucoside | 2 g |
| Mineral oil | 78.5 g |
| PEG-150/decyl glucoside/SMDI copolymer | 0.5 g |
| Manganese gluconate (CAS No. 6485-39-8) | 0.4 g |
| Water | qs 100 g |

Locks of natural Caucasian hair containing 90% grey hairs (NG) are treated with:
composition 1, which is left on for 10 minutes at room temperature, and then rinsed out and dried manually,
the 19.4 g of dye composition mixture A+B+C, in a proportion of 6.7 g of composition A+2.7 g of composition B+10 g of composition C, which is then left on for 35 minutes at room temperature.

With the manganese gluconate pretreatment, intense blonde tints are obtained.

The results in terms of the build-up are collated in Table 2 below.

TABLE 2

| Coupling | Type of locks | L* | a* | b* | ΔE*ab |
|---|---|---|---|---|---|
| Coupler 3 + 2,5-dimethoxyaniline with pretreatment with Mn$^{2+}$ | NG | 34.52 | 3.89 | 8.97 | 30.81 |

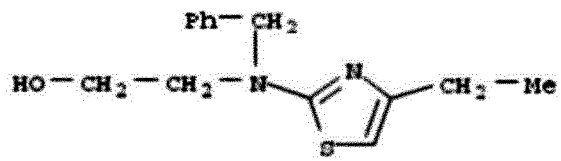
Claim 11, Column 102, second row, first position, replace the formula with:
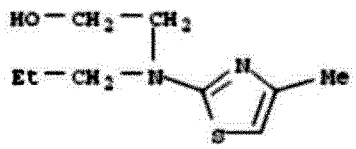
Claim 11, Column 102, second row, middle position, replace the formula with:
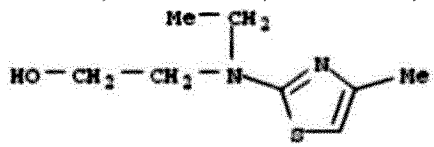
Claim 11, Column 102, third row, first position, replace the formula with:
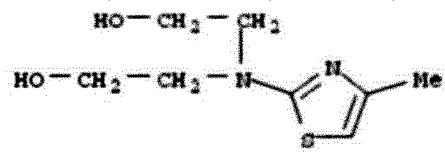
Claim 11, Column 105, middle position, replace the formula with:
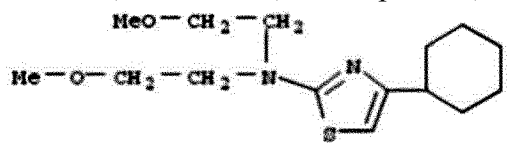

The invention claimed is:

1. A composition comprising:
   i) at least one oxidation base chosen from heterocyclic bases or para-phenylenediamine bases; and
   ii) at least one heteroaryl coupler corresponding to formula (I) below, the addition salts thereof with an organic or mineral acid or base, optical or geometrical isomers, tautomers, or solvates thereof:

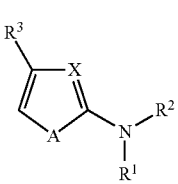

(I)

wherein:
A is chosen from oxygen or sulfur atoms;
X is chosen from a nitrogen atom or a C—R$^4$ group;
R$^1$ and R$^2$, which may be identical or different, are chosen from a linear or branched (C$_1$-C$_4$) alkyl group, optionally interrupted with at least one heteroatom, and optionally hydrogenated or (C$_1$-C$_4$)alkylated, and/or optionally substituted; an optionally substituted aryl; an optionally substituted heteroaryl; or an optionally substituted (hetero)cycloalkyl; or alternatively, R$^1$ and R$^2$ form, together with the nitrogen atom that bears them, an optionally substituted heterocycloalkyl, optionally comprising at least one heteroatom chosen from oxygen, sulfur, or nitrogen; and
R$^3$ and R$^4$, which may be identical or different, are chosen from a linear or branched (C$_1$-C$_4$) alkyl group, optionally interrupted with at least one heteroatom, and optionally hydrogenated or (C$_1$-C$_4$)alkylated, and/or optionally substituted with at least one group; an optionally substituted aryl; an optionally substituted heteroaryl; or an optionally substituted (hetero)cycloalkyl.

2. The composition according to claim 1, wherein the at least one oxidation base is chosen from para-phenylenediamines, bis(phenyl)alkylenediamines, para-aminophenols, ortho-aminophenols, heterocyclic bases, 3-aminopyrazolo[1,5-a]pyridine bases, pyrazole derivatives, or the addition salts thereof.

3. The composition according to claim 1, wherein the at least one oxidation base is chosen from
heterocyclic bases,
3-aminopyrazolo[1,5-a]pyridines substituted in position 2 with:
  a) a (di)($C_1$-$C_6$)(alkyl)amino group, the alkyl groups optionally substituted with at least one hydroxyl, amino or imidazolium group;
  b) a cationic or non-cationic 5- to 7-membered heterocycloalkyl group comprising from 1 to 3 heteroatoms, optionally substituted with at least one ($C_1$-$C_6$)alkyl group; or
  c) a ($C_1$-$C_6$)alkoxy group optionally substituted with at least one group chosen from hydroxyl, β-hydroxyalkoxy, or the addition salts thereof; or
pyrazole derivatives, 4,5-diamino-1-methylpyrazole, 4,5-diamino-1-(β-hydroxy-ethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, or addition salts thereof.

4. The composition according to claim 1, wherein the at least one heteroaryl coupler is chosen from thiazolyl couplers corresponding to formula (I') below, the addition salts thereof with an organic or mineral acid or base, optical or geometrical isomers, tautomers, solvates, or hydrates thereof:

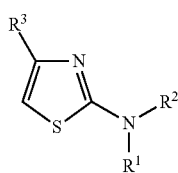

wherein:
$R^1$ and $R^2$, which may be identical or different, are chosen from a linear or branched ($C_1$-$C_4$) alkyl group, optionally interrupted with at least one heteroatom, and optionally hydrogenated or ($C_1$-$C_4$)alkylated, and/or optionally substituted; an optionally substituted aryl; an optionally substituted heteroaryl; or an optionally substituted (hetero)cycloalkyl; or alternatively, $R^1$ and $R^2$ form, together with the nitrogen atom that bears them, an optionally substituted heterocycloalkyl, optionally comprising at least one heteroatom chosen from oxygen, sulfur, or nitrogen; and $R^3$ is chosen from a linear or branched ($C_1$-$C_4$) alkyl group, optionally interrupted with at least one heteroatom, and optionally hydrogenated or ($C_1$-$C_4$)alkylated, and/or optionally substituted with at least one group; an optionally substituted aryl; an optionally substituted heteroaryl, or an optionally substituted (hetero)cycloalkyl.

5. The composition according to claim 1, wherein the least one heteroaryl coupler corresponds to formula (I) wherein $R^1$ and $R^2$ are chosen from a ($C_1$-$C_6$)alkyl group optionally interrupted with at least one heteroatom chosen from oxygen, sulfur, or nitrogen.

6. The composition according to claim 1, wherein the at least one heteroaryl coupler corresponds to formula (I) wherein $R^1$ and $R^2$ form, together with the nitrogen atom that bears them, an optionally substituted 5- or 6-membered, heterocycloalkyl group, morpholino, piperazino, or piperidino.

7. The composition according to claim 1, wherein the at least one heteroaryl coupler corresponds to formula (I) wherein $R^3$ is chosen from i) a ($C_1$-$C_6$)alkyl group which is optionally substituted with at least one hydroxyl group; ii) an optionally substituted aryl group; or iii) an optionally substituted 5- or 6-membered, heterocycloalkyl, morpholino, piperazino, or piperidino.

8. The composition according to claim 4, wherein the least one heteroaryl coupler corresponds to formula (I') wherein $R^1$ and $R^2$ are chosen from a ($C_1$-$C_6$)alkyl group optionally interrupted with at least one heteroatom chosen from oxygen, sulfur, or nitrogen.

9. The composition according to claim 4, wherein the at least one heteroaryl coupler corresponds to formula (I') wherein $R^1$ and $R^2$ form, together with the nitrogen atom that bears them, an optionally substituted 5- or 6-membered, heterocycloalkyl group, morpholino, piperazino, or piperidino.

10. The composition according to claim 4, wherein the at least one heteroaryl coupler corresponds to formula (I') wherein $R^3$ is chosen from i) a ($C_1$-$C_6$)alkyl group which is optionally substituted with at least one hydroxyl group; ii) an optionally substituted aryl group; or iii) an optionally substituted 5- or 6-membered, heterocycloalkyl, morpholino, piperazino, or piperidino.

11. The composition according to claim 4, wherein the at least one heteroaryl coupler is chosen from the following compounds, the optical isomers, tautomers, and the addition salts thereof with an acid or a base:

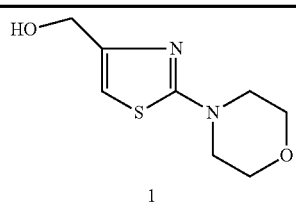

1

126533-98-8

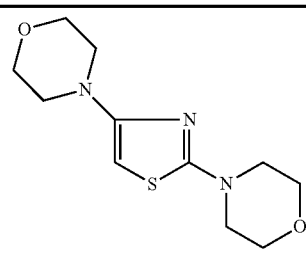

2

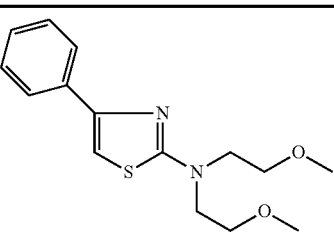

3

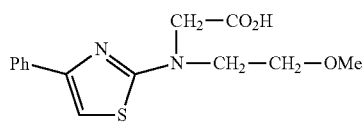

1303757-32-5
Glycine, N-(2-methoxyethyl)-N-(4-phenyl)-2-thiazolyl)-

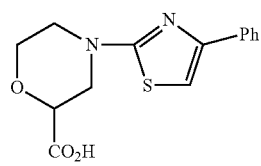

1291897-04-5
2-Morpholinecarboxylic acid, 4-(4-phenyl-2-thiazolyl)-

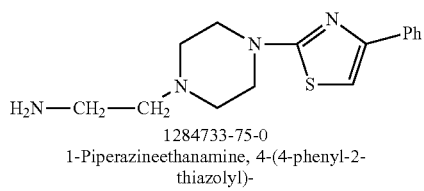

1284733-75-0
1-Piperazineethanamine, 4-(4-phenyl-2-thiazolyl)-

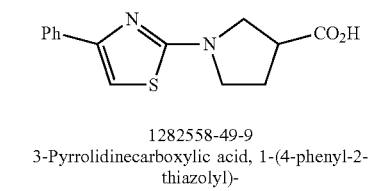

1282558-49-9
3-Pyrrolidinecarboxylic acid, 1-(4-phenyl-2-thiazolyl)-

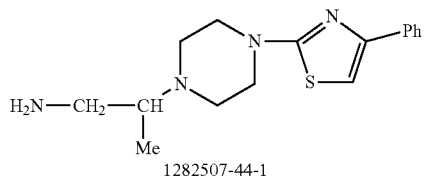

1282507-44-1
1-Piperazineethanamine, 1-methyl-4-(4-phenyl-2-thiazolyl)-

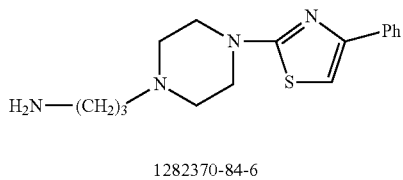

1282370-84-6
1-Piperazinepropanamine, 4-(4-phenyl-2-thiazolyl)-

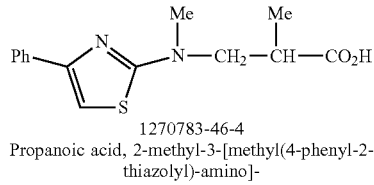

1270783-46-4
Propanoic acid, 2-methyl-3-[methyl(4-phenyl-2-thiazolyl)-amino]-

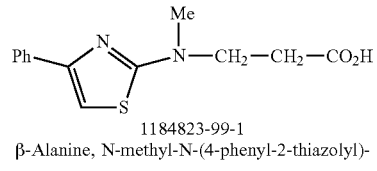

1184823-99-1
β-Alanine, N-methyl-N-(4-phenyl-2-thiazolyl)-

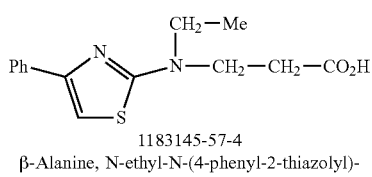

1183145-57-4
β-Alanine, N-ethyl-N-(4-phenyl-2-thiazolyl)-

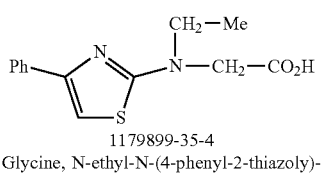

1179899-35-4
Glycine, N-ethyl-N-(4-phenyl-2-thiazoly)-

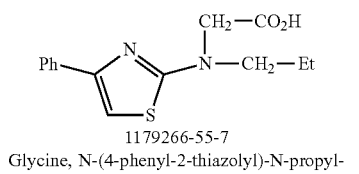

1179266-55-7
Glycine, N-(4-phenyl-2-thiazolyl)-N-propyl-

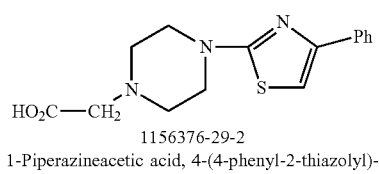

1156376-29-2
1-Piperazineacetic acid, 4-(4-phenyl-2-thiazolyl)-

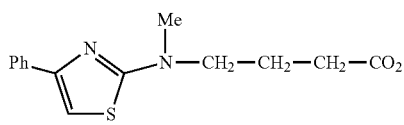

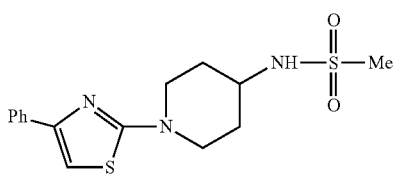

| | |
|---|---|
| 1156152-39-4<br>Butanoic acid, 4-[methyl(4-phenyl-2-thiazolyl)amino]- | 943337-52-8<br>Methanesulfonamide, N-[1-(4-phenyl-2-thiazolyl)-4-piperidinyl]- |
| 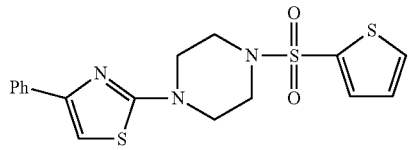<br>933827-86-2<br>Piperazine, 1-(4-phenyl-2-thiazolyl)-4-(2-thienylsulfonyl)- | 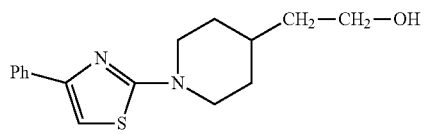<br>928026-91-9<br>4-Piperidineethanol, 1-(4-phenyl-2-thiazolyl)- |
| 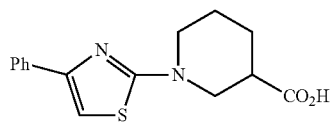<br>927803-58-5<br>3-Piperidinecarboxylic acid, 1-(4-phenyl-2-thiazolyl)- | 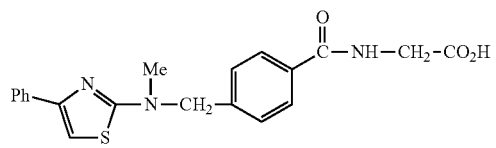<br>898246-34-9<br>Glycine, N-[4-[[methyl(4-phenyl-2-thiazolyl)amino]methyl]benzoyl]- |
| 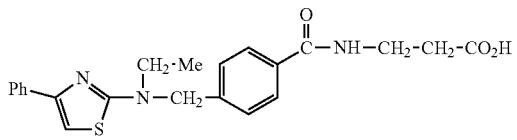<br>898246-20-3<br>β-Alanine, N-[4-[[ethyl(4-phenyl-2-thiazoly)amino]methyl]benzoyl]- | 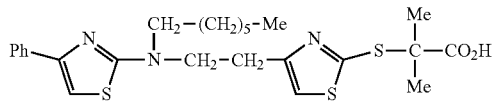<br>886614-39-7<br>Propanoic acid, 2-[[4-[2-[heptyl(4-phenyl-2-thiazolyl)amino]ethyl]-2-thiazolyl]thio]-2-methyl- |
| 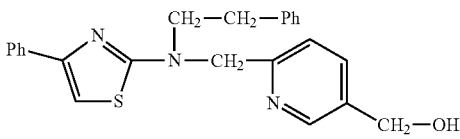<br>858114-97-3<br>3-Pyridinemethanol, 6-[[(2-phenylethyl)(4-phenyl-2-thiazolyl)amino]methyl]- | 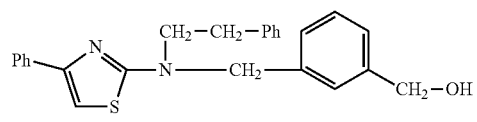<br>858114-75-7<br>Benzenemethanol, 3-[[(2-phenylethyl)(4-phenyl-2-thiazolyl)amino]methyl]- |
| 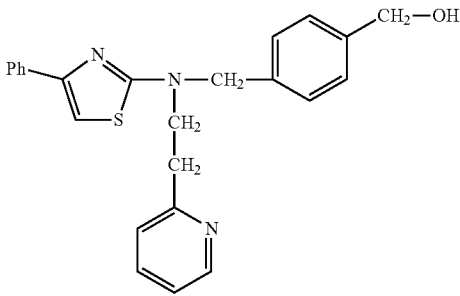<br>858114-71-3<br>Benzenemethanol, 4-[[(4-phenyl-2-thiazolyl)[2-(2-pyridinyl)ethyl]amino]methyl]- | 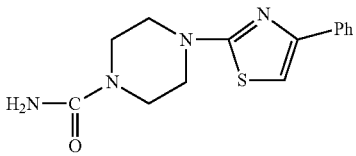<br>857496-78-7<br>1-Piperazinecarboxamide, 4-(4-phenyl-2-thiazolyl)- |
| 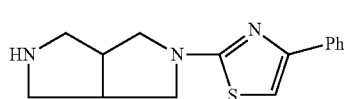 | 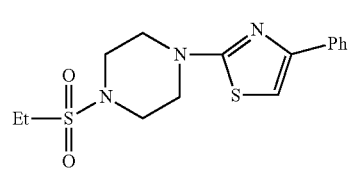 |

851523-24-5
Pyrrolo[3,4-c]pyrrole, octahydro-2-(4-phenyl-2-thiazolyl)-

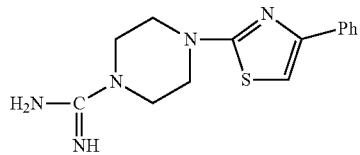

775270-75-2
1-Piperazinecarboximidamide, 4-(4-phenyl-2-thiazolyl)-

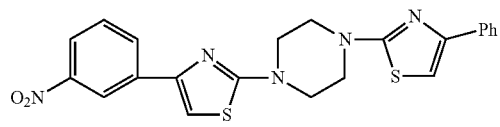

696633-56-4
Piperazine, 1-[4-(3-nitrophenyl)-2-thiazolyl]-4-(4-phenyl-2-thiazolyl)-

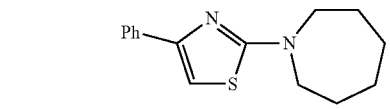

695160-01-1
1H-Azepine, hexahydro-1-(phenyl-2-thiazolyl)-

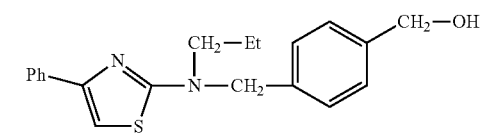

691904-88-8
Benzenemethanol, 4-[[(4-phenyl-2-thiazolyl)propylamino]methyl]-

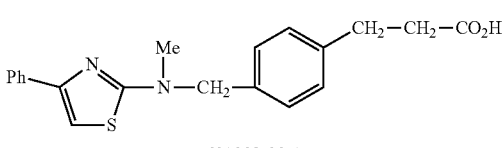

691903-92-1
Benzenepropanoic acid, 4-[[methyl(4-phenyl-2-thiazolyl)amino]methyl]-

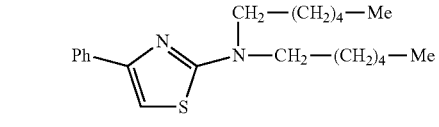

480999-15-3
2-Thiazolamine, N,N-dihexyl-4-phenyl-

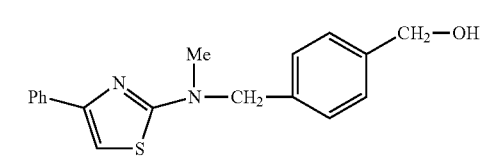

837386-75-1
Piperazine, 1-(ethylsulfonyl)-4-(4-phenyl-2-thiazolyl)-

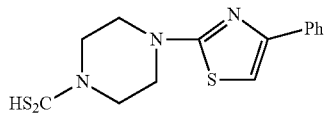

743372-21-6
1-Piperazinecarbodithioic acid, 4-(4-phenyl-2-thiazolyl)-

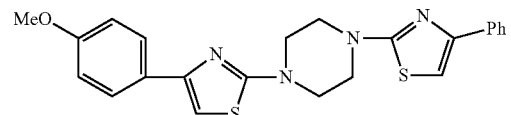

695198-50-6
Piperazine, 1-[4-(4-methoxyphenyl)-2-thiazolyl]-4-(4-phenyl-2-thiazolyl)-

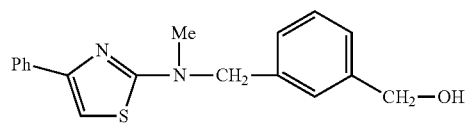

691904-94-6
Benzenemethanol, 3-[[methyl(4-phenyl-2-thiazolyl)amino]methyl]-

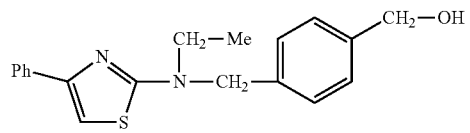

691904-86-6
Benzenemethanol, 4-[[ethyl(4-phenyl-2-thiazolyl)amino]methyl]-

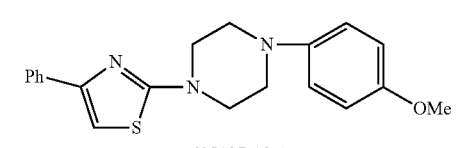

685107-19-1
Piperazine, 1-(4-methoxyphenyl)-4-(4-phenyl-2-thiazolyl)-

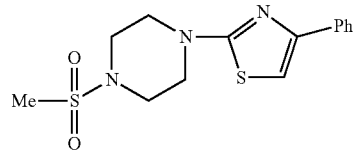

447428-28-6
Piperazine, 1-(methylsulfonyl)-4-(4-phenyl-2-thiazolyl)-

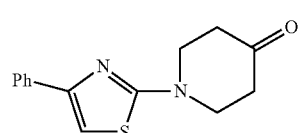

441357-38-6
4-[Methyl(4-phenyl-2-thiazolyl)aminomethyl] benzyl alcohol

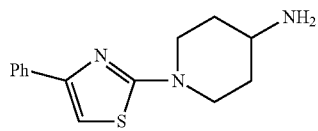

380828-82-0
1-[1-(4-Phenyl-2-thiazolyl)-4-piperidinyl]amine

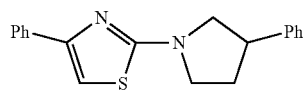

345990-58-1
Thiazole, 4-phenyl-2-(3-phenyl-1-pyrrolidinyl)-

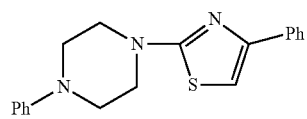

312504-57-7
Piperazine, 1-phenyl-4-(4-phenyl-2-thiazolyl)-

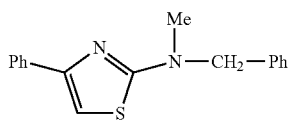

309732-99-8
2-Thiazolamine, N-methyl-4-phenyl-N-(phenylmethyl)-

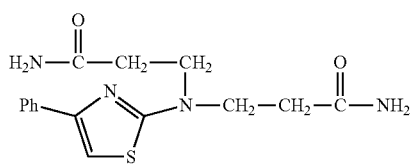

300686-24-2
Propanamide, 3,3'-[(4-phenyl-2-thiazolyl)imino]bis-

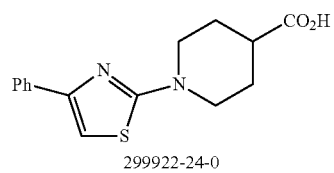

299922-24-0
4-Piperidinecarboxylic acid, 1-(4-phenyl-2-thiazolyl)-

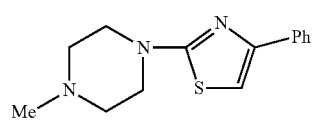

392643-02-6
1-(4-Phenyl-1,3-thiazol-2-yl)-4-piperidinone

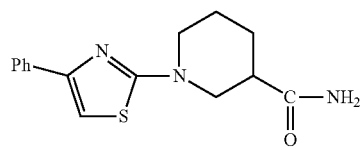

346662-46-2
3-Piperidinecarboxamide, 1-(4-phenyl-2-thiazolyl)-

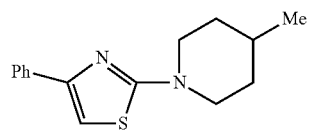

345990-52-5
Piperidine, 4-methyl-1-(4-phenyl-2-thiazolyl)-

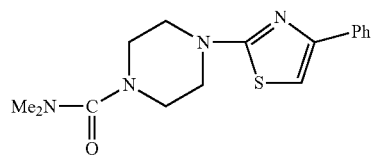

309734-77-8
1-Piperazinecarboxamide, N,N-dimethyl-4-(4-phenyl-2-thiazolyl)-

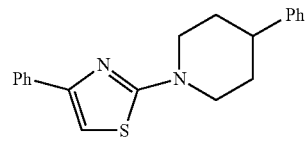

309282-11-9
Piperidine, 4-phenyl-1-(4-phenyl-2-thiazolyl)-

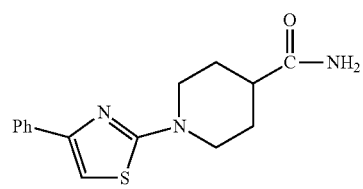

299922-31-9
4-Piperidinecarboxamide, 1-(4-phenyl-2-thiazolyl)-

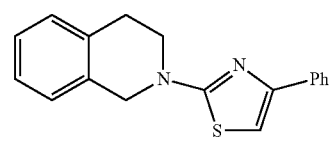

299922-22-8
Isoquinoline, 1,2,3,4-tetrahydro-2-(4-phenyl-2-thiazolyl)-

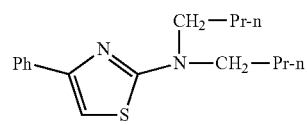

231963-95-4
Piperazine, 1-methyl-4-(4-phenyl-2-thiazolyl)-

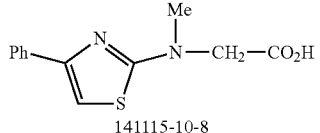

141115-10-8
Glycine, N-methyl-N-(4-phenyl-2-thiazolyl)-

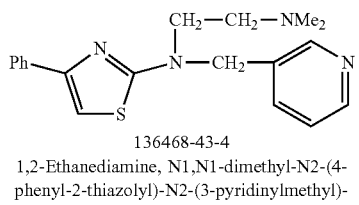

136468-43-4
1,2-Ethanediamine, N1,N1-dimethyl-N2-(4-phenyl-2-thiazolyl)-N2-(3-pyridinylmethyl)-

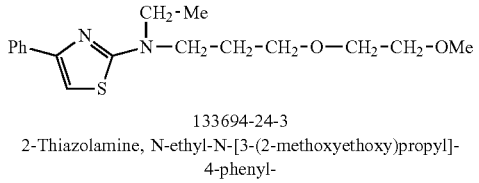

133694-24-3
2-Thiazolamine, N-ethyl-N-[3-(2-methoxyethoxy)propyl]-4-phenyl-

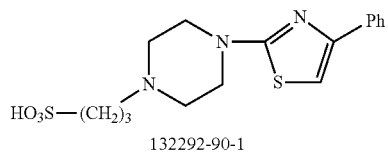

132292-90-1
1-Piperazinepropanesulfonic acid, 4-(4-phenyl-2-thiazolyl)-

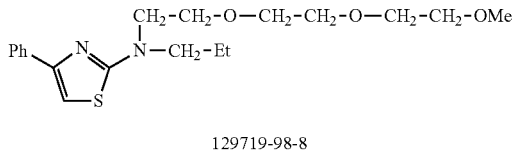

129719-98-8
2-Thiazolamine, N-[2-[2-(2 methoxyethoxy)ethoxy]ethyl]-4-phenyl-N-propyl-

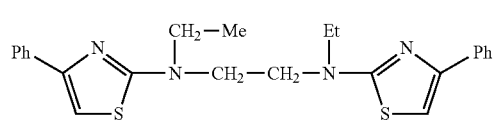

128699-95-6
1,2-Ethanediamine, N,N'-diethyl-N,N'-bis(4-phenyl-2-thiazolyl)-

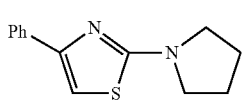

169037-17-6
2-(Dibutylamino)-4-phenylthiazole-

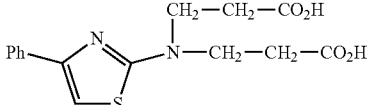

138537-78-7
β-Alanine, N-(2-carboxyethyl)-N-(4-phenyl-2-thiazolyl)-

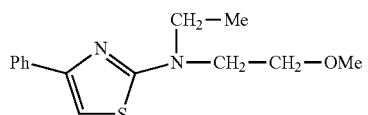

133694-26-5
2-Thiazolamine, N-ethyl-N-(2-methoxyethyl)-4-phenyl-

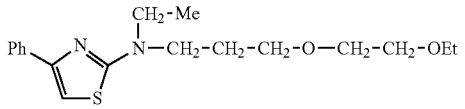

132865-54-4
2-Thiazolamine, N-[3-(2-ethoxyethoxy)propyl]-N-ethyl-4-phenyl-

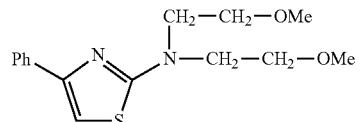

130531-64-5
2-Thiazolamine, N,N-bis(2-methoxyethyl)-4-phenyl-

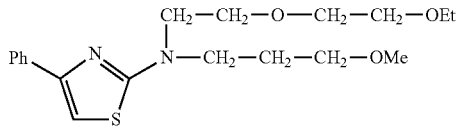 [SMILES: CCOCCOCCN(CCCOC)c1nc(-c2ccccc2)cs1]

129719-95-5
2-Thiazolamine, N-[2-(2-ethoxyethoxy)ethyl]-N-(3-methoxypropyl)-4-phenyl-

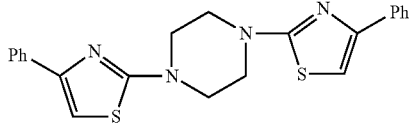 [SMILES: c1ccc(-c2csc(N3CCN(c4nc(-c5ccccc5)cs4)CC3)n2)cc1]

128699-96-7
1,4-Bis(4-phenylthiazol-2-yl)piperazine

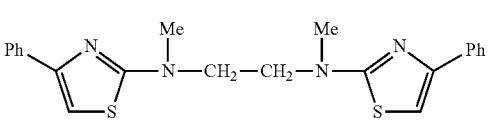 [SMILES: CN(CCN(C)c1nc(-c2ccccc2)cs1)c1nc(-c2ccccc2)cs1]

128699-84-3
1,2-Ethanediamine, N,N'-dimethyl-N,N'-bis(4-phenyl-2-thiazolyl)-

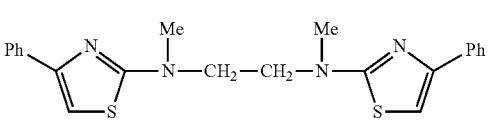 [SMILES: CN(CCN(C)c1nc(-c2ccccc2)cs1)c1nc(-c2ccccc2)cs1]

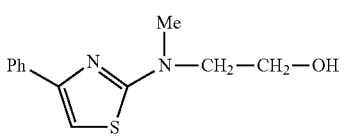

125488-15-5
4-Phenyl-2-pyrrolidinothiazole

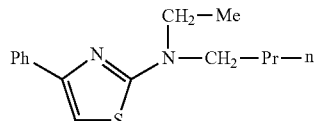

89314-44-3
2-Thiazolamine, N-butyl-N-ethyl-4-phenyl-

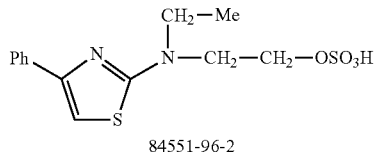

84551-96-2
Ethanol, 2-[ethyl(4-phenyl-2-thiazolyl)amino] 1-(hydroqen sulfate)

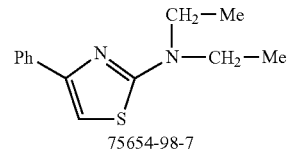

75654-98-7
2-(Diethylamino)-4-phenylthiazole

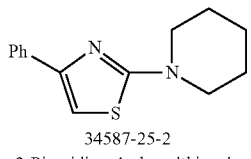

34587-25-2
2-Piperidino-4-phenylthiazole

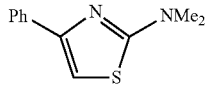 [SMILES: CN(C)c1nc(-c2ccccc2)cs1]

6142-13-8
2-(Dimethylamino)-4-phenylthiazole

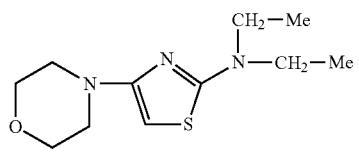 [SMILES: CCN(CC)c1nc(N2CCOCC2)cs1]

2-Thiazolamine, N,N-diethyl-4-(4-morpholinyl)-
192332-26-6

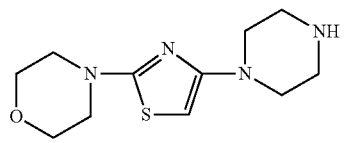 [SMILES: c1sc(N2CCOCC2)nc1N1CCNCC1]

Morpholine, 4-[4-(1-piperazinyl)-2-thiazolyl]-
192332-20-0

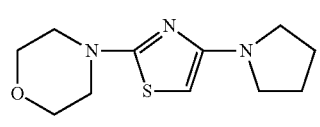 [SMILES: c1sc(N2CCOCC2)nc1N1CCCC1]

122320-82-5
Ethanol, 2-[methyl(4-phenyl-2-thiazolyl)amino]-

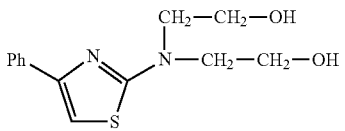

84552-01-2
Ethanol, 2,2'-[(4-phenyl-2-thiazolyl)imino]bis-

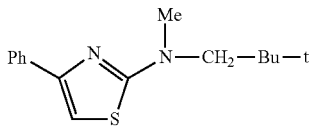

82721-96-8
2-Thiazolamine, N-(2,2-dimethylpropyl)-N-methyl-4-phenyl-

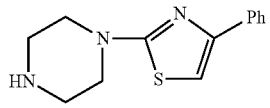

69389-14-6
1-(4-Phenyl-2-thiazolyl)piperazine

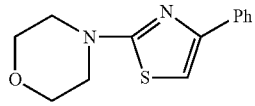

19983-28-9
2-Morpholino-4-phenylthiazole

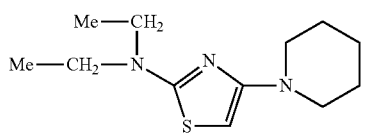

2-Thiazolamine, N,N-diethyl-4-(1-piperidinyl)-
192332-28-8

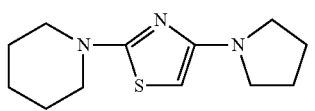

192332-24-4 Piperidine, 1-[4-(1-pyrrolidinyl)-2-thiazolyl]-

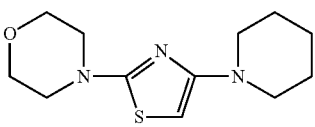

Morpholine, 4-[4-(1-piperidinyl)-2-thiazolyl]-
192332-18-6

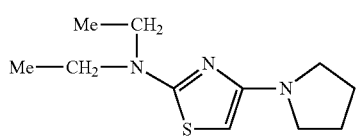

Morpholine, 4-[4-(1-pyrrolidinyl)-2-thiazolyl]-
170492-35-0

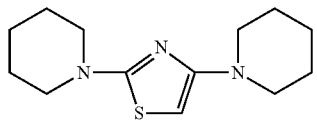 [SMILES: c1sc(N2CCCCC2)nc1N1CCCCC1]

Piperidine, 1,1'-(2,4-thiazolediyl)bis-
170492-28-1

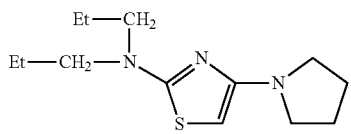

2-Thiazolamine, N,N-dipropyl-4-(1-pyrrolidinyl)-
169195-69-1

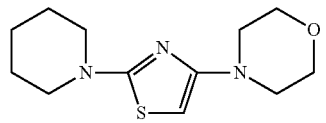

Morpholine, 4-[2-(1-piperidinyl)-4-thiazolyl]-
169195-65-7

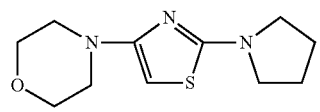

Morpholine, 4-[2-(1-pyrrolidinyl)-4-thiazolyl]-
169195-61-3

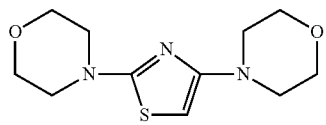

Morpholine, 4,4'-(2,4-thiazolediyl)bis-
169195-54-4

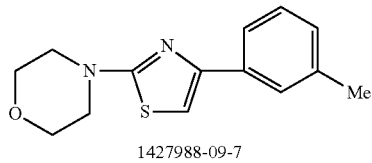

1427988-09-7
Morpholine, 4-[4-(3-methylphenyl)-2-thiazolyl]-

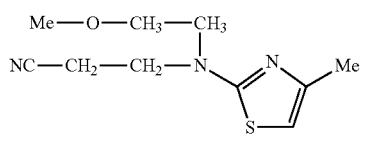

1408747-45-4
Propanenitrile, 3-[(2-methoxyethyl)(4-methyl-2-thiazolyl)amino]-

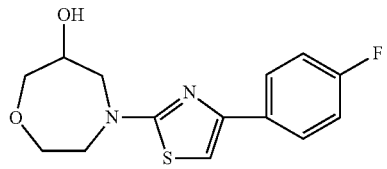

2-Thiazolamine, N,N-diethyl-4-(1-pyrrolidinyl)-
170492-33-8

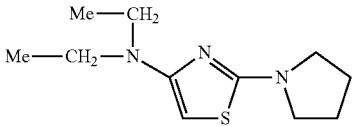 [SMILES: CCN(CC)c1csc(N2CCCC2)n1]

4-Thiazolamine, N,N-diethyl-2-(1-pyrrolidinyl)-
170492-26-9

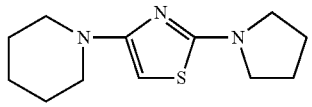 [SMILES: c1sc(N2CCCC2)nc1N1CCCCC1]

Piperidine, 1-[2-(1-pyrrolidinyl)-4-thiazolyl]-
169195-67-9

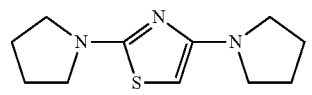

Thiazole, 2,4-di-1-pyrrolidinyl-
169195-63-5

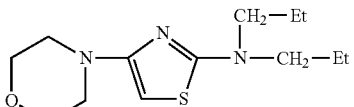

2-Thiazolamine, 4-(4-morpholinyl)-N,N-dipropyl-
169195-57-7

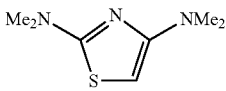

4-Thiazolediamine, N2,N2,N4,N4-tetramethyl-
70310-46-2

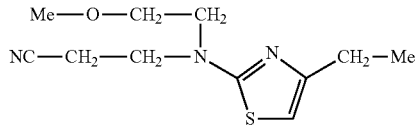

1409712-48-6
Propanenitrile, 3-[(4-ethyl-2-thiazolyl)(2-methoxyethyl)amino]-

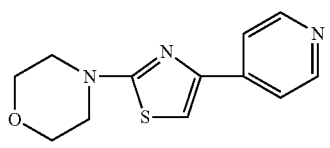 [SMILES: c1cc(-c2csc(N3CCOCC3)n2)ccn1]

1400302-74-0
Morpholine, 4-[4-(4-pyridinyl)-2-thiazolyl]-

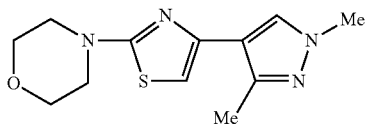 [SMILES: Cc1nn(C)cc1-c1csc(N2CCOCC2)n1]

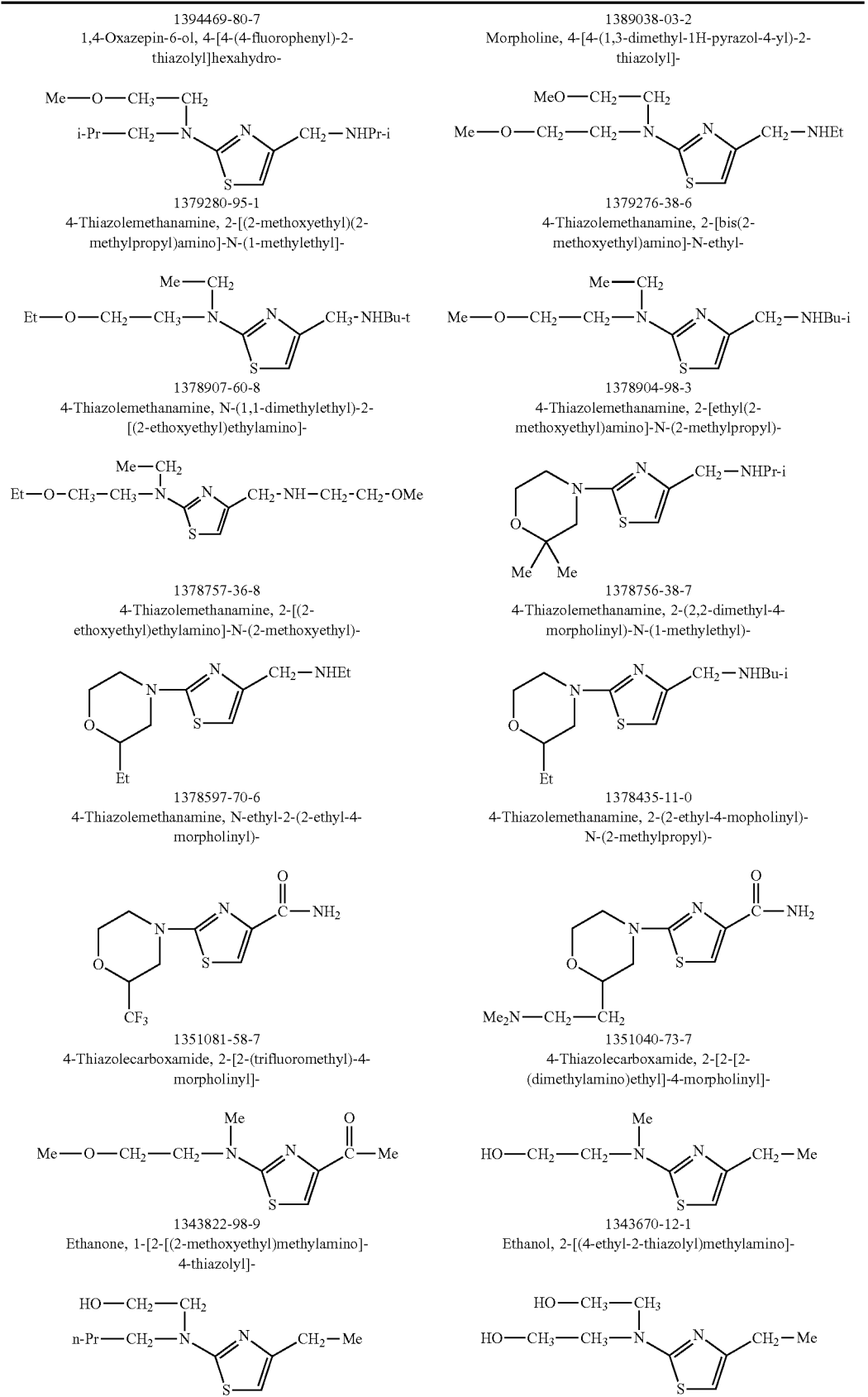

1343133-67-4
Ethanol, 2-[butyl(4-ethyl-2-thiazolyl)amino]-

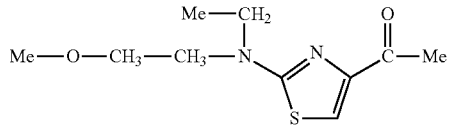

1342054-56-1
Ethanone, 1-[2-[ethyl(2-methoxyethyl)amino]-4-thiazolyl]-

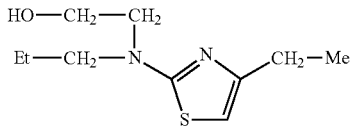 [SMILES: CCCN(CCO)c1nc(CC)cs1]

1339541-62-6
Ethanol, 2-[(4-ethyl-2-thiazolyl)propylamino]-

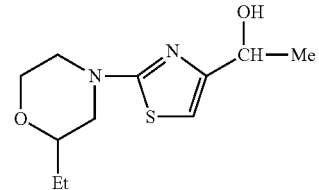 [SMILES: CCC1CN(c2nc(C(C)O)cs2)CCO1]

1339205-39-8
4-Thiazolemethanol, 2-(2-ethyl-4-morpholinyl)-α-methyl-

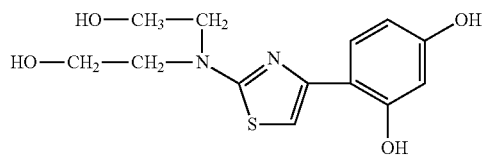 [SMILES: OCCN(CCO)c1nc(-c2ccc(O)cc2O)cs1]

1335232-10-4
1,3-Benzenediol, 4-[2-[bis(2-hydroxyethyl)amino]-4-thiazolyl]-

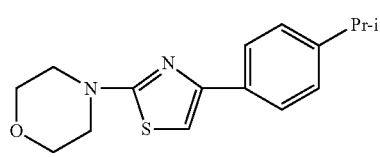

1286070-28-7
Morpholine, 4-[4-[4-(1-methylethyl)phenyl]-2-thiazolyl]-

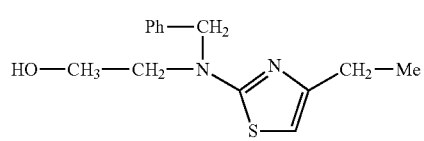

1271608-86-6
Ethanol, 2-[(4-ethyl-2-thiazolyl)(phenylmethyl)amino]-

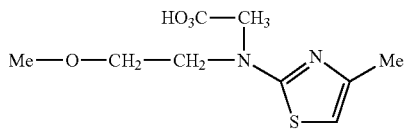

1342615-02-4
Ethanol, 2,2'-[(4-ethyl-2-thiazolyl)imino]bis-

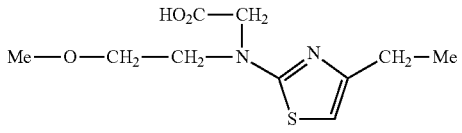

1341439-60-8
Glycine, N-(4-ethyl-2-thiazolyl)-N-(2-methoxyethyl)-

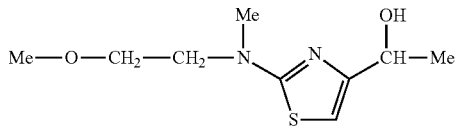

1339319-53-7
4-Thiazolemethanol, 2-[(2-methoxyethyl)methylamino]-α-methyl-

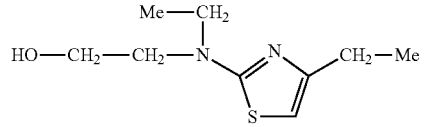

1339133-79-7
Ethanol, 2-[ethyl(4-ethyl-2-thiazolyl)amino]-

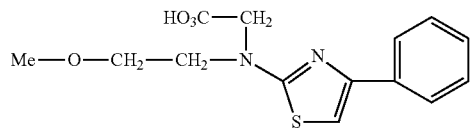

1303757-32-5
Glycine, N-(2-methoxyethyl)-N-(4-phenyl-2-thiazolyl)-

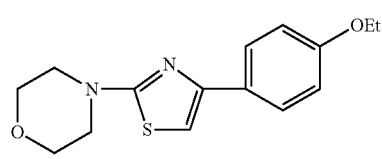 [SMILES: CCOc1ccc(-c2csc(N3CCOCC3)n2)cc1]

1286014-36-5
Morpholine, 4-[4-(4-ethoxyphenyl)-2-thiazolyl]-

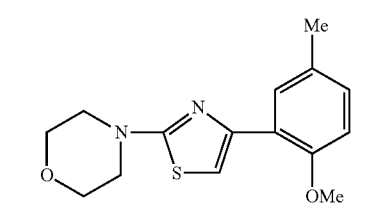 [SMILES: COc1ccc(C)cc1-c1csc(N2CCOCC2)n1]

1252154-09-8
Morpholine, 4-[4-(2-methoxy-5-methyl)phenyl)-2-thiazolyl]-

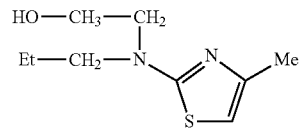

1251030-88-2
Glycine, N-(2-methoxyethyl)-N-(4-methyl-2-thiazolyl)-

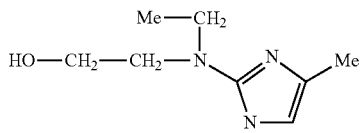 [SMILES: CCN(CCO)c1nc(C)cs1]

1249721-04-7
Ethanol, 2-[ethyl(4-methyl-2-thiazolyl)amino]-

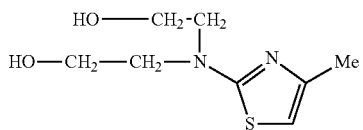

1247143-32-3
Ethanol, 2,2'-[(4-methyl-2-thiazolyl)imino]bis-

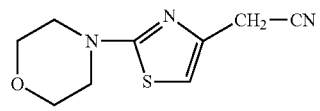

1023811-14-4
4-Thiazoleacetonitrile, 2-(4-morpholinyl)-

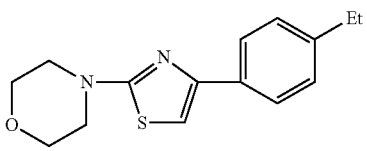

1004719-00-9
Morpholine, 4-[4-(4-ethylphenyl)-2-thiazolyl]-

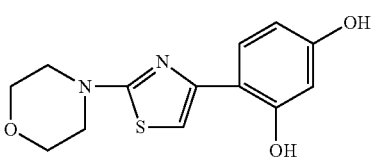

923850-84-4
1,3-Benzenediol, 4-[2-(4-morpholinyl)-4-thiazolyl]-

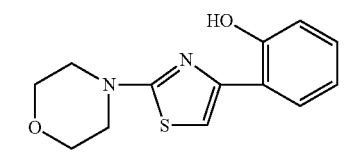

771436-47-6
Phenol, 2-[2-(4-morpholinyl)-4-thiazolyl]-

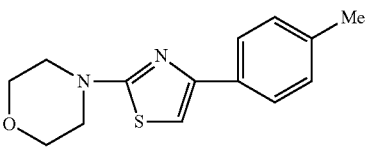

1250660-05-9
Ethanol, 2-[(4-methyl-2-thiazolyl)propylamino]-

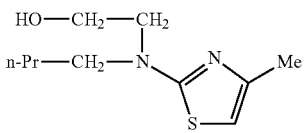

1249678-75-8
Ethanol, 2-[butyl(4-methyl-2-thiazolyl)amino]-

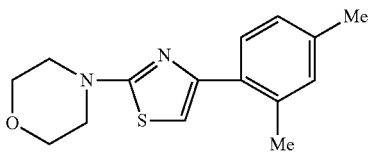 [SMILES: Cc1ccc(-c2csc(N3CCOCC3)n2)c(C)c1]

1136631-38-3
Morpholine, 4-[4-(2,4-dimethylphenyl)-2-thiazolyl]-

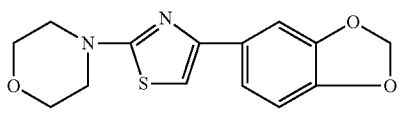 [SMILES: c1cc2c(cc1-c1csc(N3CCOCC3)n1)OCO2]

1013299-22-3
Morpholine, 4-[4-(1,3-benzodioxol-5-yl)-2-thiazolyl]-

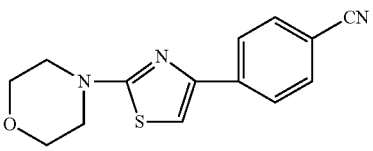 [SMILES: N#Cc1ccc(-c2csc(N3CCOCC3)n2)cc1]

930082-29-4
Benzonitrile, 4-[2-(4-morpholinyl)-4-thiazolyl]

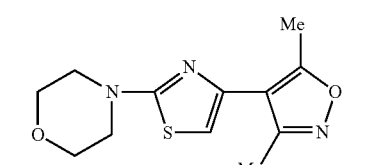

783252-70-0
Morpholine, 4-[4-(3,5-dimethyl-4-isothiazolyl)-2-thiazolyl]-

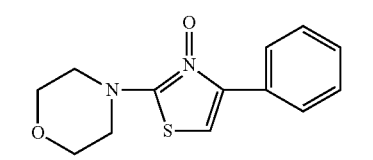 [SMILES: [O-][n+]1c(-c2ccccc2)csc1N1CCOCC1]

746552-23-8
Morpholine, 4-(3-oxido-4-phenyl-2-thiazolyl)-

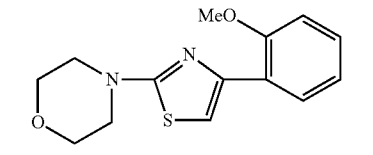

-continued 732975-41-6
Morpholine, 4-[4-(4-methylphenyl)-2-thiazolyl]-

521318-88-7
Morpholine, 4-[4-(2-methoxyphenyl)-2-thiazolyl]-

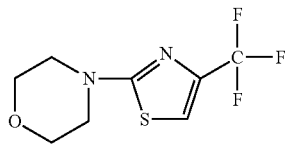 [SMILES: FC(F)(F)c1csc(N2CCOCC2)n1]

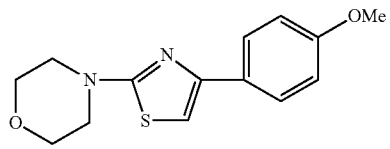 [SMILES: COc1ccc(-c2csc(N3CCOCC3)n2)cc1]

265107-02-6
Morpholine, 4-[4-(trifluoromethyl)-2-thiazolyl]-

256661-25-3
Morpholine, 4-[4-(4-methoxyphenyl)-2-thiazolyl]-

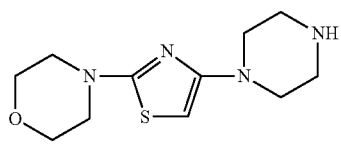 [SMILES: c1sc(N2CCOCC2)nc1N1CCNCC1]

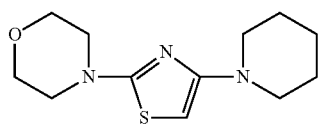 [SMILES: c1sc(N2CCOCC2)nc1N1CCCCC1]

192332-20-0
Morpholine, 4-[4-(1-piperazinyl)-2-thiazolyl]-

192332-18-6
Morpholine, 4-[4-(1-piperidinyl)-2-thiazolyl]

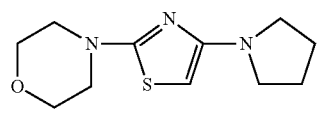 [SMILES: c1sc(N2CCOCC2)nc1N1CCCC1]

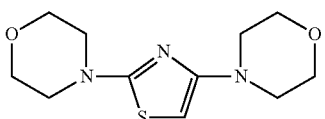

170492-35-0
Morpholine, 4-[4-(1-pyrrolidinyl)-2-thiazolyl]-

169195-54-4
Morpholine, 4,4'-(214-thiazolediyl)bis-

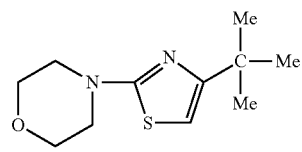

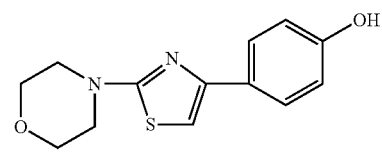

164397-09-5
Morpholine, 4-[4-(1,1-dimelhylethyl)-2-thiazolyl]-

145889-64-1
Phenol, 4-[2-(4-morpholinyl)-4-thiazolyl]

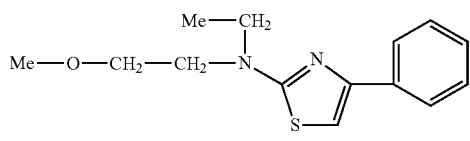 [SMILES: CCN(CCOC)c1nc(-c2ccccc2)cs1]

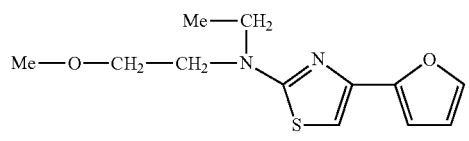 [SMILES: CCN(CCOC)c1nc(-c2ccco2)cs1]

133694-26-5
2-Thiazolamine, N-ethyl-N-(2-methoxyethyl)-4-phenyl- 130531-78-1
2-Thiazolamine, N-ethyl-4-(2-furanyl)-N-(2-methoxyethyl)-

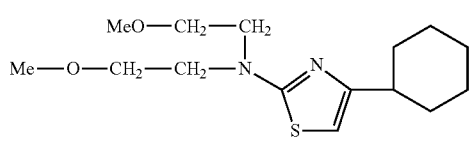 [SMILES: COCCN(CCOC)c1nc(C2CCCCC2)cs1]

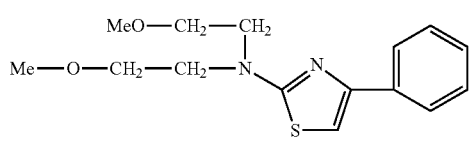 [SMILES: COCCN(CCOC)c1nc(-c2ccccc2)cs1]

-continued 130531-76-9
2-Thiazolamine, 4-cyclohexyl-N,N-bis(2-methoxyethyl)-

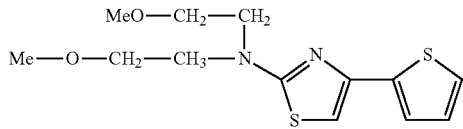

130531-64-5
2-Thiazolamine, N,N-bis(2-methoxyethyl)-4-phenyl-

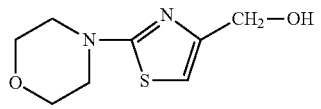 [SMILES: OCc1csc(N2CCOCC2)n1]

130531-63-4
2-Thiazolamine, N,N-bis(2-methoxyethyl)-4-(2-thienyl)-

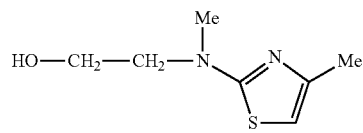 [SMILES: Cc1csc(N(C)CCO)n1]

C8 H12 N2 O2 S
2-(4-Morpholinyl)-4-(hydroxymethyl)thiazole

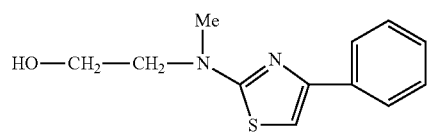

122320-85-8
Ethanol, 2-[methyl(4-methyl-2-thiazolyl)amino]-

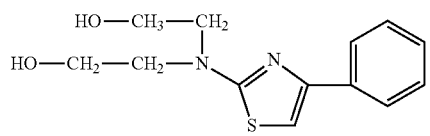

122320-82-5
Ethanol, 2-[methyl(4-phenyl-2-thiazolyl)amino]-

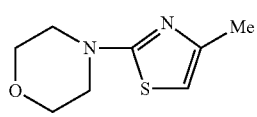 [SMILES: Cc1csc(N2CCOCC2)n1]

84552-01-2
Ethanol, 2,2'-[(4-phenyl-2-thiazolyl)imino]bis-

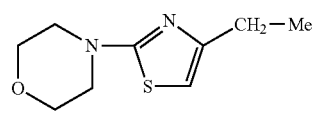 [SMILES: CCc1csc(N2CCOCC2)n1]

58350-40-6
Morpholine, 4-(4-methyl-2-thiazolyl)-

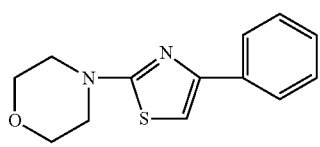

41817-60-1
Morpholine, 4-(4-ethyl-2-thiazolyl)-

19983-28-9
2-Morpholino-4-phenylthiazole.

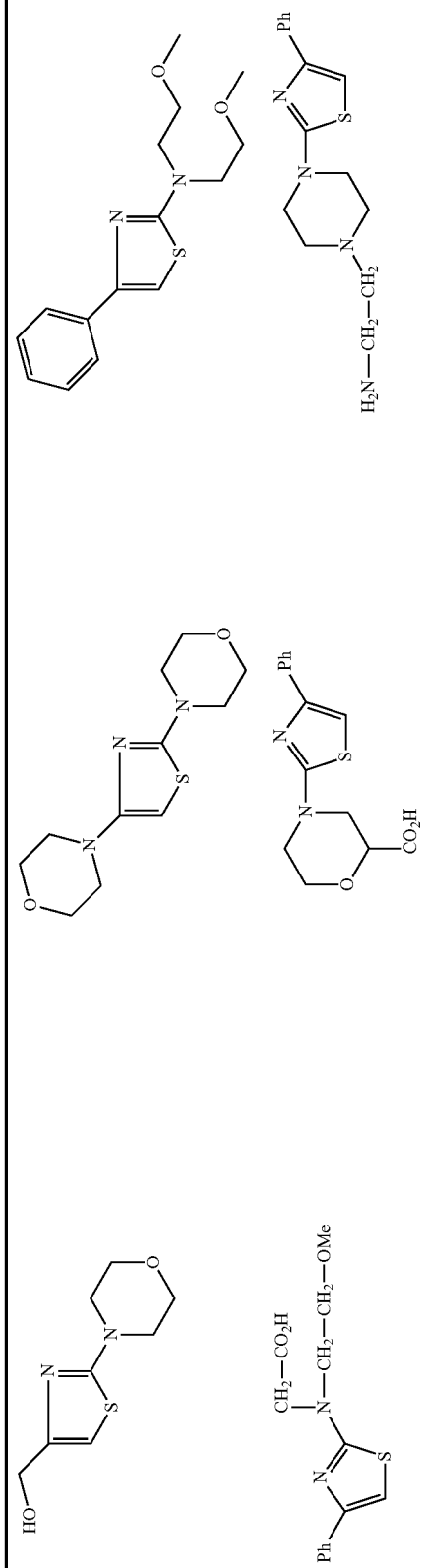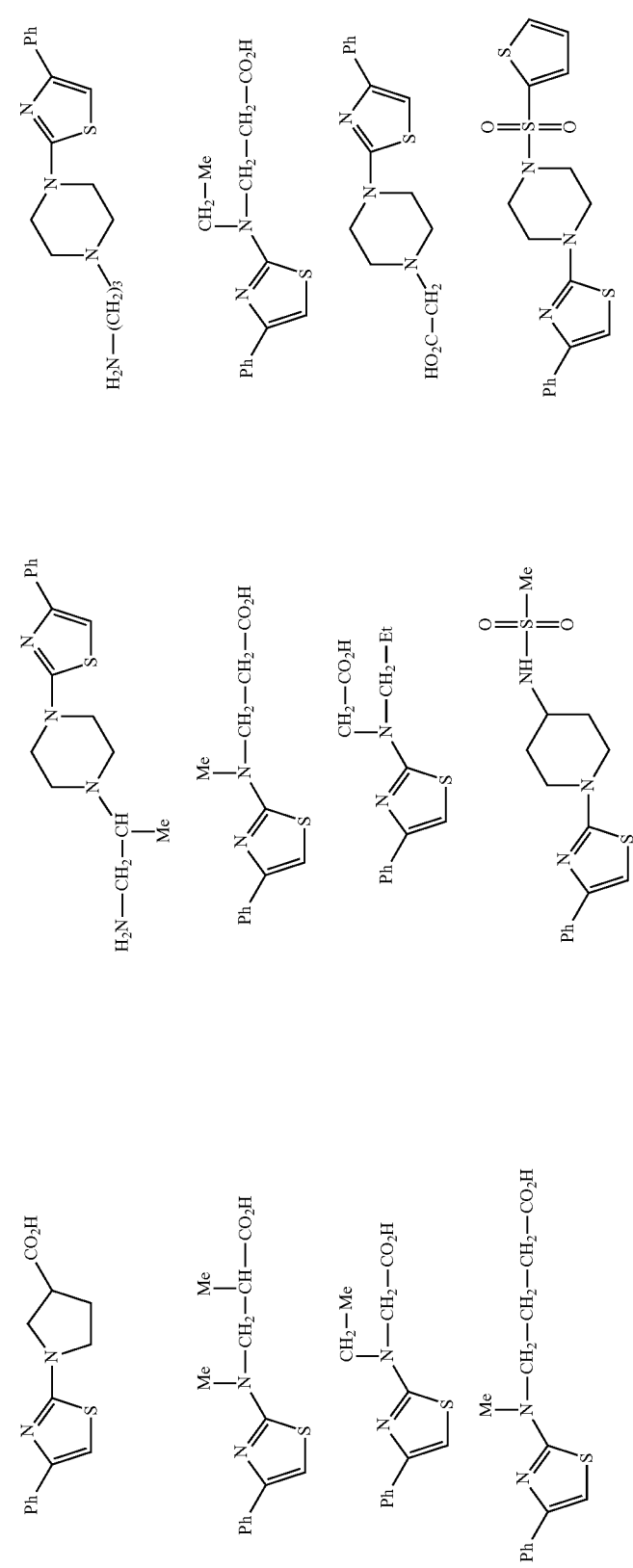

91 92
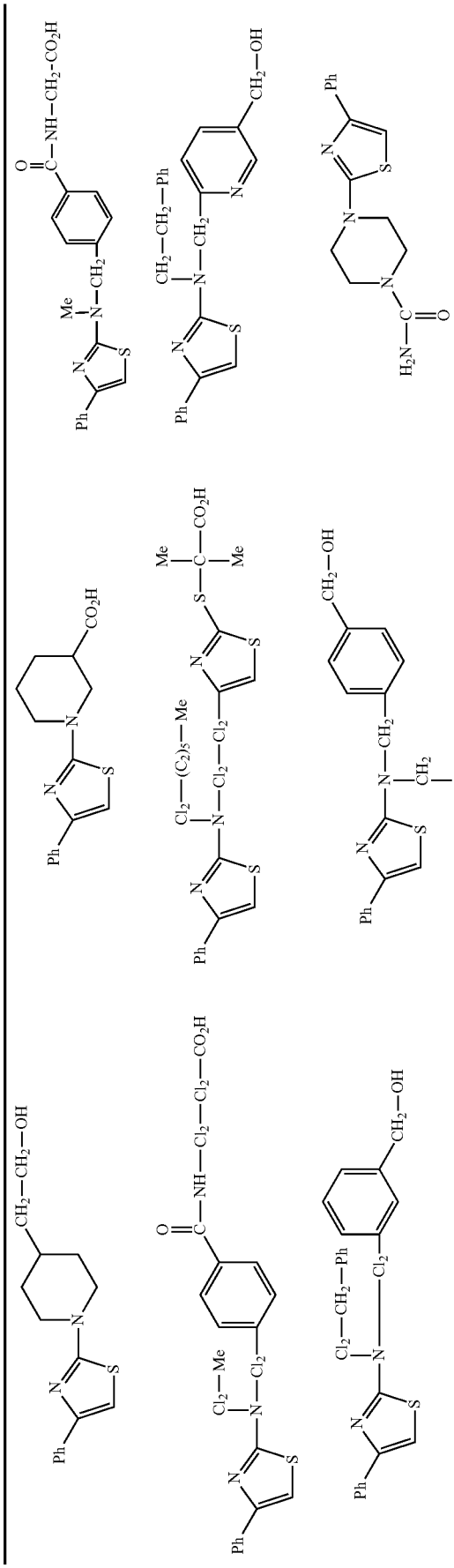
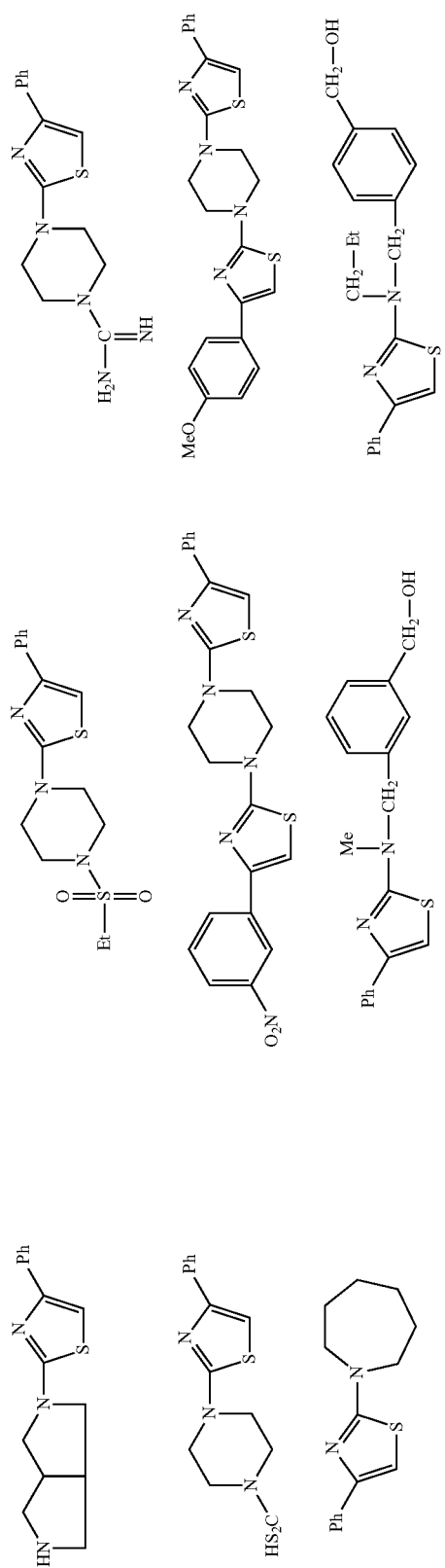

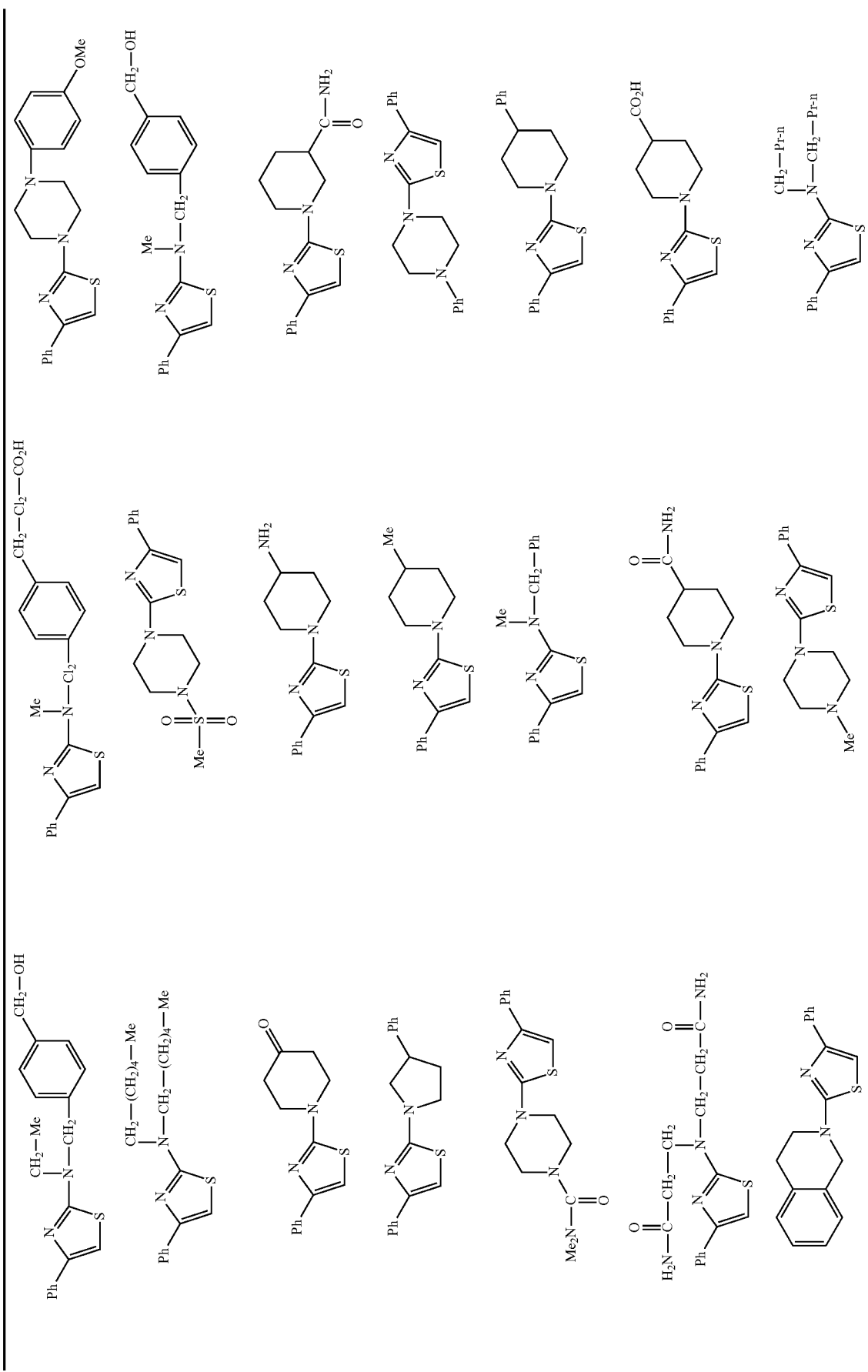

-continued
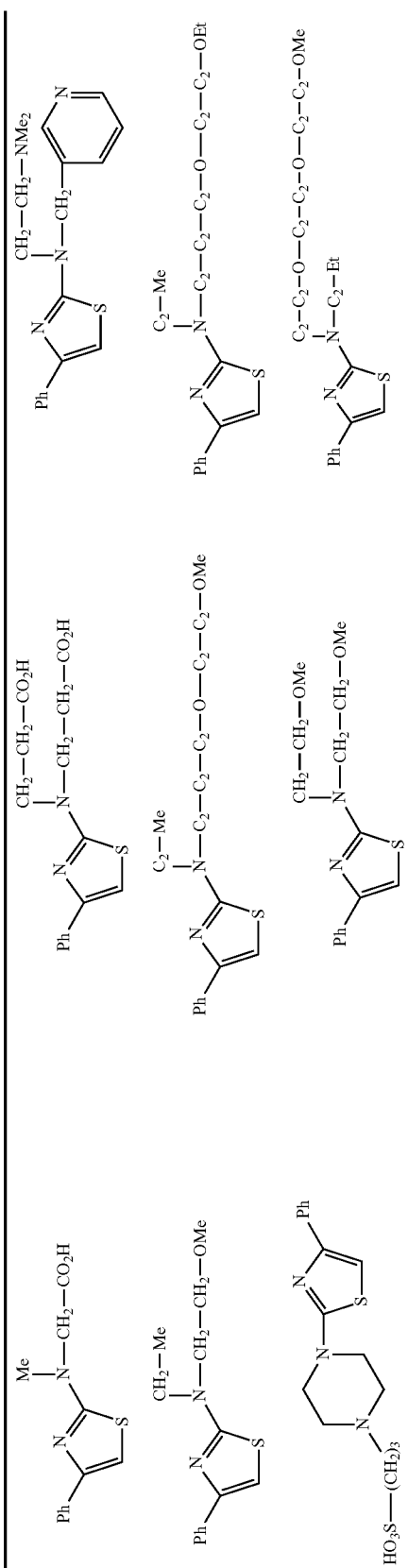
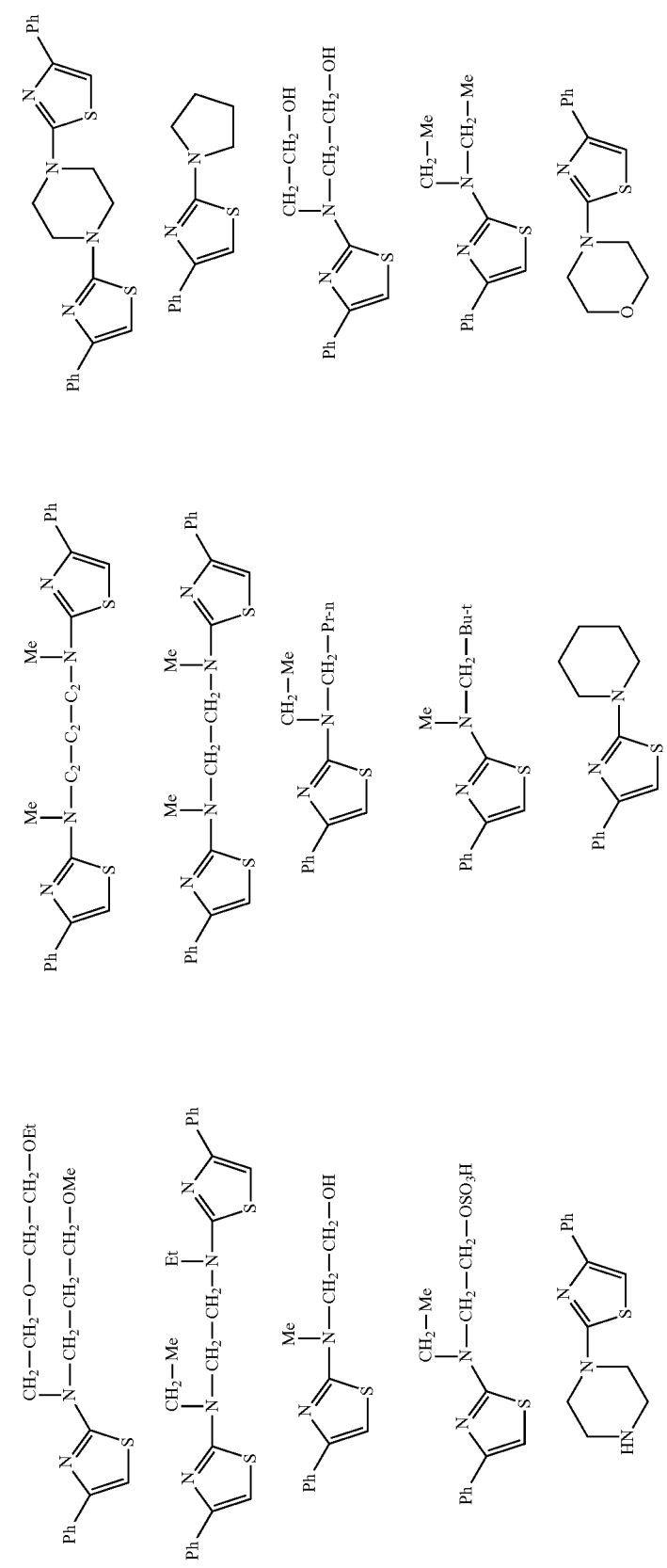

-continued
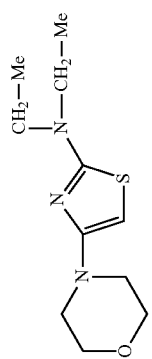 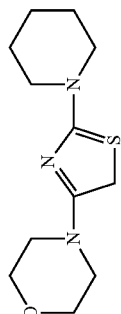 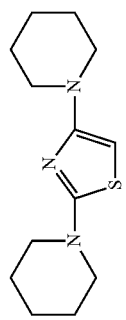 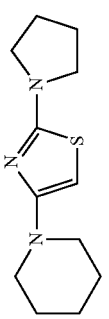 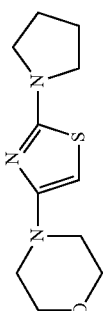 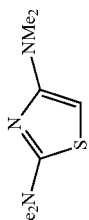 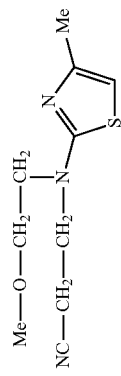
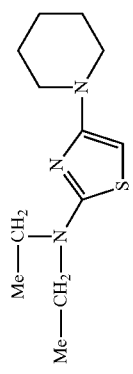 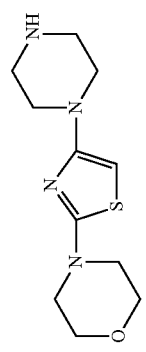 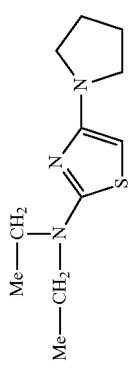 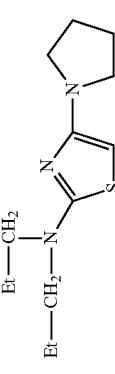 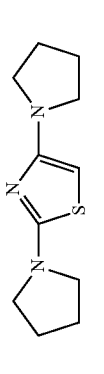 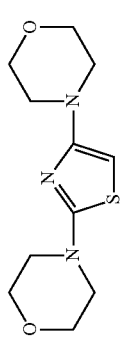 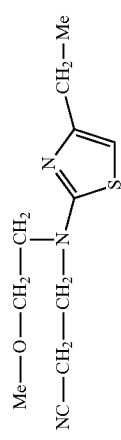
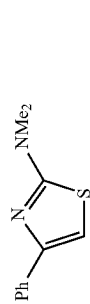 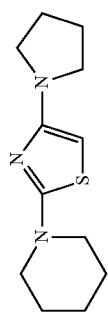 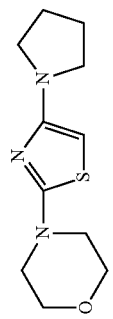 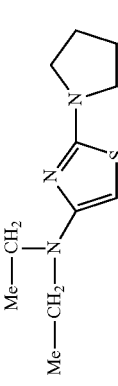 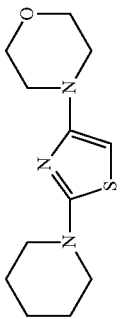 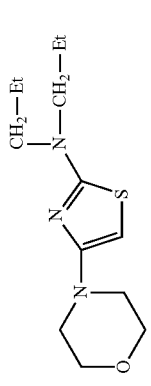 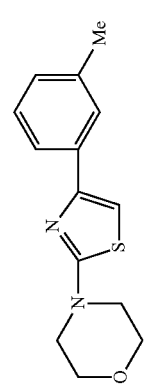

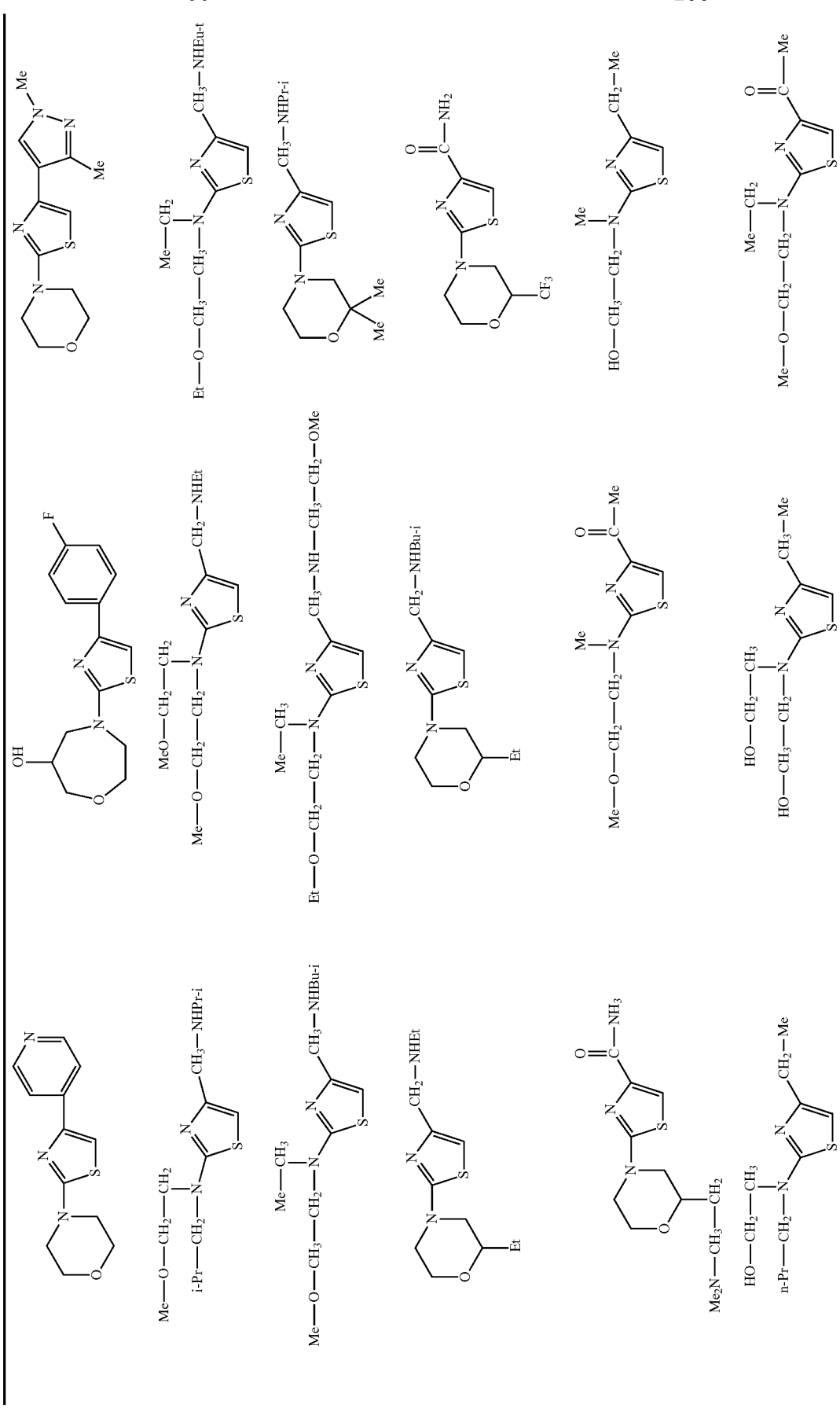

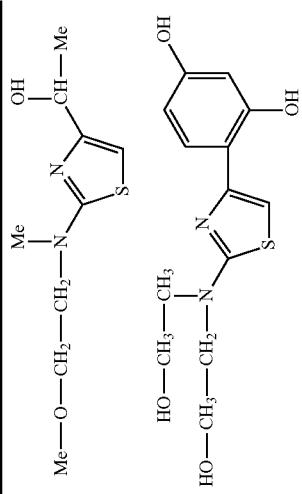
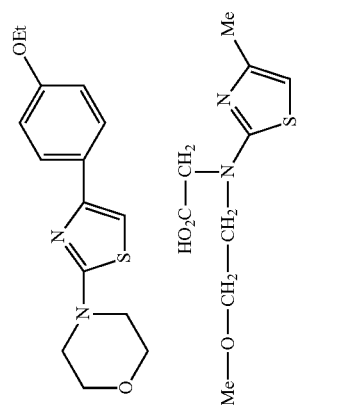
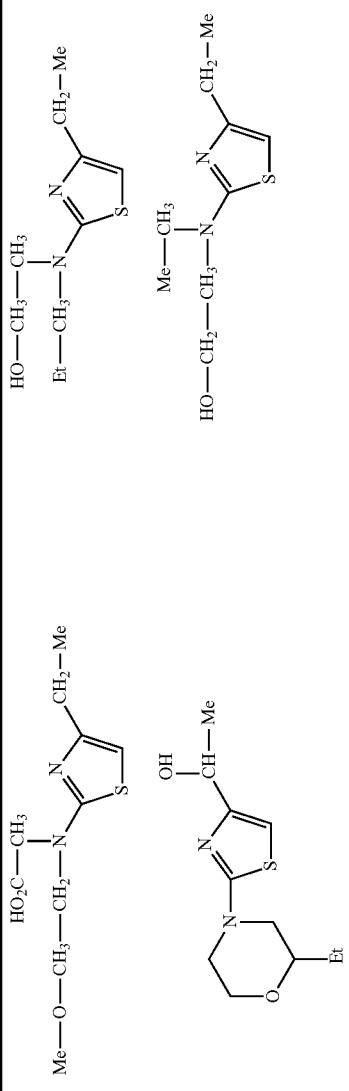
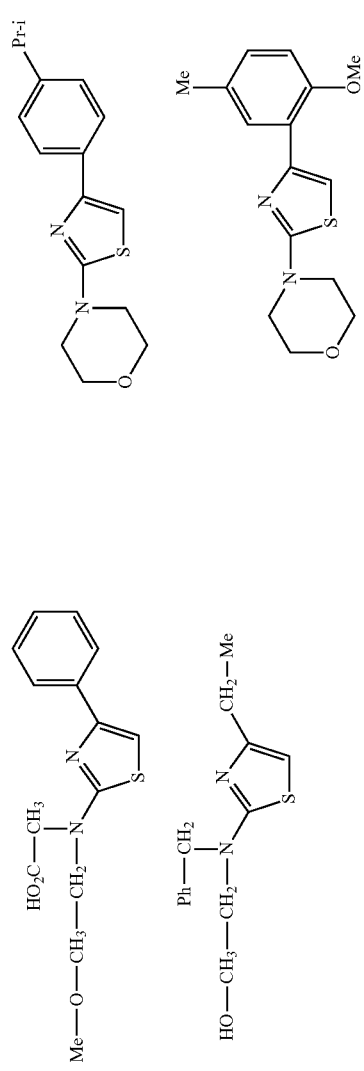
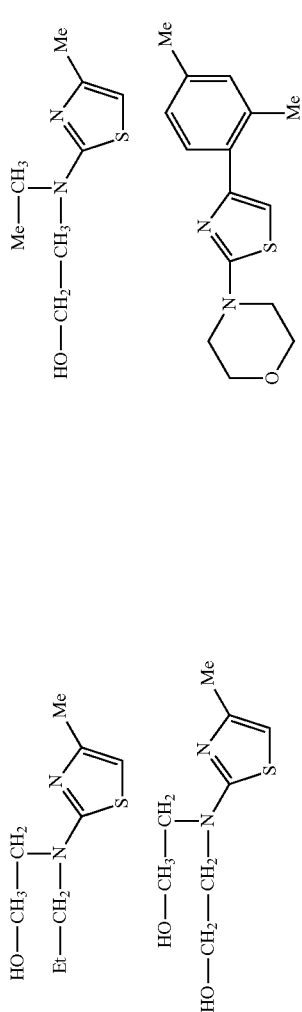

-continued
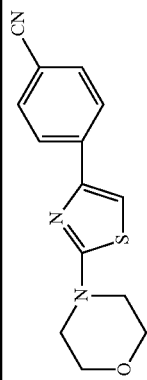 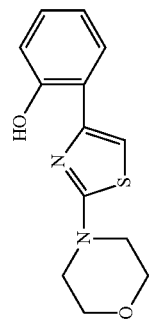 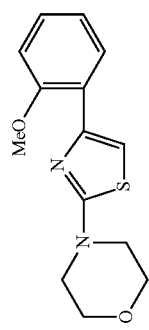 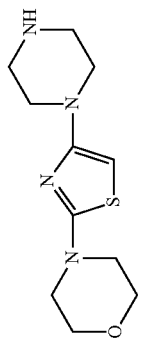 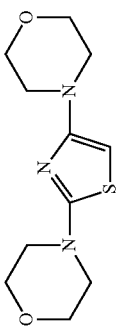 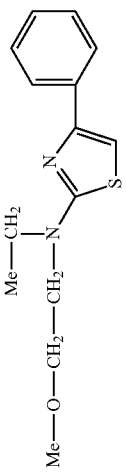
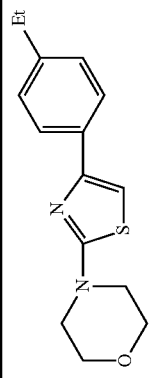 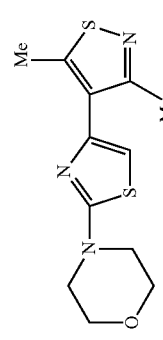 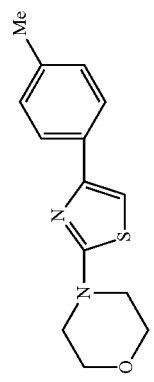 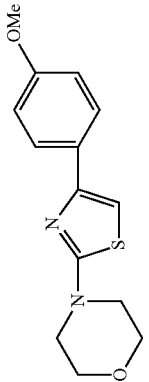 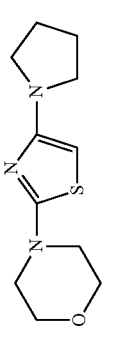 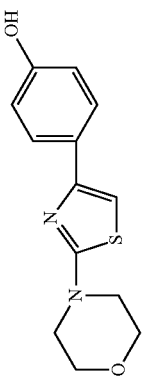
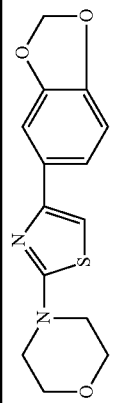 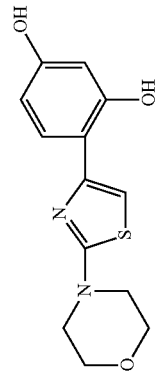 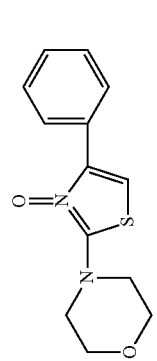 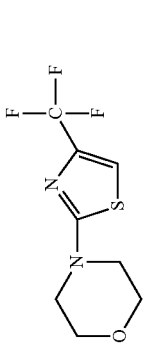 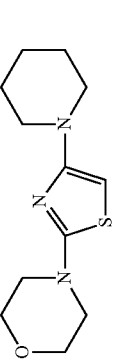 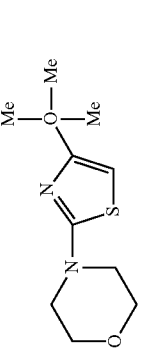

-continued
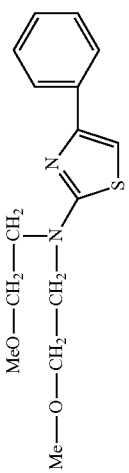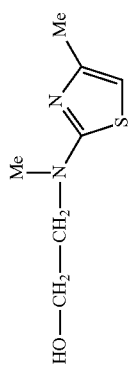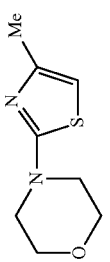
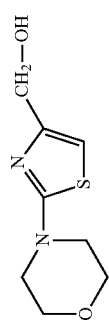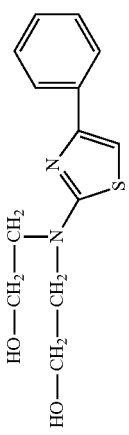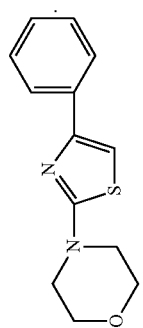
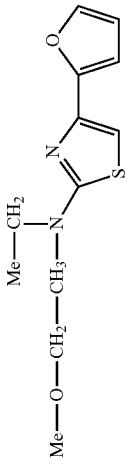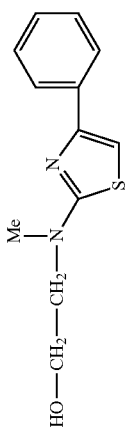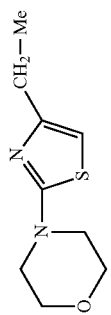

12. The composition according to claim 11, wherein the at least one heteroaryl coupler is chosen from those corresponding to formula 1, 2, or 3.

13. The composition according to claim 1, wherein the at least one heteroaryl coupler is present in an amount ranging from about 0.001% to about 20% by weight, relative to the total weight of the composition.

14. The composition according to claim 1, further comprising at least one fatty substance, wherein the fatty substance is present in an amount ranging from about 10% to about 80% by weight, relative to the total weight of the composition.

15. The composition according to claim 14, wherein the at least one fatty substance is liquid at 25° C. and atmospheric pressure, and is chosen from $C_6$-$C_{16}$ hydrocarbons, hydrocarbons containing more than 16 carbon atoms, triglycerides, fatty alcohols, esters of fatty acids and/or of fatty alcohols other than triglycerides, liquid petrolatum, octyl-2-dodecanol polydecenes, liquid fatty alcohols, or mixtures thereof.

16. The composition according to claim 1, further comprising at least one metal catalyst chosen from organic acid salts of transition metals, mineral salts of rare-earth metals, and solvates, hydrates, or enantiomers thereof.

17. The composition according to claim 16, wherein the at least one metal catalyst is chosen from metal salts of oxidation state II, which bear two ligands derived from $C_2$-$C_{10}$ carboxylic acid or from (poly)hydroxy acid, wherein the metal salts are optionally complexed with two carboxylate groups corresponding to formula (II) below:

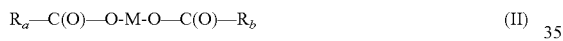

wherein:
M is chosen from a metal (II) or metal$^{2+}$ in oxidation state 2, and
$R_a$ and $R_b$, which may be identical or different, are chosen from (poly)(hydroxy)($C_1$-$C_6$)alkyl groups.

18. The composition according to claim 1, further comprising at least one alkaline agent chosen from mineral, organic, or hybrid alkaline agents, aqueous ammonia, alkali metal carbonates or bicarbonates, sodium carbonate, bicarbonate, potassium carbonate, sodium hydroxide, potassium hydroxide, organic amines, alkanolamines, oxyethylenated and/or oxypropylenated ethylenediamines, amino acids the compounds corresponding to formula (III) below, or mixtures thereof:

wherein:
W is a divalent $C_1$-$C_6$ alkylene radical optionally substituted with at least one hydroxyl group or a $C_1$-$C_6$ alkyl radical, and/or optionally interrupted with at least one heteroatom, O, or $NR_u$; and
$R_x$, $R_y$, $R_z$, $R_t$, and $R_u$, which may be identical or different, are chosen from a hydrogen atom, $C_1$-$C_6$ alkyl, $C_1$-$C_6$ hydroxyalkyl, or $C_1$-$C_6$ aminoalkyl radical.

19. The composition according to claim 1, further comprising at least one chemical oxidizing agent chosen from hydrogen peroxide, urea peroxide, alkali metal bromates, persalts, perborates, persulfates, or peracids.

20. A method for dyeing keratin fibers, comprising applying to the keratin fibers a final composition comprising:
i) at least one oxidation base chosen from heterocyclic bases or para-phenylenediamine bases; and
ii) at least one heteroaryl coupler corresponding to formula (I) below, the addition salts thereof with an organic or mineral acid or base, optical or geometrical isomers, tautomers, or solvates thereof:

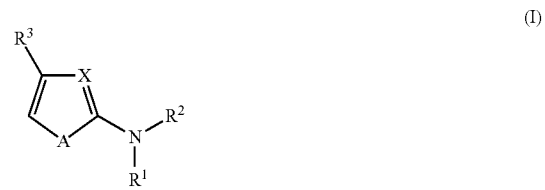

wherein:
A is chosen from oxygen or sulfur atoms;
X is chosen from a nitrogen atom or a C—$R^4$ group;
$R^1$ and $R^2$, which may be identical or different, are chosen from a linear or branched ($C_1$-$C_4$) alkyl group, optionally interrupted with at least one heteroatom, and optionally hydrogenated or ($C_1$-$C_4$)alkylated, and/or optionally substituted; an optionally substituted aryl; an optionally substituted heteroaryl; or an optionally substituted (hetero)cycloalkyl; or alternatively, $R^1$ and $R^2$ form, together with the nitrogen atom that bears them, an optionally substituted heterocycloalkyl, optionally comprising at least one heteroatom chosen from oxygen, sulfur, or nitrogen; and
$R^3$ and $R^4$, which may be identical or different, are chosen from a linear or branched ($C_1$-$C_4$) alkyl group, optionally interrupted with at least one heteroatom, and optionally hydrogenated or ($C_1$-$C_4$)alkylated, and/or optionally substituted with at least one group; an optionally substituted aryl; an optionally substituted heteroaryl, or an optionally substituted (hetero)cycloalkyl.

21. The method according to claim 20, wherein the final composition is derived from the mixing of a composition (A) and a composition (B), wherein:
composition (A) comprises:
the at least one oxidation base,
the at least one heteroaryl coupler, and
optionally at least one alkaline agent; and
composition (B) comprises at least one chemical oxidizing agent;
wherein at least one of the compositions (A) and (B) comprises:
at least one fatty substance, and
optionally, at least one metal catalyst; and
further wherein the fatty substance of the final composition is present in an amount of at least 10% by weight, relative to the total weight of the final composition.

22. The method according to claim 20, wherein the final composition is derived from the mixing of an anhydrous composition (A'), a composition (B'), and a composition (C'), wherein:
  anhydrous composition (A') comprises at least one fatty substance;
  composition (B') comprises:
    the at least one oxidation base, and
    the at least one heteroaryl coupler; and
  composition (C') comprises at least one chemical oxidizing agent;
  wherein at least one of the compositions (A') or (B') comprises at least one alkaline agent;
  optionally, at least one of the compositions (A'), (B'), or (C') comprises at least one metal catalyst; and
  further wherein the fatty substance is present in the final composition in an amount of at least 10% by weight, relative to the total weight of the final composition.

23. A multi-compartment device comprising:
  a first compartment comprising a composition (A), composition (A) comprising:
    at least one oxidation base,
    at least one heteroaryl coupler corresponding to formula (I) below, the addition salts thereof with an organic or mineral acid or base, optical or geometrical isomers, tautomers, or solvates thereof:

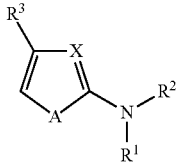

(I)

wherein:
  A is chosen from oxygen or sulfur atoms;
  X is chosen from a nitrogen atom or a C—$R^4$ group;
  $R^1$ and $R^2$, which may be identical or different, are chosen from a linear or branched ($C_1$-$C_4$) alkyl group, optionally interrupted with at least one heteroatom, and optionally hydrogenated or ($C_1$-$C_4$) alkylated, and/or optionally substituted; an optionally substituted aryl; an optionally substituted heteroaryl; or an optionally substituted (hetero)cycloalkyl; or alternatively, $R^1$ and $R^2$ form, together with the nitrogen atom that bears them, an optionally substituted heterocycloalkyl, optionally comprising at least one heteroatom chosen from oxygen, sulfur, or nitrogen; and
  $R^3$ and $R^4$, which may be identical or different, are chosen from a linear or branched ($C_1$-$C_4$) alkyl group, optionally interrupted with at least one heteroatom, and optionally hydrogenated or ($C_1$-$C_4$) alkylated, and/or optionally substituted with at least one group; an optionally substituted aryl; an optionally substituted heteroaryl, or an optionally substituted (hetero)cycloalkyl, and
  optionally, at least one alkaline agent; and
a second compartment comprising a composition (B), composition (B) comprising at least one chemical oxidizing agent;
wherein at least one of the compositions (A) and (B) comprises:
  at least one fatty substance, and
  optionally, at least one metal catalyst;
further wherein the fatty substance of the composition resulting from the mixing of compositions (A)+(B) is present in an amount of at least 10% by weight, relative to the total weight of the compositions (A)+(B).

* * * * *

UNITED STATES PATENT AND TRADEMARK OFFICE
CERTIFICATE OF CORRECTION

| | |
|---|---|
| PATENT NO. | : 9,993,409 B2 |
| APPLICATION NO. | : 15/311263 |
| DATED | : June 12, 2018 |
| INVENTOR(S) | : Alain Lagrange et al. |

It is certified that error appears in the above-identified patent and that said Letters Patent is hereby corrected as shown below:

Claim 11, Column 83, replace the formula labeled "1249721-04-07" with:

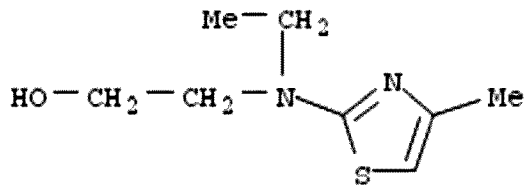

1249721-04-7
Ethanol, 2-[ethyl(4-methyl-2-thiazolyl)amino]-

Claim 11, Column 84, replace the formula labeled "783252-70-0" with:

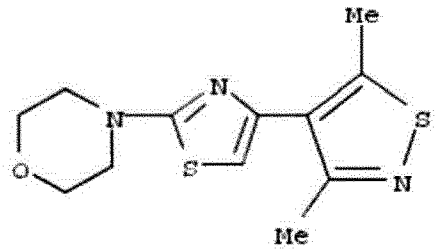

783252-70-0
Morpholine, 4-[4-(3,5-dimethyl-4-isothiazolyl)-2-thiazolyl]-

Signed and Sealed this
Thirtieth Day of October, 2018

Andrei Iancu
*Director of the United States Patent and Trademark Office*

CERTIFICATE OF CORRECTION (continued)
U.S. Pat. No. 9,993,409 B2

Claim 11, Column 100, middle position, replace the formula with:

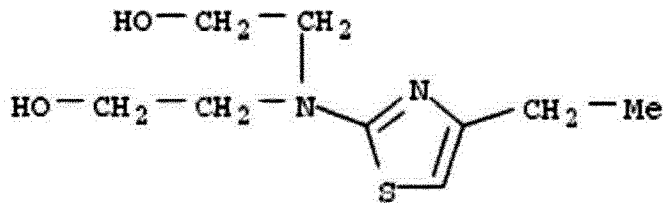

Claim 11, Column 101, first row, first position, replace the formula with:

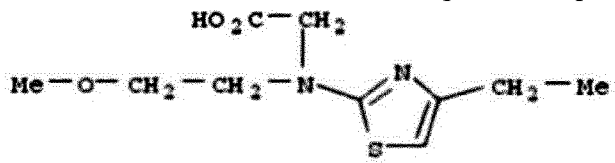

Claim 11, Column 101, first row, middle position, replace the formula with:

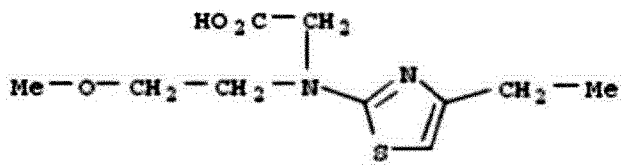

Claim 11, Column 101, second row, middle position, replace the formula with:

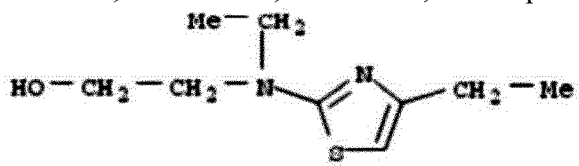

Claim 11, Column 101, second row, third position, replace the formula with:

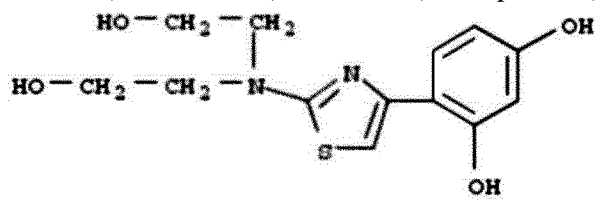

Claim 11, Column 101, third row, first position, replace the formula with:

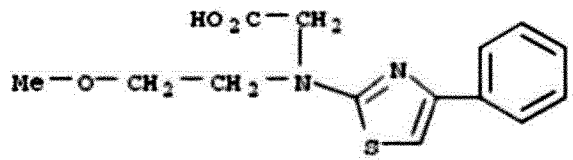

Claim 11, Column 102, first row, first position, replace the formula with: